(12) United States Patent
Kalafut

(10) Patent No.: US 9,959,389 B2
(45) Date of Patent: May 1, 2018

(54) MODELING OF PHARMACEUTICAL PROPAGATION AND PARAMETER GENERATION FOR INJECTION PROTOCOLS

(75) Inventor: John F. Kalafut, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 162 days.

(21) Appl. No.: 13/806,121

(22) PCT Filed: Jun. 24, 2011

(86) PCT No.: PCT/US2011/041802
§ 371 (c)(1),
(2), (4) Date: Apr. 18, 2013

(87) PCT Pub. No.: WO2011/163578
PCT Pub. Date: Dec. 29, 2011

(65) Prior Publication Data
US 2013/0211247 A1    Aug. 15, 2013

Related U.S. Application Data

(60) Provisional application No. 61/358,400, filed on Jun. 24, 2010.

(51) Int. Cl.
*G06F 19/00* (2018.01)
*A61B 6/00* (2006.01)

(52) U.S. Cl.
CPC .......... *G06F 19/3437* (2013.01); *A61B 6/507* (2013.01)

(58) Field of Classification Search
CPC ..... A61B 6/507; A61B 5/0044; A61B 5/0208; A61B 5/0205

(Continued)

(56) References Cited

U.S. PATENT DOCUMENTS 3,349,713 A    10/1967  Fassbender
3,520,295 A    7/1970   Kelly
(Continued)

FOREIGN PATENT DOCUMENTS

AT    259621 T    3/2004
AU    7381796 A   4/1997
(Continued)

OTHER PUBLICATIONS

Office Action dated Jan. 3, 2014 in U.S. Appl. No. 11/691,823.
(Continued)

*Primary Examiner* — Baisakhi Roy
(74) *Attorney, Agent, or Firm* — James R. Stevenson; Henry E. Bartony, Jr.

(57) ABSTRACT

A system includes a parameter generation system to determine at least one parameter for an injection procedure (for example, a parameter of an injection protocol or an imaging system parameter), the parameter generator system includes a physiologically based pharmacokinetic model to model propagation of a contrast medium injected into a patient including at least one of a non-linear saturation term in a peripheral venous compartment, at least one configurable transport delay term through at least one compartment, or an adaptation to model volumetric flow rate of blood and an effect thereof on the propagation of contrast medium after injection of contrast medium ceases. The physiologically based pharmacokinetic model can, for example, be discretizable.

28 Claims, 43 Drawing Sheets

(58) Field of Classification Search
USPC .................................................. 600/431, 432
See application file for complete search history.

(56) References Cited

U.S. PATENT DOCUMENTS

| | | |
|---|---|---|
| 3,523,523 A | 8/1970 | Heinrich et al. |
| 3,623,474 A | 11/1971 | Heilman et al. |
| 3,701,345 A | 10/1972 | Heilman et al. |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Bredesen et al. |
| 3,888,239 A | 6/1975 | Rubinstein |
| 3,895,220 A | 7/1975 | Nelson et al. |
| 3,898,983 A | 8/1975 | Bam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | LeFevre et al. |
| 4,044,757 A | 8/1977 | McWhorter et al. |
| 4,090,502 A | 5/1978 | Tajka |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,435,173 A | 3/1984 | Siposs et al. |
| 4,444,198 A | 4/1984 | Petre |
| 4,447,230 A | 5/1984 | Gula et al. |
| 4,448,200 A | 5/1984 | Brookes et al. |
| 4,474,476 A | 10/1984 | Thomsen |
| 4,477,923 A | 10/1984 | Baumann et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers de Beyl et al. |
| 4,552,130 A | 11/1985 | Kinsohita |
| 4,559,036 A | 12/1985 | Wunsch |
| 4,563,175 A | 1/1986 | LaFond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | DiGianfilippo et al. |
| 4,793,357 A | 12/1988 | Linstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Potaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | DiGianflilippo et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |

(56) References Cited

U.S. PATENT DOCUMENTS

| | | |
|---|---|---|
| 5,113,904 A | 5/1992 | Aslanian |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Lida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,174 A | 1/1994 | Plotkin et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Contruro |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,058 A | 1/1995 | Yonezawa |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,417,219 A | 5/1995 | Takamizawa et al. |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kampfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | DeVale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Ubert, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Ubert, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,881,124 A | 3/1999 | Giger et al. |
| 5,882,343 A | 3/1999 | Wilson et al. |
| 5,885,216 A | 3/1999 | Evans, III et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,337,992 B1 | 1/2002 | Gelman |
| 6,344,030 B1 | 2/2002 | Duchon et al. |
| 6,346,229 B1 | 2/2002 | Driehuys et al. |
| 6,381,486 B1 | 4/2002 | Mistretta et al. |

(56) References Cited

U.S. PATENT DOCUMENTS

| | | |
|---|---|---|
| 6,385,483 B1 | 5/2002 | Uber, III et al. |
| 6,387,098 B1 | 5/2002 | Cole et al. |
| 6,397,093 B1 | 5/2002 | Aldrich |
| 6,397,097 B1 | 5/2002 | Requardt |
| 6,397,098 B1 | 5/2002 | Uber, III et al. |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell Gisper Sauch et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1* | 10/2003 | Bae et al. ..................... 604/131 |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans, III et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,866,654 B2 | 3/2005 | Callan et al. |
| 6,876,720 B2 | 4/2005 | Tsuyuki |
| 6,879,853 B2 | 4/2005 | Meaney et al. |
| 6,887,214 B1 | 5/2005 | Levin et al. |
| 6,889,074 B2 | 5/2005 | Uber, III et al. |
| 6,898,453 B2 | 5/2005 | Lee |
| 6,901,283 B2 | 5/2005 | Evans, III et al. |
| 6,970,735 B2 | 11/2005 | Uber, III et al. |
| 6,972,001 B2 | 12/2005 | Emig et al. |
| 6,983,590 B2 | 1/2006 | Roelle et al. |
| 6,994,700 B2 | 2/2006 | Elkins et al. |
| 7,094,216 B2 | 8/2006 | Trombley, III et al. |
| 7,104,981 B2 | 9/2006 | Elkins et al. |
| 7,108,981 B2 | 9/2006 | Aoki et al. |
| 7,163,520 B2 | 1/2007 | Bernard et al. |
| 7,266,227 B2 | 9/2007 | Pedain et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,313,431 B2 | 12/2007 | Uber, III et al. |
| 7,325,330 B2 | 2/2008 | Kim et al. |
| 7,326,186 B2 | 2/2008 | Trombley, III et al. |
| 7,363,072 B2 | 4/2008 | Movahed |
| 7,492,947 B2 | 2/2009 | Nanbu |
| 7,522,744 B2 | 4/2009 | Bai et al. |
| 7,672,710 B2 | 3/2010 | Uber, III et al. |
| 7,672,711 B2 | 3/2010 | Haras et al. |
| 7,713,239 B2 | 5/2010 | Uber, III et al. |
| 7,734,331 B2 | 6/2010 | Dhawale et al. |
| 7,925,330 B2 | 4/2011 | Kalafut et al. |
| 7,937,134 B2 | 5/2011 | Uber, III |
| 8,086,001 B2 | 12/2011 | Bredno et al. |
| 8,295,914 B2 | 10/2012 | Kalafut et al. |
| 8,346,342 B2 | 1/2013 | Kalafut |
| 8,428,694 B2 | 4/2013 | Kalafut et al. |
| 8,486,017 B2 | 7/2013 | Masuda et al. |
| 8,705,819 B2 | 4/2014 | Carlsen et al. |
| 8,718,747 B2 | 5/2014 | Bjornerud et al. |
| 9,271,656 B2 | 3/2016 | Korporaal |
| 2001/0027265 A1 | 10/2001 | Prince |
| 2001/0041964 A1* | 11/2001 | Grass ..................... C40B 50/02 702/19 |
| 2001/0056233 A1 | 12/2001 | Uber et al. |
| 2002/0010551 A1 | 1/2002 | Wang et al. |
| 2002/0026148 A1 | 2/2002 | Uber |
| 2002/0091349 A1 | 7/2002 | Reich |
| 2002/0099254 A1 | 7/2002 | Movahed |
| 2002/0123702 A1 | 9/2002 | Cho |
| 2002/0151854 A1 | 10/2002 | Duchon et al. |
| 2002/0165445 A1 | 11/2002 | Uber et al. |
| 2003/0015078 A1 | 1/2003 | Taylor |
| 2003/0036694 A1 | 2/2003 | Liu |
| 2003/0050556 A1 | 3/2003 | Uber et al. |
| 2003/0088320 A1* | 5/2003 | Sale ..................... G05B 17/02 700/30 |
| 2003/0120171 A1 | 6/2003 | Diamantopoulos et al. |
| 2003/0135111 A1 | 7/2003 | Meaney et al. |
| 2003/0195462 A1 | 10/2003 | Mann et al. |
| 2003/0198691 A1* | 10/2003 | Cheung ............... A61K 38/1816 424/649 |
| 2003/0212364 A1 | 11/2003 | Mann et al. |
| 2003/0216683 A1 | 11/2003 | Shekalim |
| 2004/0008028 A1 | 1/2004 | Horger et al. |
| 2004/0010229 A1 | 1/2004 | Houde et al. |
| 2004/0011740 A1 | 1/2004 | Bernard et al. |
| 2004/0015078 A1 | 1/2004 | Evans et al. |
| 2004/0025452 A1 | 2/2004 | McLean |
| 2004/0039530 A1* | 2/2004 | Leesman ............... G06F 19/704 702/19 |
| 2004/0044302 A1 | 3/2004 | Bernard et al. |
| 2004/0064040 A1 | 4/2004 | Masuada et al. |
| 2004/0064041 A1 | 4/2004 | Lazzaro et al. |
| 2004/0074453 A1 | 4/2004 | Roelle et al. |
| 2004/0097806 A1 | 5/2004 | Hunter et al. |
| 2004/0097875 A1 | 5/2004 | Bae |
| 2004/0162484 A1 | 8/2004 | Nemoto |
| 2004/0163655 A1 | 8/2004 | Gelfand et al. |
| 2004/0167415 A1* | 8/2004 | Gelfand et al. ................ 600/500 |
| 2004/0215144 A1 | 10/2004 | Duchon et al. |
| 2004/0242994 A1* | 12/2004 | Brady et al. .................. 600/420 |
| 2005/0004517 A1 | 1/2005 | Courtney et al. |
| 2005/0053551 A1 | 3/2005 | Badiola |
| 2005/0112178 A1 | 5/2005 | Stem |
| 2005/0256441 A1 | 11/2005 | Lotan et al. |
| 2006/0013772 A1 | 1/2006 | LeWinter et al. |
| 2006/0052764 A1 | 3/2006 | Gelfand et al. |
| 2006/0074294 A1 | 4/2006 | Williams et al. |
| 2006/0079843 A1 | 4/2006 | Brooks et al. |
| 2006/0096388 A1 | 5/2006 | Gysling et al. |
| 2006/0184099 A1 | 8/2006 | Hong |
| 2006/0211989 A1 | 9/2006 | Rhinehart et al. |
| 2006/0235353 A1 | 10/2006 | Gelfand et al. |
| 2006/0235474 A1 | 10/2006 | Demarais |
| 2006/0239918 A1 | 10/2006 | Klotz et al. |
| 2006/0253064 A1 | 11/2006 | Gelfand et al. |
| 2006/0253353 A1 | 11/2006 | Weisberger |
| 2006/0270971 A1 | 11/2006 | Gelfand et al. |
| 2006/0271111 A1 | 11/2006 | Demarais et al. |
| 2007/0016016 A1 | 1/2007 | Haras et al. |
| 2007/0066892 A1 | 3/2007 | Haras et al. |
| 2007/0078330 A1 | 4/2007 | Haras et al. |
| 2007/0213662 A1* | 9/2007 | Kalafut ............... A61M 5/14546 604/96.01 |
| 2007/0225601 A1 | 9/2007 | Uber et al. |
| 2007/0244389 A1 | 10/2007 | Hoppel et al. |
| 2007/0255135 A1* | 11/2007 | Kalafut et al. ................ 600/431 |
| 2007/0282199 A1 | 12/2007 | Uber et al. |
| 2007/0282263 A1 | 12/2007 | Kalafute et al. |
| 2008/0009717 A1 | 1/2008 | Herrmann et al. |
| 2008/0045834 A1 | 2/2008 | Uber et al. |
| 2008/0046286 A1 | 2/2008 | Halsted |
| 2008/0097197 A1* | 4/2008 | Kalafut et al. ................ 600/431 |
| 2008/0097339 A1 | 4/2008 | Ranchod et al. |
| 2008/0101678 A1 | 5/2008 | Suliga et al. |
| 2008/0119715 A1 | 5/2008 | Gonzalez Molezzi et al. |
| 2008/0294035 A1* | 11/2008 | Zwick ................... A61B 5/0515 600/420 |
| 2009/0028968 A1* | 1/2009 | Tam ..................... A61K 36/48 424/757 |

(56) References Cited

U.S. PATENT DOCUMENTS

| | | | |
|---|---|---|---|
| 2009/0116711 A1* | 5/2009 | Larson et al. | 382/128 |
| 2009/0177050 A1 | 7/2009 | Griffiths et al. | |
| 2009/0226867 A1 | 9/2009 | Kalafut et al. | |
| 2010/0030073 A1 | 2/2010 | Kalafut | |
| 2010/0113887 A1 | 5/2010 | Kalafut et al. | |
| 2010/0114064 A1 | 5/2010 | Kalafut et al. | |
| 2012/0141005 A1 | 6/2012 | Djeridane et al. | |
| 2013/0041257 A1 | 2/2013 | Nemoto | |

FOREIGN PATENT DOCUMENTS

| | | |
|---|---|---|
| CA | 2045070 | 2/1992 |
| CA | 2077712 | 12/1993 |
| CA | 2234050 A1 | 4/1997 |
| CN | 1343107 | 4/2002 |
| CN | 101084036 A | 12/2007 |
| CN | 101742967 A | 6/2010 |
| DE | 3203594 | 8/1983 |
| DE | 3726452 | 2/1989 |
| DE | 4121568 | 10/1992 |
| DE | 4426387 A1 | 8/1995 |
| DE | 19702896 A1 | 7/1997 |
| DE | 19647701 A1 | 5/1998 |
| DE | 69530035 T2 | 9/2003 |
| DE | 69631607 T2 | 12/2004 |
| DK | 086973873 T3 | 6/2004 |
| EP | 0189491 | 8/1986 |
| EP | 0192786 | 9/1986 |
| EP | 0129910 | 11/1987 |
| EP | 0121216 | 8/1988 |
| EP | 0319275 A1 | 6/1989 |
| EP | 0337924 | 10/1989 |
| EP | 0343501 | 11/1989 |
| EP | 0364966 | 4/1990 |
| EP | 0365301 | 4/1990 |
| EP | 0245160 | 5/1990 |
| EP | 0372152 | 6/1990 |
| EP | 0378896 | 7/1990 |
| EP | 0429191 | 5/1991 |
| EP | 0475563 | 3/1992 |
| EP | 0595474 | 5/1994 |
| EP | 0600448 | 6/1994 |
| EP | 0619122 | 10/1994 |
| EP | 0439711 | 5/1995 |
| EP | 0439711 B1 | 5/1995 |
| EP | 0650738 A1 | 5/1995 |
| EP | 0650739 | 5/1995 |
| EP | 0702966 A2 | 3/1996 |
| EP | 0471455 | 11/1997 |
| EP | 0869738 A1 | 10/1998 |
| EP | 1262206 A2 | 12/2002 |
| EP | 1812101 A2 | 8/2007 |
| EP | 1835959 A2 | 9/2007 |
| EP | 2042100 A2 | 4/2009 |
| EP | 2097004 A2 | 9/2009 |
| EP | 2097835 A2 | 9/2009 |
| EP | 2170165 A1 | 4/2010 |
| ES | 2216068 T3 | 10/2004 |
| FR | 2493708 | 5/1982 |
| FR | 2561949 | 10/1985 |
| GB | 201800 | 8/1923 |
| GB | 2252656 | 8/1992 |
| GB | 2328745 A | 3/1999 |
| GB | 2207749 A2 | 7/2010 |
| JP | 50017781 | 2/1975 |
| JP | 58015842 | 1/1983 |
| JP | 59214432 | 12/1984 |
| JP | 60194934 | 10/1985 |
| JP | 60194935 | 10/1985 |
| JP | 60253197 | 12/1985 |
| JP | 62216199 | 9/1987 |
| JP | 63040538 | 2/1988 |
| JP | 63290547 | 11/1988 |
| JP | 1207038 | 8/1989 |
| JP | 2224647 | 9/1990 |
| JP | 2234747 | 9/1990 |
| JP | 3055040 | 3/1991 |
| JP | 4115677 | 4/1992 |
| JP | 5084296 | 4/1993 |
| JP | 7178169 A | 7/1995 |
| JP | 10211198 A | 8/1998 |
| JP | 2000506398 A | 5/2000 |
| JP | 2000175900 A | 6/2000 |
| JP | 2002-507438 | 3/2002 |
| JP | 2003-102724 A | 4/2003 |
| JP | 2003-116843 | 4/2003 |
| JP | 2003-210456 | 7/2003 |
| JP | 2003-225234 | 8/2003 |
| JP | 2004174008 A | 6/2004 |
| JP | 2004-519304 | 7/2004 |
| JP | 2004194721 A | 7/2004 |
| JP | 3553968 B2 | 8/2004 |
| JP | 2004236849 A | 8/2004 |
| JP | 2004298550 A | 10/2004 |
| JP | 2005511128 A | 4/2005 |
| JP | 2005-324007 | 11/2005 |
| JP | 2006075600 A | 3/2006 |
| JP | 2007020829 A | 2/2007 |
| JP | 2007143880 A | 6/2007 |
| JP | 2007283103 A | 11/2007 |
| JP | 2008-23346 | 2/2008 |
| JP | 2008-136786 | 6/2008 |
| JP | 2008-520287 A | 6/2008 |
| JP | 2008521506 A | 6/2008 |
| JP | 4392470 B2 | 1/2010 |
| JP | 2010514506 A | 5/2010 |
| JP | 4481582 B2 | 6/2010 |
| WO | 8001754 | 9/1980 |
| WO | 8500292 | 1/1985 |
| WO | 8803815 | 6/1988 |
| WO | 9114232 | 9/1991 |
| WO | 9114233 | 9/1991 |
| WO | 9315658 | 8/1993 |
| WO | 9325141 | 12/1993 |
| WO | 9415664 | 7/1994 |
| WO | 9632975 A1 | 10/1996 |
| WO | 1997012550 A1 | 4/1997 |
| WO | 9820919 A1 | 5/1998 |
| WO | 9924095 A2 | 5/1999 |
| WO | 0061216 A1 | 10/2000 |
| WO | 2000064353 A2 | 11/2000 |
| WO | 02086821 A | 10/2002 |
| WO | 03015633 A1 | 2/2003 |
| WO | 03046795 A2 | 6/2003 |
| WO | 2004012787 A2 | 2/2004 |
| WO | 2005004038 A1 | 1/2005 |
| WO | 2005016165 A1 | 2/2005 |
| WO | 2006042093 A1 | 4/2006 |
| WO | 2006055813 A2 | 5/2006 |
| WO | 2006058280 A1 | 6/2006 |
| WO | 2007143682 A2 | 12/2007 |
| WO | 2008011401 A2 | 1/2008 |
| WO | 2008060629 A2 | 5/2008 |
| WO | 2008082937 A2 | 7/2008 |
| WO | 2008085421 A2 | 7/2008 |
| WO | 2009012023 A1 | 1/2009 |
| WO | 2009158212 A1 | 12/2009 |
| WO | 2010115165 A2 | 10/2010 |
| WO | 2011136218 | 11/2011 |

OTHER PUBLICATIONS

Search Report and Supplementary European Search Report for EP05849688 dated Mar. 21, 2014.

Non-Final Office Action dated Apr. 23, 2014, in U.S. Appl. No. 12/519,040, John F. Kalafut et al., filed Dec. 29, 2006.

Non-Final Office Action dated Jul. 15, 2014 in related U.S. Appl. No. 11/691,823.

Non-Final Office Action dated Jul. 14, 2014 in related U.S. Appl. No. 12/519,213.

Flegal, K.M., et al., "Prevalence and trends in obesity among US adults," JAMA, 2002, vol. 288, Issue 14, pp. 1-4, 1999-2000.

(56) References Cited

OTHER PUBLICATIONS

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484, May/Jun. 1999.
Fleischmann, D., "Contrast Medium Injection Technique," in: U. Joseph Schoepf: "Multidetector-Row CT of The Thorax," pp. 47-59, Jan. 22, 2004.
Fleischmann, D., "Present and Future Trends in Multiple Detector-Row CT Applications; CT Angiography", European Radiology, vol. 12, Issue 2, Supplement 2, Jul. 2002, pp. s11-s15.
Gardiner, G. A., et al., "Selective Coronary Angiography Using a Power Injector," AJR Am J Roentgenol., vol. 146, Issue 4, pp. 831-833, Apr. 1986.
Garrett, J. S., et al., "Measurement of cardiac output by cine computed tomography," The American Journal of Cardiology, vol. 56, Issue 10, pp. 657-661, 1985.
Gembicki, F.W., "Vector Optimization for Control with Performance and Parameter Sensitivity Indices," PhD Thesis, Case Western Reserve University, 1974.
Gentilini A., et al. "A new paradigm for the closed-loop intraoperative administration of analgesics in humans", IEEE Transactions on Biomedical Engineering, vol. 49, Issue 4, pp. 289-299, 2002.
Gerlowski L.E. and Jain R.K., "Physiologically Based Pharmacokinetic Modeling: Principles and Applications," Journal of Pharmaceutical Sciences, vol. 72, pp. 1104-1125, Oct. 1983.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, Nov. 2003.
Mark V/Mark V Plus Injector Operation Manual KMP 805P Rev. B. MEDRAD, Inc, 1990.
McClellan, J.H., "Parametric Signal Modeling," Chapter 1 in Advanced Topics in Signal Processing, Pentice-Hall, Englewood Cliffs, NJ, 1988.
McCullough. P.A. et al., "Contrast-Induced Nephropathy (ON) Consensus Working Panel: Executive Summary," Reviews in Cardiovascular Medicine, vol. 7, Issue 4, pp. 177-197, 2006.
MCT and MCT Plus Injection Systems Operation Manual KMP 810P, MEDRAD, Inc. 1991.
Neatpisarnvanit, C. and Boston, J.R., "Estimation of plasma insulin from plasma glucose", IEEE Transactions on Biomedical Engineering, vol. 49, Issue 11, pp. 1253-1259, 2002.
Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.
Non-Final Office Action dated Apr. 26, 2013, in U.S. Appl. No. 12/519,040, John F. Kalafut, filed Jun. 12, 2009.
Final Office Action dated Oct. 2, 2012, in U.S. Appl. No. 12/519,040, John F. Kalafut, filed Jun. 12, 2009.
Non-Final Office Action dated Dec. 12, 2008, in U.S. Appl. No. 11/691,823, John F. Kalafut et al., filed Mar. 27, 2007.
Final Office Action dated Oct. 1, 2009, in U.S. Appl. No. 11/691,823, John F. Kalafut et al., filed Mar. 27, 2007.
Final Office Action dated May 10, 2013, in U.S. Appl. No. 12/611,172, John F. Kalafut et al., filed Nov. 3, 2009.
Final Office Action dated Mar. 5, 2013, in U.S. Appl. No. 12/519,213, John F. Kalafut et al., filed Jun. 15, 2009.
Final Office Action dated Jun. 19, 2013, in U.S. Appl. No. 13/186,983, John F. Kalafut et al., filed Jul. 20, 2011.
Final Office Action dated Jun. 17, 2013, in U.S. Appl. No. 12/519,213, John F. Kalafut et al., filed Jun. 15, 2009.
EZ CHEM Brochure, E-Z-EM, Inc., Jul. 2007.
European Search Report dated Jun. 17, 1996 in European Patent Application No. 95202547.6.
European Search Report dated Jan. 30, 2003 in European Patent Application No. 02020247.9.
European Search Report dated Feb. 21, 2012 in European Patent Application No. 11001045.1.
Non-Final Office Action dated Nov. 5, 2012, in U.S. Appl. No. 13/186,983, John F. Kalafut et al., filed Jul. 20, 2011.
Non-Final Office Action dated Oct. 18, 2012, in U.S. Appl. No. 12/519,213, John F. Kalafut et al., filed Jun. 15, 2009.
Dawson, P. and M. Blomley, "The value of mathematical modelling in understanding contrast enhancement in CT with particular reference to the detection of hypovascular liver metastases," European Journal of Radiology, vol. 41, Issue 3, pp. 222-236, Mar. 2002.
Dardik, H. et al., "Remote Hydraulic Syringe Actuator," Arch. Surg., vol. 115, Issue 1, Jan. 1980.
Non-Final Office Action dated Sep. 17, 2012, in U.S. Appl. No. 12/611,172, John F. Kalafut et al., filed Nov. 3, 2009.
Coleman and Branch, "Optimization Toolbox for Use with MATLAB, User's Guide," T. Mathworks, Editor 2007.
Bae, K.T., et al., "Aortic and hepatic contrast medium enhancement at CT. Part I. Prediction with a computer model," Radiology, vol. 207, Issue 3, pp. 647-655, 1998.
Bae, K.T., et al., "Multiphasic Injection Method for Uniform Prolonged Vascular Enhancement at CT Angiography: Pharmacokinetic Analysis and Experimental Porcine Method," Radiology, vol. 216, pp. 872-880, 2000.
Bae, K.T., et al., "Peak contrast enhancement in CT and MR angiography: when does it occur and why? Pharmacokinetic study in a porcine model," Radiology, vol. 227, pp. 809-816, Jun. 2003.
Bae, K.T., et al., "Uniform vascular contrast enhancement and reduced contrast medium volume achieved by using exponentially decelerated contrast material injection method," Radiology, vol. 231, Issue 3, pp. 732-736, 2004.
Baker, A.B., and Sanders, J.E., "Fluid Mechanics Analysis of a Spring-Loaded Jet Injector," IEEE Transactions on Biomedical Engineering, vol. 46, No. 2, Feb. 1999.
Becker, C.R., et al., "Optimal contrast application for cardiac 4-detector-row computed tomography," Investigative Radiology, vol. 38, Issue 11, pp. 690-694, Nov. 2003.
Blomley, M.J.K. and Dawson, P., "Bolus Dynamics: Theoretical and Experimental Aspects," The Brit. J. of Radiology, 70, pp. 351-359, 1997.
Buckley, D.L., et al., "Measurement of single kidney function using dynamic contrast-enhanced MRI: comparison of two models in human subjects," Journal of Magnetic Resonance Imaging, vol. 24, Issue 5, pp. 117-123, Nov. 2006.
Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.
Cademartiri, F., et al., "Intravenous contrasts material administration at 16-detector row helical CT coronary angiography: test bolus versus bolus-tracking technique," Radiology, vol. 233, Issue 3, pp. 817-823, Dec. 2004.
Goldfarb, S., "Contrast-induced nephropathy: Risk factors, pathophysiology, and prevention," Applied Radiology (online supplement), pp. 5-16, Aug. 2005.
Goss, J. E., et al., "Power injection of contrast media during percutaneous transluminal coronary artery angioplasty," Catheterization and Cardiovascular Diagnosis, vol. 16, pp. 195-198 1989.
Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109, Feb. 1992.
Guyton, A.C., "Circulatory Physiology: cardiac output and regulation," Saunders, Philadelphia, pp. 173, ISBN: 07216436004, 1985.
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C, Regularization tools: a MATLAB package for analysis and solution of discrete ill-posed problems, Numerical Algorithms, vol. 6, Issue 1, pp. 35, 1994.

(56) References Cited

OTHER PUBLICATIONS

Hansen, P.C., "The truncated SVD as a method for regularization," BIT Numerical Mathematics, vol. 27, Issue 4, pp. 534-555, 1987.
Hansen, P.C., et al., "An adaptive pruning algorithm for the discrete L-curve criterion," Journal of Computational and Applied Mathematics, vol. 198, Issue 2, pp. 9, 2007.
Harris P., H. D. "The Human Pulmonary Circulation," Edinburgh, Churchill Livingstone, (Appendix I), 1986.
Krause, W., "Application of pharmacokinetics to computed tomography: injection rates and schemes: mono-, bi-, or multiphasic?," Investigative Radiology, vol. 31, Issue 2, pp. 91-100, Feb. 1996.
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, F.R., "Basic Principles of Phase-contrast, Time-of-flight, and Contrast-enhanced MR Angiography", pp. 1-10, 1999.
Koh, T.S., et al., "Assessment of Perfusion by Dynamic Contrast-Enhanced Imaging Using a Deconvolution Approach Based on Regression and Singular Value Decomposition," IEEE Transactions on Medical Imaging, vol. 23, Issue 12, pp. 1532-1542, Dec. 2004.
Kalafut, J.S., "A New Paradigm for the Personalized Delivery of Iodinated Contrast Material at Cardiothoracic, Computed Tomography Angiography," Doctoral Dissertation, University of Pittsburgh, 2010.
Østergaard, L., et al., "High resolution measurement of cerebral blood flow using intravascular tracer bolus passages. Part 1: Mathematical approach and statistical analysis," Magnetic Resonance in Medicine, vol. 36, Issue 5, pp. 715-725, 1996.
Østergaard, L., et al., "High resolution measurement of cerebral blood flow using intravascular tracer bolus passages. Part II: Experimental comparison and preliminary results," Magn Reson Med, vol. 36, Issue 5, pp. 726-736, 1996.
Parker, K.J. and Tuthill T.A., "A Particulate Contrast Agent With Potential for Ultrasound Imaging of Liver," Ultrasound in Medicine & Biology vol. 13, Issue 9, pp. 555-566, Sep. 1987.
PHYSBE a classic model of the human circulatory system available from The Math Works, Inc. of Natick, Massachusetts, accessed at www.mathworks.com/products/demos/simulink/physbe, May 31, 2005, pp. 11.
Hayes, M.H., "Statistical Digital Signal Processing and Modeling," New York, New York: Wiley and Sons, pp. 154-177, 1996.
Heiken, J.P. et al., "Dynamic Contrast-Enhanced CT of the Liver: Comparison of Contrast Medium Injection Rates and Uniphasic and Biphasic Injection Protocols," Radiology, vol. 187, No. 2, May 1993, pp. 327-331.
International Preliminary Report on Patentability and Written Opinion for International Patent Application No. PCT/US00/10842 dated May 22, 2001.
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice," Advance CT, A GE Healthcare Publication, Aug. 2004.
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Sung, C.K., et al. "Urine Attenuation Ratio: A Mew CT Indicator or Renal Artery Stenosis," AJR Am J Roentgenol, vol. 187, pp. 532-540, Aug. 2006.
Supplementary European Search Report dated Apr. 15, 2011 in European Patent Application No. 07867951.1.
Supplementary European Search Report dated Aug. 19, 2010 in European Patent Application No. 05852259.0.
Supplementary European Search Report dated Dec. 9, 1998 in European Patent Application No. EP 96936079.0.
Supplementary European Search Report dated Jul. 23, 2013 in European Patent Application No. 08771789.8.
Tyco Healthcare Group LP v. MEDRAD. Inc. Complaint, Case No. 1:06-cv-00763, Nov. 8, 2006.

Wada, D.R. and Ward, D.S., "Open loop control of multiple drug effects in anesthesia", IEEE Transactions on Biomedical Engineering, vol. 42, Issue 7, pp. 666-677, 1995.
Wada, D.R. and Ward, D.S., "The hybrid model: a new pharmacokinetic model for computer-controlled infusion pumps", IEEE Transactions on Biomedical Engineering, vol. 41, Issue 2, pp. 134-142, 1994.
Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.
International Preliminary Report on Patentability and Written Opinion for International Patent Application No. PCT/US2007/026194 dated Jun. 30, 2009.
International Preliminary Report on Patentability and Written Opinion for International Patent Application No. PCT/US2007/087765 dated Jun. 30, 2009.
International Preliminary Report on Patentability, International Search Report and Written Opinion for International Patent Application No. PCT/US2008/067982.
International Preliminary Report on Patentability and Written Opinion for International Patent Application No. PCT/US2009/047168 dated Jan. 5, 2011.
International Preliminary Report on Patentability and Written Opinion for International Patent Application No. PCT/US2011/041802 dated Dec. 28, 2012.
International Preliminary Report on Patentability and Wrtitten Opinion for International Patent Application No. PCT/US2005/042891 dated May 30, 2007.
International Preliminary Report on Patentability for International Application No. PCT/EP2005/007791, International Bureau of WIPO, Geneva, Switzerland, dated May 22, 2007.
International Preliminary Report on Patentability and International Search Report for International Patent Application No. PCT/US2005/041913.
International Search Report and Written Opinion for International Application No. PCT/US05/42891, ISA/US dated Sep. 25, 2006.
International Search Report for International Patent Application No. PCT/US00/10842 dated Jan. 23, 2001.
Krieger, R. A., C02-Power-Assisted Hand-Held Syringe: Better Visualization during Diagnostic and Interventional, vol. 19, Issue 2, pp. 123-128, Feb. 1990.
International Search Report for International Patent Application No. PCT/US2007/026194 dated Jun. 26, 2008.
International Search Report for International Patent Application No. PCT/US2007/087765 dated Jun. 12, 2008.
Liebel-Flarsheim Company, "Angiomat 6000 Digital Injection System—Operator's Manual", Document No. 600950, Rev. 1, 1990.
International Search Report for International Patent Application No. PCT/US2009/047168 dated Aug. 4, 2009.
International Search Report for International Patent Application No. PCT/US2011/041802 dated Jan. 5, 2012.
International Search Report for International Patent Application No. PCT/US96/15680 dated Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201, 1989.
iSTAT 1 System Manual, Abbott Laboratories, Rev. Aug. 14, 2006.
Jacobs, J.R., "Algorithm for optimal linear model-based control with application to pharmacokinetic model-driven drug delivery," IEEE Transactions on Biomedical Engineering, vol. 37, Issue I, pp. 107-109, 1990.
Jo, S.H., et al. "Renal Toxicity Evaluation and Comparison Between Visipaque (Iodixanol) and Hexabrix (Ioxaglate) in Patients With Renal Insufficiency Undergoing Coronary Angiography," Journal of the American College of Cardiology, vol. 48, Issue 5, pp. 924-930, 2006.
European Search Report and Opinion dated Nov. 21, 2013 from EP No. 13004902.6.
"Digital Injector for Angiography", Sias, (Sep. 7, 1993).
"Disposable Low-Cost Catheter Tip Sensor Measures Blood Pressure during Surgery," Sensor, Jul. 1989.
"Infus O.R. Multi-Drug Syringe Pump with Smart Labels", Bard MedSystems Division Inc., pp. 2693-2696, 2005.

(56) References Cited

OTHER PUBLICATIONS

"The Solution for Your IV Formulas," Valley Lab. Inc., E-39-15, 3399, 3400, 2646.
Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.
Angiography, Catheterization and Cardiovascular Diagnosis, vol. 19, pp. 123-128, 1990.
Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.
Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.
Gramovish V.V., et al. Quantitative estimation of myocardial perfusion in patients with chronic ischaemic heart disease using magnetic resonance imaging, Cardiology, 2004, p. 4-12, No. 89.
International Preliminary Report on Patentability from corresponding PCT Application No. PCT/US2012/037744, dated Nov. 27, 2014, filed May 14, 2012.
Supplementary European Search Report from dated Jul. 24, 2015 related EP Application No. EP12876629.
Baker, Aaron; et al. "Fluid Mechanics Analysis of a Spring-Loaded Jet Injector." IEEE Transactions on Biomedical Engineering, vol. 46, No. 2, Feb. 1899.
Bischoff, Bernhard, et al., Impact of a Reduced Tube Voltage on CT Angiography and RAdiation Dose:Results of the Protection I Study, JACC Cardiovascular Imaging, 2009, pp. 940-948, vol. 2 No. 8.
Buckley, D.L., et al., "Measurement of single kidney function using dynamic contrast-enhanced MRI: comparison of two models in human subjects," Journal of Magnetic Resonance Imaging, vol. 24, Issue 5, pp. 1117-1123 (Nov. 2006).
Dardik, H. et al., "Remote hydraulic syringe actuator: its use to avoid radiation exposure during intraoperative arteriography," Arch. Surg., vol. 115, Issue 1, pp. 105 (Jan. 1980).
"European Search Report dated Feb. 1, 2016 from EP15157102".
EZ CHEM Blood Analyzer System, E-Z-EM, Inc., product data from corporate website (www.ezem.com).
Farrelly, Cormac, et al., Low dose dual-source CT angiography of the thoracic aorta, Int J Cardiovasc Imaging,2010. DOI 10.1007/s10554-010-9742-9.
Final Office Actions dated Jun. 17, 2013 and Mar. 5, 2013, in U.S. Appl. No. 12/519,213, John F. Kalafut et al., filed Jun. 15, 2009.
Fraioli, Francesco, et al., Low-dose multidetector-row CT angiography of the infra-renal aorta and lowerextremity vessels: image quality and diagnostic accuracy in comparison with standard DSA, Eur Radiol. 2006, pp. 137-146. vol. 16.
Funama, Yoshinori, et al., Radiation Dose Reduction without Degradation of Low-Contrast Detectability atAbdominal Multisection CT with a Low-Tube Voltage Technique: Phantom Study. Radiology, Dec. 2005, pp. 905-910, vol. 237, No. 3.
Gembicki, Florian W., "Performance and Sensitivity Optimization: A Vector Index Approach", Department of Systems Engineering, Case Western Reserve University, Jan. 1974.
Gerlowski L. et al., Physiologically Based Pharmacokinetic Modeling: Principles and Applications, Journal of Pharmaceutical Sciences, pp. 1103-1106, 1124, vol. 72, No. 10.
Gerlowski L.E. and Jain R.K., "Physiologically Based Pharmacokinetic Modeling: Principles and Applications," Journal of Pharmaceutical Sciences, vol. 72, No. 10, pp. 1103-1127 (Oct. 1983).
Guytan, A.C., "Circuitry Physiology: cardiac output and regulation", Saunders, Philadelphia, p. 173, ISBN: 07216436004, 1973.
Hansen, P.C., "The truncated SVD as a method for regularization," BIT Numerical Mathematics, vol. 27, Issue 4, pp. 534-553 (1987).
Harris, P. and Heath, D. The Human Pulmonary Circulation: Its form and function in Health and Disease, 3rd Edition, Edinburgh, Churchill Livingstone, Appendix I (1986).
Hausleiter, Jorg, et al., Radiation Dose Estimates From Cardiac Multislice Computed Tomography in DailyPractice: Impact of Different Scanning Protocols on Effective Dose Estimates, Circulation Journal of the AmericanHeart Association, Mar. 14, 2006, pp. 1304-1310, vol. 113.
International Preliminary Examination Report and International Search Report for International Patent Application No. PCT/US00/10842 dated May 22, 2001.
International Preliminary Report on Patentability and International Search Report for International Patent Application No. PCT/US00/10842 dated May 22, 2001.
International Preliminary Report on Patentability and Written Opinion and International Search Report for International Patent Application No. PCT/US2008/067982 dated Jan. 19, 2010.
International Preliminary Report on Patentability International Search Report, and Written Opinion for International Patent Application No. PCT/US2007/026194 dated Jun. 30, 2009.
International Preliminary Report on Patentability International Search Report, and Written Opinion for International Patent Application No. PCT/US2007/087765 dated Jun. 30, 2009.
International Preliminary Report on Patentability International Search Report, and Written Opinion for International Patent Application No. PCT/US2009/047168 dated Jan. 5, 2011.
International Preliminary Report on Patentability, International Search Report and Written Opinion for International Patent Application No. PCT/US2011/041802 dated Dec. 28, 2012.
International Preliminary Report on Patentability, International Search Report, and Wrtitten Opinion for International Patent Application No. PCT/US2005/042891 dated May 30, 2007.
International Search Report and the Written Opinion of the International Searching Authority for application No. PCT/US2007/26194 dated Jun. 26, 2008.
International Search Report and Written Opinion for International Patent Application No. PCT/US2005/041913 dated May 24, 2006.
International Search Report and Written Opinion from counterpart PCT Application PCT/2008/67982 filed Jun. 24, 2008.
International Search Report for International Patent Application No. PCT1US20081067982 dated Oct. 8, 2008.
International Search Report for International Patent Application No. PCT/US2000/010842 dated Apr. 5, 2001.
i-STAT Analyzer System, Abbott Laboratories, product data from corporate website (www.abbottpointofcoare.com).
KalRA, Mannudeep, et al., Clinical Comparison of Standard Dose and 50% Reduced-Dose Abdominal CT: Effecton Image Quality, American Journal of Radiology, Nov. 2002, pp. 1101-1106. vol. 179.
Korosec, Frank, "Basic Principles of Phase-contrast, Time-of-flight, and Contrast-enhanced MR Angiography", 1999.
Leschka, Sebastian, et al., Low kilovoltage cardiac dual-source CT: attenuation, noise, and radiation dose, EurRadiol. 2008, pp. 1809-1817, vol. 18.
Liebel-Flarsheim company—Angiomat 6000 Digital Injection System Operator's Manual, 600950 Rev 1 (1990); p. 3-6 to 3-8, 4-52 to 4-56.
Liebel-Flarsheim company,Angiomat 6000 Digital Injection System Operator's Manual, 600950 Rev 1 (1990); pp. 1-1 to 9-6.
Marin, Daniele, et al., Low-Tube-Voltage, High-Tube-Current Multidetector Abdominal CT: Improved ImageQuality and Decreased Radiation Dose with Adaptive Statistical Iterative Reconstruction algorithm—Initial ClincalExperience, Radiology. Jan. 2010, pp. 145-153, vol. 254, No. 1.
Medrad, Mark V/Mark V Plus Injector Operation Manual,KMP 805P Rev. B (1990); pp. 1-18 to 1-28, 3-7 to 3-13, 14-1 to 14-4.
Nakayama, Yoshiharu, et al., Abdominal CT with Low Tube Voltage: Preliminary Observations about RadiationDose, Contrast Enhancement, Image Quality, and Noise, Radiology, Dec. 2005, pp. 945-951, vol. 237, No. 3.
Newton, Texas A&M University lecture slides, Statistics 626, 1999.
Non-Final Office Action dated Dec. 17, 2008, in U.S. Appl. No. 11/691,823, John F. Kalafut et al., filed Mar. 27, 2007.
Non-Final Office Action dated Feb. 15, 2012, in U.S. Appl. No. 12/519,040, John F. Kalafut, filed Jun. 12, 2009.

(56) References Cited

OTHER PUBLICATIONS

Non-Final Office Action dated Feb. 2, 2015, in U.S. Appl. No. 12/611,172.
Non-Final Office Action dated Jan. 3, 2014, in U.S. Appl. No. 11/691,823.
Non-Final office Action dated Mar. 12, 2013, in U.S. Appl. No. 13/655,525, John F. Kalafut et al., filed Oct. 19, 2012.
Non-Final Office Actions dated Apr. 26, 2013 and dated Feb. 15, 2012, in U.S. Appl. No. 12/519,040, John F. Kalafut, filed Jun. 12, 2009.
Office Action dated Apr. 23, 2014, in U.S. Appl. No. 12/519,040, John Kalafut, et al., filed Jun. 12, 2009.
"Supplementary Partial European Search Report", dated Nov. 10, 2016.
Alessio; et al, "Weight-Based, Low-Dose Pediatric Whole-Body PET/CT Protocols", Oct. 2009, 50, 10, 1570-1578.
"Extended European Search Report from EP Application No. 11798986", dated Feb. 24, 2017.
Non-Final Office Action dated Dec. 12, 2014, in U.S. Appl. No. 13/186,983.
Regression Analysis Tutorial, Econometrics Laboratory, University of California at Berkeley, Mar. 22-26, 1999, pp. 183-201.
Renalguard, PLC Medical Systems, Inc. News Release. (May 12, 2008).
"Renalguard," PLC Medical Systems, Inc. News Release, pp. 1-3 (May 12, 2008).
Renalguard, PLC Medical Systems, Inc., product data from corporate website (www.plcmed.com).
Sablayrolles, J-L, "Cardiac CT: Experience from Daily Practice," Advance CT, A GE Healthcare Publication, pp. 1-10 (Aug. 2004).
Suess, Christoph, et al, Dose optimization in pediatric CT: current technology and future innovations. PediatricRadiology, 2002, pp. 729-734. vol. 32.
The European Search Report from EP14174725.3 dated May 8, 2015.
Tyco's Complaint and Jury Demand, Civil Case No. 06-763, U.S.D.C. (S.D.Ohio), *Tyco Healthcare Group LP, Mallinckrodt Inc. and Liebel-Flarsheim Company* v. *MEDRAD, Inc.* (Nov. 7, 2006).
Waaijer, Annet, et al., Circle of Willis at CT Angiography: Dose Reduction and Image Quality—Reducing TubeVoltage and Increasing Tube Current Settings, Radiology, Mar. 2007, pp. 832-839, vol. 242, No. 3.
Wintersperger, B., et al., Aorto-iliac multidetector-row CT angiography with low kV settings: improved vesselenhancement and simultaneous reduction of radiation dose, Eur Radiol, 2005, pp. 334-341, vol. 15.

* cited by examiner

Fig. 1C

Test Bolus

| | Flow Rate | Volume | Duration |
|---|---|---|---|
| A | 5 | 20 | 00:04 |
| B | 5 | 40 | 00:08 |

| | ROI1 | ROI2 |
|---|---|---|
| | 8.7 | 15.5 |
| | 236 | 175 |

Enter time to peak of test inj. [sec]:
Enter the peak of test inj. [HU]:

Computer Protocol

Computed Parameters
Subject CO [L/min]: 5.67    Subject BV [L]: 0.475

Diagnostic Protocol
Suggested Scan Delay [sec]: 18

Please review values before entering into the injector

| | Flow Rate | Volume | Duration | Ratio |
|---|---|---|---|---|
| A | 3.5 | 55 | 00:16 | 40/60 |
| % | 3.5 | 26 | 00:08 | |
| B | 3.5 | 40 | 00:11 | |

210

Patient Parameters

64  Subject Height [in]
151 Subject Weight [lbs]
74  Subject Age [yrs]
74  Avg. heart rate [bpm]

○ Male  ● Female

Computed BMI: 25.9
Table CO [L/min]: 4.05

Max Flow Rate [ml/s]
5
6
7

Contrast Concentration [mgI/ml]
300
350
370

Catheter Gauge
18
20
22

Injection Site ACF:
○ Left  ● Right

Scan Parameters

5.24  Scan Duration [sec]

Desired Peak Enh [HU]
300
350

Target Enh [HU]
250
300

Enter    Clear/New    Save

Fluid Volumes to Load
Contrast Load Vol [ml]: 175    Saline Load Vol [ml]: 150

MODELING OF PHARMACEUTICAL PROPAGATION AND PARAMETER GENERATION FOR INJECTION PROTOCOLS

CROSS REFERENCE TO RELATED APPLICATION

This application is a 371 national phase application of PCT International Application No. PCT/US2011/041802, filed on Jun. 24, 2011, and designating the United States of America, which claims the benefit of U.S. Provisional Application Ser. No. 61/358,400, filed on Jun. 24, 2010, the contents of which are incorporated herein by reference.

BACKGROUND

The following information is provided to assist the reader to understand the technology described below and certain environments in which such technology can be used. The terms used herein are not intended to be limited to any particular narrow interpretation unless clearly stated otherwise in this document. References set forth herein may facilitate understanding of the technology or the background thereof. The disclosure of all references cited herein are incorporated by reference.

The administration of contrast medium (with, for example, a powered injector) for radiological exams typically starts with the clinician filling an empty, disposable syringe with a certain volume of contrast agent pharmaceutical. In other procedures, a syringe pre-filled with contrast agent is used. The clinician then determines a volumetric flow-rate and a volume of contrast to be administered to the patient to enable a diagnostic image. An injection of saline solution, having a volume and flow rate determined by the operator, often follows the administration of contrast agent into the veins or arteries. A number of currently available injectors allow for the operator to program a plurality of discrete phases of volumetric flow rates and volumes to deliver. For example, the SPECTRIS SOLARIS® and STELLANT® injectors available from Medrad, Inc. of Indianola, Pa., provide for entry of up to and including six discrete pairs or phases of volumetric flow rate and volume for delivery to a patient (for example, for contrast and/or saline). Such injectors and injector control protocols for use therewith are disclosed, for example, in U.S. Pat. No. 6,643,537 and Published U.S. Patent Application Publication No. 2004-0064041, the disclosures of which are incorporated herein by reference. The values or parameters within the fields for such phases are generally entered manually by the operator for each type of procedure and for each patient undergoing an injection/imaging procedure. Alternatively, earlier manually entered values of volume and flow rate can be stored and later recalled from the computer memory. However, the manner in which such parameters are to be determined for a specific procedure for a specific patient continues to undergo development.

In that regard, differences in contrast dosing requirements for different patients during imaging and other procedures have been recognized. For example, U.S. Pat. No. 5,840,026, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT (or MSCT) scanners, single phase injections are dominant over biphasic or other multiphasic injections in regions of the world where such fast scanners are used. Although using standard, fixed or predetermined protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines.

A few studies have attempted quantitative analyses of the injection process during CT angiography (CTA) to improve and predict arterial enhancement. For example, Bae and coworkers developed pharmacokinetic (PK) models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," *Radiology*, vol. 207, pp. 647-55 (1998); K. T. Bae, "Peak contrast enhancement in CT and MR angiography: when does it occur and why? Pharmacokinetic study in a porcine model," *Radiology*, vol. 227, pp. 809-16 (2003); K. T. Bae et al., "Multiphasic Injection Method for Uniform Prolonged Vascular Enhancement at CT Angiography: Pharmacokinetic Analysis and Experimental Porcine Method," *Radiology*, vol. 216, pp. 872-880 (2000); U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure. However, the injection profiles computed by inverse solution of the PK model are profiles not readily realizable by most CT power injectors without major modification.

In Bae's models, there is no consideration for implementation of the PK models in a controller framework. For example, when converting the differential equation system into a state-space form, the rank of the resulting state matrix is less than the order of the system because of the number of free parameters in the system formulation. This rank deficiency manifests itself as a singularity when attempting to invert the matrix and is problematic for digital representation of the system for prediction and control. Further, the Bae models do not address transport delays of the contrast material directly, but model the transport delay by introducing multiple, in series sub-compartments throughout the cardiopulmonary model. The multiple sub-compartments provide a propagation delay in the simulated output because the new phase response of the system is different (additive) due to the additional compartments. The introduction of the multiple compartments is somewhat arbitrary, albeit based on physical insight of the vascular system. For example, the lung compartment is divided into 30 sub-compartments because of the contrast bolus dispersion and delay through the cardiopulmonary system.

Wada and Ward, "The hybrid model: a new pharmacokinetic model for computer-controlled infusion pumps", IEEE Trans. Biomed Eng, vol. 41(2), pp. 134-142, 1994, the disclosure of which is incorporated herein by reference, derived a 3 compartment pharmacokinetic model similar to the approach taken by Bae and used that model in a control scheme in an attempt to regulate the plasma concentration of anesthetic (the upload alienating). They were attempting to model the recirculation effect of the agent through the blood stream, as well, which they modeled by inserting transport delays in their simulations. They were able to generate simulation with prediction errors under 5%.

Wada and Ward "Open loop control of multiple drug effects in anesthesia", IEEE Trans. Biomed Eng, vol. 42(7), pp. 666-677, 1995, the disclosure of which is incorporated herein by reference, also applied their pharmacokinetic (PK) model to control multiple effects of anesthetic drugs. Their control scheme requires an anesthesiologist to set the allowable side-effect levels (expressed as a plasma concentration).

In another approach, Fleischmann and coworkers treated the cardiovascular physiology and contrast kinetics as a "black box" and determined its impulse response by forcing the system with a short bolus of contrast (approximating a unit impulse). In that method, one performs a Fourier transform on the impulse response and manipulates this transfer function estimate to determine an estimate of a more optimal injection trajectory than practiced previously. D. Fleischmann and K. Hittmair, "Mathematical analysis of arterial enhancement and optimization of bolus geometry for CT angiography using the discrete Fourier transform," *J Comput Assist Tomogr*, vol. 23, pp. 474-84 (1999), the disclosure of which is incorporated herein by reference.

Uniphasic administration of contrast agent (typically, 100 to 150 mL of contrast at one flow rate) results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," *Radiology*, vol. 227, pp. 809-16 (2003), the disclosures of which are incorporated herein by reference. Fleischmann and Hittmair thus presented a scheme that attempted to adapt the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast.

Fleischmann proscribed that a small bolus injection, a test bolus injection, of contrast agent (16 ml of contrast at 4 ml/s) be injected prior to the diagnostic scan. A dynamic enhancement scan was made across a vessel of interest. The resulting processed scan data (test scan) was interpreted as the impulse response of the patient/contrast medium system. Fleischmann derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level) Fleischmann derived an input time signal by dividing the frequency domain representations of the desired output by that of the patient transfer function. Because the method of Fleischmann et. al. computes input signals that are not realizable in reality as a result of injection system limitations (for example, flow rate limitations), one must truncate and approximate the computed continuous time signal.

In addition to problems of control with current injector systems, many such systems lack convenience and flexibility in the manner in which the injector systems is operated.

In that regard, the complexity of medical injection procedures and the hectic pace in all facets of the health care industry place a premium on the time and skills of an operator.

In many current quantitative analysis techniques, clinical practicalities diminish the chances of adoption into regular use. Currently available physiological models can require the estimation of many physiologic parameters a priori (for example, cardiac output, organ and great vessel blood volumes, permeability factors). Further, models may not be well oriented towards per-patient adaptation based on test-bolus enhancement because of certain mathematical limitations.

SUMMARY

In one aspect, a method of modeling propagation of contrast medium (which includes a contrast enhancing agent for use in an imaging procedure) injected into a patient using a physiologically based pharmacokinetic model, includes: incorporating into the physiologically based pharmacokinetic model at least one of a non-linear saturation term in a peripheral venous compartment or at least one configurable transport delay term through at least one compartment. The physiologically based pharmacokinetic model can, for example, be adapted to model, predict or estimate a time enhancement curve for one or more regions of interest of the patient. In a number of embodiments, the physiologically based pharmacokinetic model is discretizable.

The at least one configurable transport delay can, for example, be configurable at least in part on the basis of at least one patient specific variable (for example, height, age, weight, gender, etc.).

The physiologically based pharmacokinetic model can, for example, be adapted to model propagation of contrast medium after injection of contrast medium has ceased. The model can, for example, predict, estimate or model volumetric flow rate of blood and the effect thereof on propagation of contrast medium. The physiologically based pharmacokinetic model can, for example, predict, estimate or model an effect on propagation of contrast medium upon injection of a fluid containing no contrast enhancing agent after injection of contrast medium. The fluid containing no contrast enhancing agent can, for example, include saline (for example, as in the case of a saline flush following an injection of contrast medium).

At least one parameter for the physiologically based pharmacokinetic model can, for example, be determined from data from multiple individuals. At least one parameter for the physiologically based pharmacokinetic model can, for example, be determined at least partially on the basis of at least one patient specific variable. At least one parameter for the physiologically based pharmacokinetic model can, for example, be determined at least in part on the basis of at least one time enhancement curve of the patient resulting from an injection of contrast medium. Time enhancement curves for more than one region of interest can be used in determining one or more parameters of the model.

The method can further include reducing the order of the physiologically based pharmacokinetic model. In a number of embodiments of a reduced order model, at least one parameter is determined at least in part on the basis of at least one time enhancement curve of the patient. Time enhancement curves for more than one region of interest can be used in determining one or more parameters of the model.

The physiologically based pharmacokinetic model can, for example, be incorporated in a system comprising an injector system and an imaging system. The model can, for example, be used in generating at least one parameter for an injection procedure.

In a number of embodiments, the method can further include using the physiologically based pharmacokinetic model to estimate a time enhancement curve for the patient and to determine at least one parameter of an injection procedure at least in part on the estimated time enhancement curve. The method can further include using a time enhancement curve during a diagnostic injection of contrast medium (for example, in a bolus tracking methodology) to update the model (for example, in a model predictive control methodology) and, for example, to alter at least one parameter of the injection procedure.

In another aspect, a method of modeling propagation of contrast medium injected into a patient using a physiologically based pharmacokinetic model includes: modeling volumetric flow rate of blood and the effect thereof on the propagation of contrast medium after injection of contrast medium ceases. The physiologically based pharmacokinetic model can, for example, predict, estimate or model an effect on propagation of contrast medium upon injection of a fluid containing no contrast enhancing agent after injection of contrast medium. The fluid containing no contrast enhancing agent can, for example, include saline. The physiologically based pharmacokinetic model can, for example, be discretizable.

The physiologically based pharmacokinetic model can, for example, be adapted to predict, estimate or model a time enhancement curve for one or more regions of interest of the patient.

The physiologically based pharmacokinetic model can, for example, include at least one non-linear saturation term in a peripheral venous compartment or at least one configurable transport delay term through at least one compartment. The at least one configurable transport delay can, for example, be configurable at least in part on the basis of at least one patient specific variable.

At least one parameter for the physiologically based pharmacokinetic model can, for example, be determined at least partially on the basis of data from multiple individuals. At least one parameter for the physiologically based pharmacokinetic model can, for example, be determined at least partially on the basis of at least one patient specific variable. At least one parameter for the physiologically based pharmacokinetic model can, for example, be determined at least in part on the basis of at least one time enhancement curve of the patient resulting from an injection of contrast medium.

The method can further including reducing the order of the physiologically based pharmacokinetic model (for example, eliminating or combining one or more parameters, compartments and/or subsystems). In a number of embodiments, at least one parameter for such a reduced order physiologically based pharmacokinetic model is determined at least in part on the basis of at least one time enhancement curve of the patient.

The physiologically based pharmacokinetic model can, for example, be incorporated in a system including an injector system and an imaging system (which can be separate, partially integrated or fully integrated). The model can, for example, be used in generating at least one parameter for an injection procedure.

In a number of embodiments, the physiologically based pharmacokinetic model is used to estimate a time enhancement curve for the patient and to determine at least one parameter of an injection procedure at least in part on the estimated time enhancement curve.

In a number of embodiments, the method further includes using a time enhancement curve during a diagnostic injection of contrast medium to update the model and to alter at least one parameter of the injection procedure.

Any of the models described herein can, for example, be included in a system (for example, including at least one processor and at least one memory system in communication with the at least one processor) as software, hardware or a combination thereof.

In another aspect, a system includes a parameter generation system to determine at least one parameter for an injection procedure (for example, a parameter of an injection protocol or an imaging system parameter), the parameter generator system includes a physiologically based pharmacokinetic model to model propagation of a contrast medium injected into a patient including at least one of a non-linear saturation term in a peripheral venous compartment, at least one configurable transport delay term through at least one compartment, or an adaptation to model volumetric flow rate of blood and an effect thereof on the propagation of contrast medium after injection of contrast medium ceases. The physiologically based pharmacokinetic model can, for example, be discretizable.

At least one parameter for the physiologically based pharmacokinetic model can, for example, be determined at least in part from at least one time enhancement curve of the patient. As with all models hereof, one or more parameters (including all parameters) can be determined at least in part from at least one time enhancement curve of the patient.

The order of the physiologically based pharmacokinetic model can, for example, be reduced. At least one parameter for such a reduced order model can, for example, be determined at least in part from at least one time enhancement curve of the patient.

The system can further include a non-parametric model to estimate, model or predict propagation of a contrast medium injected into a patient. The non-parametric model can, for example, be based at least in part upon at least one time enhancement curve for a region of interest of the patient. The non-parametric model can, for example, be based at least in part upon a truncated Singular Value Decomposition (tSVD) deconvolution technique.

The at least one parameter can, for example, be determined using an optimization method on the basis of the physiologically based pharmacokinetic model. The optimization method can, for example, be a constrained optimization method.

The at least one parameter can, for example, be determined using an optimization method on the basis of at least one of the physiologically based pharmacokinetic model or the non parametric model.

The models, methods and systems described herein can, for example, be used in connection with various contrast media for use in a number of radiological imaging procedures. Moreover, the models, methods and systems described herein can also be used in connection with pharmaceuticals that are not contrast media.

Benefits provided by various embodiments include, but are not limited to: more consistent enhancement for subsequent image processing, reduced contrast or fluid loading for some patients, increased contrast dose to achieve sufficient image contrast when needed, reduced chance of extravasation, reduced image artifacts, reduced number of retakes, all slices containing optimal image contrast, increased consistency among scans observing a progression of disease or treatment over time, and optionally faster imaging times.

The technology described herein, along with the attributes and attendant advantages thereof, will best be appreciated and understood in view of the following detailed description taken in conjunction with the accompanying drawings.

BRIEF DESCRIPTION OF THE DRAWINGS

FIG. 1C illustrates an embodiment of a control screen setting for patient parameters, scan parameters and parameters of an injection protocol.

DETAILED DESCRIPTION

Figure 1A:
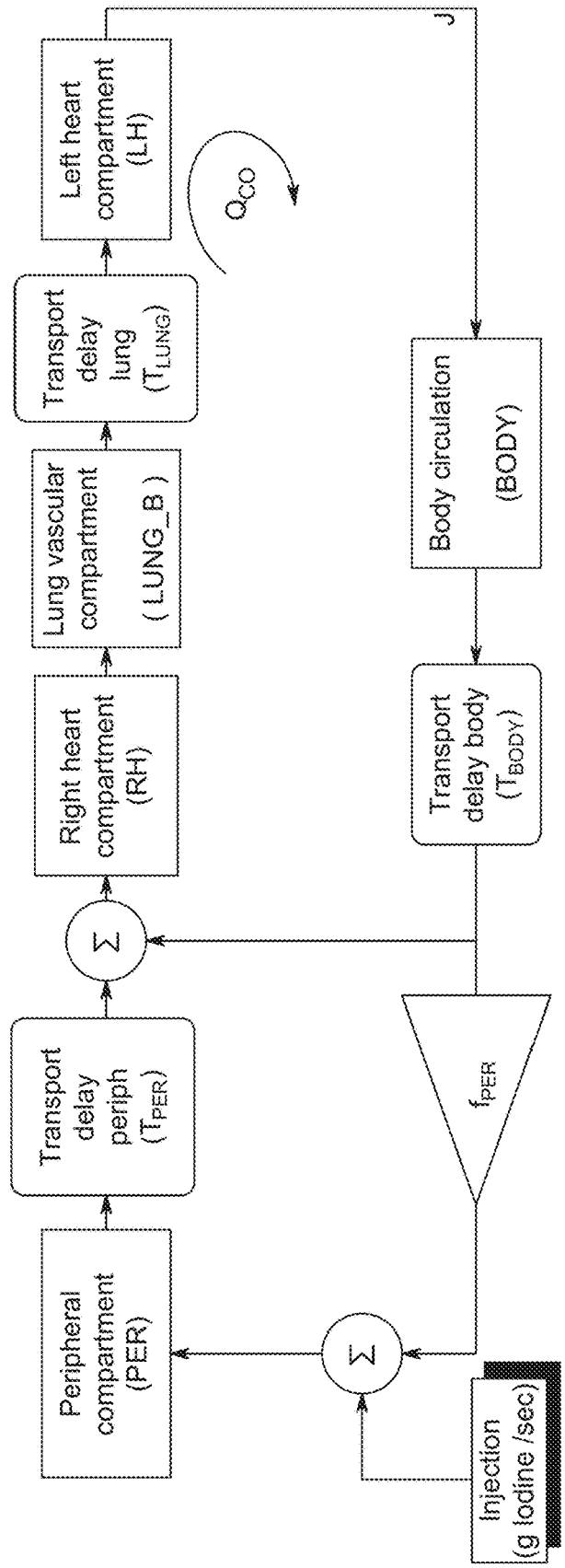
FIG. 1A illustrates an embodiment of a model structure of a new pharmacokinetic model (sometimes referred to herein as a hybrid model) describing propagation of a pharmaceutical such as a contrast medium.

As used herein and in the appended claims, the singular forms "a," "an", and "the" include plural references unless the content clearly dictates otherwise. Thus, for example, reference to "a parameter" includes a plurality of such parameters and equivalents thereof known to those skilled in the art, and so forth, and reference to "the parameter" is a reference to one or more such parameters and equivalents thereof known to those skilled in the art, and so forth.

In several representative embodiments, a physiologically based pharmacokinetic or PBPK modeling paradigm was used. In a number of embodiments, the PBPK models can, for example, be transformed into the discrete-time domain. Furthermore, a number of embodiments of the models provide for the explicit introduction of transport delays in the drug dynamics (that is, propagation time of, for example, contrast through the pulmonary vasculature). Distribution of drug in the vascular structures throughout the body can be described. Although the models described herein can be used in modeling the distribution of pharmaceuticals generally, in several representative embodiments, the subject for the models is CT angiography during the arterial phase of contrast distribution. Because the models described herein combine a number of modeling topologies, and include parameterization in a manner of the Bae contrast model, such models are referred to herein collectively as the "hybrid" model. As described above, however, unlike, for example, the Bae model, the hybrid model can be transformed into the discrete-time domain. Moreover, in addition to incorporating configurable transport delay terms into the model structure and a saturating non-linearity in the input (peripheral venous) compartment, a number of embodiments of the hybrid model provide for the simulation of injection phases of varying contrast agent concentration, including an injection phase or phases in which a fluid having little or no contrast enhancing agent is injected (for example, a diluent or saline injection phase, which is sometimes referred to as a flush or chaser phase following injection of a contrast). Previous physiological based pharmacokinetic models for propagation of, for example, a contrast medium do not model the effects of, for example, such a saline or other "flush" phase (which is commonly used, for example, during CTA imaging procedures) on in vivo contrast enhancement. The hybrid model hereof enables the modeling of, for example, contrast transport even after the injection of contrast has terminated because the volumetric flow rate of the blood in the peripheral compartment is increased by the volumetric flow rate of the contrast or a saline or other bolus including no contrast enhancing agent. Volumetric flow rate of blood and mass flow rate of contrast enhancing agent are treated independently. In a number of embodiments, the hybrid model includes a reduced number of states as compared to, for example, the full-body Bae model, while comparisons between the output of the hybrid model and the full-body Bae model are favorable. For example, lower prediction errors were measured by using the hybrid model. In certain cases, the hybrid model outperforms the Bae model when clinical data are used to compare the performance of both models.

In a number of embodiments, data-driven methods are used to predict or model pharmaceutical propagation using one or more contrast time enhancement curves (TECs) from, for example, a test injection of a contrast medium. In a number of embodiments, a model-based or parametric identification technique is used to identify one or more parameters for a PBPK model such as the hybrid model discussed above. In a number of such embodiments, a model reduction strategy was employed where the most relevant compartments of the hybrid model were considered during the first-pass of the contrast agent (for example, the peripheral venous compartment, the right heart compartment, the lung compartment and the left heart/aortic compartment). In the representative studies hereof, no attempt to fit all the parameters of the hybrid model was made, considering the limited length of data available from test bolus TECs. However, provided sufficient data, all parameters of the hybrid model can be identified.

Non-parametric or model independent identification techniques can also be used to generate a non-parametric estimate of pharmaceutical propagation. In several embodiments, a non-parametric estimate of the pharmaceutical/patient system was generated by solving an inverse problem using the truncated Singular Value Decomposition (tSVD) deconvolution technique.

Models described herein can be used not only to predict pharmaceutical (such as a contrast medium or material) pharmacokinetics in the human cardio-vascular system, but can provide systems and/or methods to generate or compute one or more parameters of an injection procedure (for example, one or more parameters of an injection protocol and/or of a scan) that achieves, for example, prospectively chosen enhancement targets for an individual patient and procedure, while using a reduced or minimal volume of contrast material.

For example, in a number of embodiments, data-driven contrast enhancement prediction methods as described above were used in protocol/parameters generation methods, systems or algorithms to successfully generate contrast enhancement profiles across a range of procedures and patient variables.

As used herein with respect to an injection procedure, the terms "injection protocol" or "protocol" refer to a group of injection variables or parameters such as flow rate, volume injected, injection duration, contrast agent concentration etc. that define, for example, the timing of, amount of, and/or the nature of fluid(s) to be delivered to a patient during an injection procedure. Such parameters can change over the course of the injection procedure. As used herein, the term "phase" refers generally to a group of parameters that define, for example, the timing of, amount of, and/or the nature of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

Scanner parameters that can be determined include, but are not limited to, the amount of radiation transmitted to the patient, power inputs (for example, voltage or current), timing (for example, scan start time, stop time, delay time and/or duration).

Figure 1B:
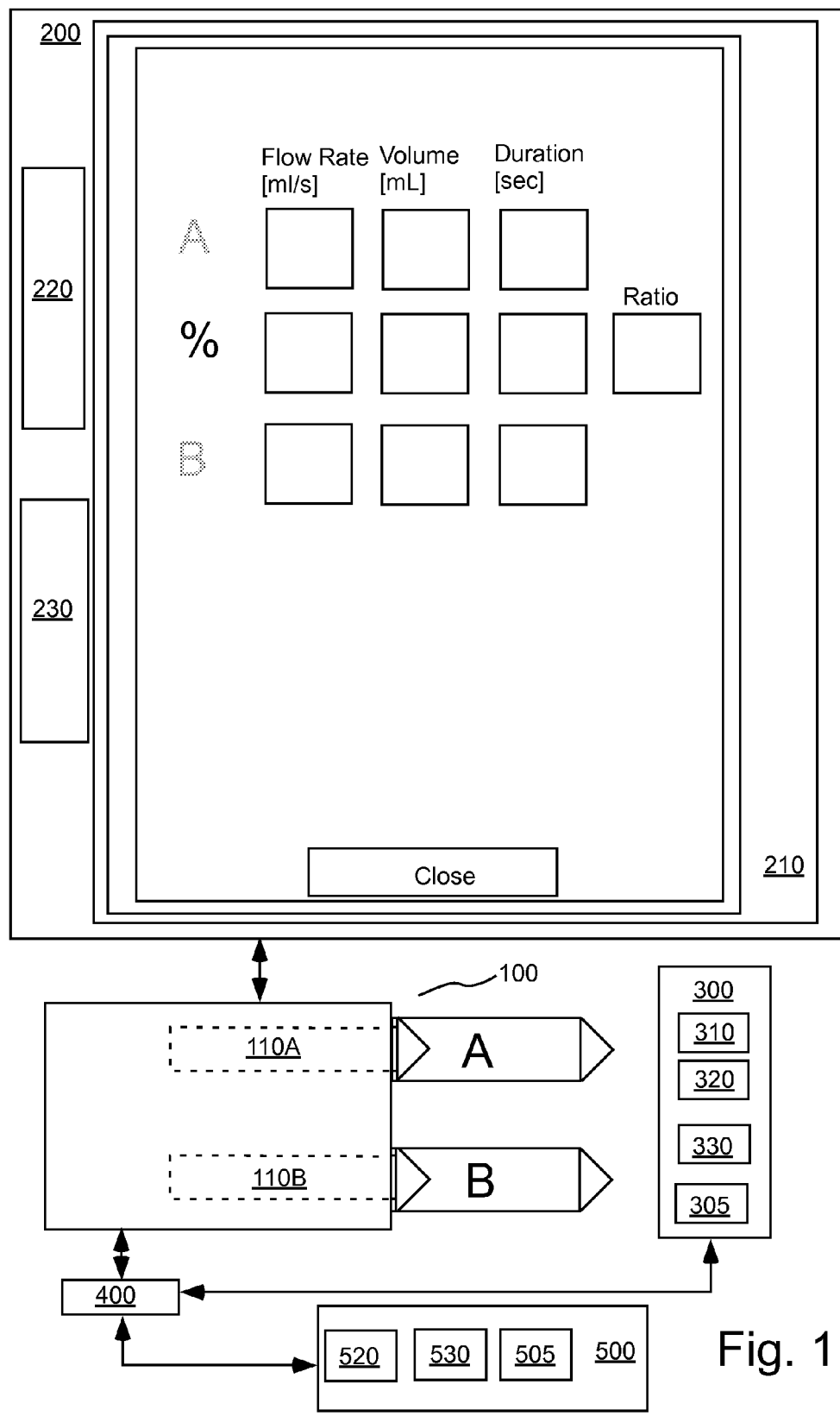
FIG. 1B illustrates an embodiment of an injection system.

In several embodiments, a system including a model as described herein can include an injection system including, for example, a dual syringe injector system 100 as illustrated in FIG. 1B. Dual syringe injector systems are, for example, disclosed in U.S. Pat. No. 6,643,537, Published U.S. Patent Application Publication No. 2004-0064041 and PCT International Patent Application No. PCT/US2007/026194). Injector system 100 can, for example, include two fluid delivery sources (sometimes referred to as source "A" and source "B" herein; such as syringes) that are operable to introduce a first fluid and/or a second fluid (for example, contrast enhancement fluid, saline etc.) to the patient independently (for example, simultaneously, simultaneously in different volumetric flow proportion to each other, or sequentially or subsequent to each other (that is, A then B, or B then A)). In the embodiment of FIG. 1B, source A is in operative connection with a pressurizing mechanism such as a drive member 110A, and source B is in operative connection with a pressurizing mechanism such as a drive member 110B. The injection system includes a control system 200 in operative connection with injector system 100 that is operable to control the operation of drive members 110A and 110B to control injection of fluid A (for example, contrast medium) from source A and injection of fluid B (for example, saline) from source B, respectively. Control system 200 can, for example, include or be in communication with a user interface comprising a display 210. In the illustrated embodiment of FIG. 1B, a portion of one embodiment of a screen display is illustrated which shows areas for parameters for injection flow rate, injection volume and injection duration for, for example, three phases of injection of fluid A and/or fluid B. The parameters for one or more such phases can be populated using the parameter generation systems and methods hereof. FIG. 1C illustrates another embodiment of a screen display.

A user can be provided with the option to adjust and/or override the protocol or parameters generated (for example, via a manual input system 205 including a keypad, keyboard, mouse etc. as known in the computer arts). Control system 200 can include a processor 220 (for example, a digital microprocessor as known in the art) in operative connection with a memory or memory system 230.

As clear to one skilled in the art, many injectors or fluid delivery systems, including multi-patient fluid delivery systems as, for example, disclosed in U.S. Pat. Nos. 7,326,186, 7,094,216, 6,866,654, 6,972,001, 6,699,219, 6,471,674, 6,306,117, 6,149,627, 6,063,052, 5,920,054, 5,843,037, 5,827,219, 5,739,508 and 5,569,181 are also suitable for use in connection with the models hereof.

Imaging system 300 can, for example, be a CT system, a Magnetic Resonance Imager (MRI) system, an ultrasound imaging system, or a Positron Emission Tomography (PET) system) or a Single Photon Emission Computed Tomography (SPECT) system as described above. Injector system can be in communicative connection with or partially or fully integrated with imaging system 300. Imaging system 300 and injector system 100 can, for example, be in communication connection via input/output ports (represented by terminations of arrows in FIG. 2B) as known in the art. In FIG. 1B, imaging system 300 and injector system 100 are, for example, illustrated to be in communicative connection via a common communication hub 400. Alternatively, a direct communication link can be established. Further data from one of imaging system 300 and injection systems 100 can be manually entered using one or more manual input systems (for example, keypads, keyboards mouse etc.) as known in the computer arts. Imaging system 300 and injector system or injector 100 can also be partially or fully integrated as described, for example, in Published PCT International Patent Application No. WO 2008/011401, the disclosure of which is incorporated herein by reference. One, a plurality of all the illustrated components of the injection system and imaging system 300 can also or alternatively be integrated with or incorporated within another, separate component that is placed in communicative connection with other system components.

Software and/or hardware embodying the systems and methods as described herein or any portion thereof can, for example, be embodied or incorporated within one or more components of the system (for example, within injector system 100 and/or within imaging system 300) or within one or more separate or standalone systems represented by system 500 which can, for example, include at least one processor (for example, a digital microprocessor), a memory system 520 a display 510 and a manual input system 505. In the embodiment illustrated in FIG. 1B, system 500 is shown to be in communicative connection with communication hub 400. As described above, a direct communication link can also be established. Further data from one or more systems can be manually entered into one or more other systems using one or more manual input systems (for example, keypads, keyboards, a mouse etc.) as known in the computer arts. Software embodying the systems and methods of the present invention (including, for example, one or more executable computer algorithms therefor) can, for example, be stored in memory 530 and executed by processor 520. As clear to one skilled in the art, all or a portion of the functionality of the modeling and/or parameter generating methods and/or systems can alternatively reside in an imaging system 300 (which can, for example, include at least one processor 320, a memory system 330, a display 310 and a manual input system 305) and/or in injector system 100.

In several representative embodiments, methods and systems described herein are used in connection with CT of the cardiothoracic vasculature. However, the methods and/or systems described herein for patient-specific, contrast enhancement CT of the cardiothoracic vasculature also have applicability to other anatomical regions of the body. In particular, peripheral arterial angiography of the leg arteries is challenging as a result of the acquisition speed of modern CT scanners. In many instances, the scanner must be slowed to account for the physiologic processes transporting the contrast bolus through the vasculature. Typically patients needing peripheral arterial CTA studies are also diabetic or have other renal insufficiencies and are potentially susceptible to kidney injury due to large volumes of contrast media. Therefore, computing a reduced or minimum volume of contrast dose in the patients as described herein can, for example, be desirable.

Methods and/or systems as described herein can also be used in neurological CT imaging. A short bolus of contrast, precisely and individually timed, is important for CTA of the brain arteries. It is important in these studies to synchronize the scan prior to contrast filling the veins of the head.

The methods and/or system described herein can also be used in predictive contrast enhancement scenarios in which a test bolus is not administered. Some radiologists prefer bolus tracking software over the test bolus methodology to synchronize the acquisition of the scan with the arrival of contrast. In these cases, the hybrid model (assuming the patient demographic data are available) could be used to determine, a priori, a contrast injection protocol to achieve desired targets in an iterative fashion. True hemodynamic status of the patient is not typically available when constructing the contrast protocol. Also, because of the transport delays in contrast propagation through the cardiopulmonary circuit, once the bolus is injected there is no "control" that can be exerted over the bolus for a particular patient.

Nonetheless, using the model in this open-loop approach is still superior to dosing without any consideration of the patient's habitus or physiology. Moreover, it is possible to use the hybrid model and the data collected during the scanner's bolus tracking acquisition in a Model Predictive Control framework.

Gadolinium-based (Gd) contrast agents are routinely delivered during MRI examinations to provide enhanced visualization of arterial and venous structures (MR Angiography). The methods and/or systems described herein can, for example, be used for MR (and other imaging applications), while, for example, recognizing that the relationship between signal intensity and blood-plasma concentration of, for example, Gd contrast agent is not linear as it is with CT contrast agents.

The Hybrid Model

Physiologically based pharmacokinetic modeling (PBPK), is a modeling approach that considers relevant physiology and function when determining the model structure. In a PBPK model, the body is separated into a number of interconnected compartments corresponding to anatomical regions. Each compartment is parameterized (volume, blood flow, perfusion) based on physiologic and anatomic considerations of the organism, and each connected by vascular compartments that facilitate the convective transport of the species to and away from the compartment. An advantage of this approach is the ability to scale the model across species without changing the structure of the model. The mathematical basis of the PBPK model is mass-conservation among the various compartments.

The compartments of an embodiment of a contrast media hybrid model hereof are shown in FIG. 1A. Each subsystem in the model represents an anatomical region of the body. Subsystems in a PBPK model are split into three compartments—the intracellular, extracellular and intravascular spaces. Contrast material does not enter the intracellular space and so it is ignored in a number of embodiments of PBPK models of contrast medium propagation.

The state variable, x, for several embodiments of the PBPK hybrid model is the mass of the contrast medium in a compartment ($x_i$). The volumetric flow rate of blood/contrast in an $i^{th}$ compartment is denoted by $Q_i$, and volumes are denoted by the variable $V_i$. The clearance of contrast medium from a subsystem, Cl, occurs via an irreversible process. Extraction of contrast medium occurs via glomerular filtration through the kidneys.

In embodiments wherein a model is intended for studying and predicting the distribution of contrast medium during CT angiography, quantifying the blood plasma concentration during the first-pass of the agent into the body is of primary concern and there is less interest in describing the absorption and distribution of the contrast material as it diffuses through systemic organs and parenchyma, with the exception of the lung subsystem. In such embodiments, the model need only consider the vascular compartments of the peripheral veins, the right and left heart, and the systemic circulation.

The mass "flux" (J) in or out of a compartment of the model is:

$$J_i = \frac{Q_i}{V_i} x_i \tag{1}$$

In equation 1, Q is the volumetric flow rate and V is the apparent volume of the compartment. The flow fractions, $f_{BODY}$, and $f_{PER}$ scale the cardiac output through the respective body segments. A summation of the flow fractions must equal the cardiac output, $Q_{CO}$: $f_{PER}Q_{CO}+f_{BODY}Q_{CO}=Q_{CO}$. For vascular compartments in this model, the apparent volume is the intravascular blood volume. Application of mass balance in the subsystems of the model results in the following global expression for the subsystems in FIG. 1A, Peripheral, Lung, Right Heart, Left Heart, and Body (i=1:5)

$$\dot{x}_i(t) = \left[\left(\frac{-Q_i + Q_{exog}}{V_i}\right)x_i(t) + k_{ji}x_j(t) - k_{ij}x_i(t)\right] + \tag{2}$$

$$1 \cdot \left(\left(\sum_{j=1}^{N} y_{i-j}(t)\right) + u_{exog}(t)\right)$$

$$y_i(t) = \frac{Q_i}{V_i} x_i$$

In equation 2, $u_{exog}(t)$ is the exogenous administration of contrast medium. It is non-zero only in the peripheral compartment and is defined by:

$$u_{exog}(t) \equiv C_{inj}(t) \cdot Q_{inj}(t) \tag{3}$$

because the administration flow rate, $Q_{inj}(t)$, or the concentration of the administered contrast agent, $C_{inj}(t)$, can be varied as a function of time. The product of volumetric flow rate and contrast concentration is termed the iodine administration rate.

Contrast agent is injected into a peripheral vein in the left or right arm of a human. The endogenous flow rate of blood draining through the peripheral veins in the arm ranges from 2-4 ml/s. It is probable that the high flow rate of contrast into the small peripheral veins entrains the blood flow and, thus, the injection rate is additive to the endogenous flow rate of blood in the peripheral vein. The flow rates typical with CTA examinations are greater than the endogenous flow rate of blood draining through the peripheral veins. The injection of contrast into the peripheral veins results in an additive contribution to the endogenous flow rate through the veins. Mathematically, the peripheral venous subsystem is a linear time-varying formulation of mass balance in the peripheral subsystem, then, due to the injection of the contrast:

$$\dot{x}_{PER}(t) = \frac{-(Q_{PER}(t))}{V_{PER}} x_{PER}(t) + u_{exog}(t) + y_{BODY}(t - T_{BODY}) f_{PER} \tag{4}$$

with $$Q_{PER}(t) = Q_{PER\_END} + Q_{inj}(t)$$

In equation 4, $Q_{PER\_END}$ is the endogenous flow rate of blood through the peripheral vein and $T_{BODY}$ is the transport delay of contrast recirculating through the entire body back through the peripheral veins. To avoid formulating a time-varying model for the entire model, equation 4 can be refactored considering that, after the injection, $Q_{PER}(t) = Q_{PER\_END}$, and that, during the injection, the flow rate is the sum of $Q_{PER\_END}+Q_{inj}$. The transport delays introduced by the circulatory system are denoted by $T_{PER}$ and $T_{BODY}$ and represent the output delays of the contrast agent from the peripheral and body subsystems. The time delays can be constants or functions of the volume and flow rate of blood in the respective systems. Details concerning the time delays are discussed further below. In the subsequent development, $T_{inj}$ represents the duration of the contrast injection. Under these assumptions, the peripheral subsystem dynamics may be expressed in standard LTI, state-space formulation as:

$$\left.\begin{aligned}\dot{x}_{PER}(t) &= \frac{-(Q_{PER\_END} + Q_{inj})}{V_{PER}} x_{PER}(t) + \\ &u_{exog}(t - T_{PER}) + y_{BODY}(t - T_{BODY}) \cdot f_{PER} \\ y_{PER}(t) &= \frac{Q_{PER\_END} + Q_{inj}}{V} x_{PER}(t)\end{aligned}\right\} \text{ for } t \leq T_{inj} \tag{5}$$

$$\left.\begin{aligned}\dot{x}_{PER}(t) &= \frac{-(Q_{PER\_END})}{V_{PER}} x_{PER}(t) + \\ &u_{exog}(t - T_{PER}) + y_{BODY}(t - T_{BODY}) \cdot f_{PER} \\ y_{PER}(t) &= \frac{Q_{PER\_END}}{V} x_{PER}(t)\end{aligned}\right\} \text{ for } t > T_{inj}$$

In equation 5, $y_{PER}(t)$ is the mass flux (units gI/s) of contrast exiting the peripheral subsystem. The concentration in the peripheral subsystem is $x_{PER}(t)$ divided by the blood volume in the peripheral veins.

The general solution to equation 4 is:

$$x_{PER}(t) = \int_0^t u_{exog}(\tau) e^{V_{PER} \int_0^t \frac{1}{Q_{PER}(\tau)} d\tau} d\tau e^{\int_0^t \frac{-V_{PER}}{Q_{PER}(\tau)} d\tau} \tag{6}$$

A saturating behavior affects the injection flow rate into the peripheral compartment. Empirical evidence suggests that injections greater than 8-10 ml/s saturate because of the compliant nature of the peripheral veins or because of reflux of contrast through the right atrium into the Inferior Vena Cava. A generalized description of the peripheral compartment dynamics, therefore is:

$$\dot{x}_{PER}(t) = \frac{-(Q_{PER})(t)}{V_{PER}} x_{PER}(t) + u_{exog}(Q_{inj}, t - T_{PER}) + y_{BODY}(t) f_{PER} \tag{7}$$

-continued
$$y_{PER}(t) = \frac{Q_{PER}(t)}{V_{PER}(t)} x_{PER}(t)$$

where the non-linear exogenous input function is:

$$u_{exog}(Q_{inj},t)=Q_{inj}(t) \cdot C_{inj}(t) \quad Q_{inj}(t) \le 8 \text{ [ml/s]}$$
$$u_{exog}(Q_{inj},t)=8 \cdot C_{inj}(t) \quad Q_{inj}(t) > 8 \text{ [ml/s]} \quad (8)$$

The conservation of mass applied to the Right Heart subsystem in FIG. 1 is:

$$\dot{x}_{RH}(t) = \frac{-(Q_{CO})}{V_{RH}} x_{RH}(t) + y_{PER}(t - T_{PER}) + y_{BODY}(t - T_{BODY}) \quad (9)$$

$$y_{RH}(t) = \frac{(Q_{CO})}{V_{RH}} x_{RH}(t)$$

The lung subsystem differs from the pure vascular subsystems in that the role of permeability between the capillary bed and the lungs is modeled. Consideration of the tissue compartment is made for completeness and for embodiments in which the effect of recirculation and accumulation of contrast in tissue will be of interest.

$$\dot{x}_{LUNG}(t) = \begin{pmatrix} \frac{-Q_{CO}}{V_{LUNG\_B}} & -k_{LUNG\_BT} \\ k_{LUNG\_BT} & -(k_{LUNG\_TB} + CL_{LUNG\_T}) \end{pmatrix} x_{LUNG}(t) + y_{RH}(t) \quad (10)$$

$$y_{LUNG}(t) = \left[ \frac{Q_{CO}}{V_{LUNG\_B}} \right] x_{LUNG}(t)$$

In equation 10, $Q_{CO}$ is the cardiac output, $K_{LUNG\_BT}$ is the rate transfer coefficient of contrast from the blood compartment into the tissue compartment, $k_{LUNG\_TB}$ is the rate transfer coefficient from the tissue compartment back into the blood compartment, and $CL_{LUNG\_T}$ represents an irreversible clearance term out of the tissue compartment.

The delay of contrast through the pulmonary vasculature is modeled as an input delay term in the dynamics of the Left Heart subsystem:

$$\dot{x}_{LH}(t) = \frac{-(Q_{CO})}{V_{LH}} x_{LH}(t) + y_{LUNG}(t - T_{LUNG}) \quad (11)$$

$$y_{LH}(t) = \frac{(Q_{CO})}{V_{LH}} x_{LH}(t)$$

and $y_{LUNG}(t)$ is the mass flux of contrast exiting the Lung subsystem. $T_{LUNG}$ is the delay time of the bolus travelling through the pulmonary vasculature. It can be a scalar constant or a function of the cardiac output and blood volume in the lung.

First-pass distribution and propagation of the contrast bolus is of significant interest for CT angiography applications. Because the organs, muscle, and fat compartments affect the distribution of the contrast after several recirculation times, they are not considered in several embodiments. Others have combined the systemic circulation into one, large vascular compartment, and systemic circulation is modeled in that fashion in a number of embodiments.

$$\dot{x}_{BODY}(t) = \frac{-(Q_{CO})}{V_{BODY}} x_{LH}(t) + y_{LH}(t) \quad (12)$$

$$y_{BODY}(t) = \frac{Q_{CO}}{V_{BODY}} x_{BODY}(t)$$

A unified formulation of the model, combining equations 4 through 12 can be set forth to ease implementation in numerical simulations. For notational convenience and to ensure that transport delays only appear as input and output delays, an augmented state vector comprised of state variables for each of the sections of the model is defined. The Right Heart, Lung and Left Heart subsystems are combined into a Cardiopulmonary (CP) state vector:

$$x_{Aug}=[x_{PER} x_{CP} x_{BODY}] \quad (13)$$

where the Cardiopulmonary (CP) state vector consists of the Right Heart, Lung and Left Heart state variables:

$$x_{CP}[x_{RH} x_{LUNG} x_{LH}] \quad (14)$$

The total system is expressed as:

$$\dot{x}_{PER}=A_{PER}x_{PER}+B_{PER}u_{PER}$$

$$y_{PER}(t)=C_{PER}x_{PER}(t)$$

$$\dot{x}_{CP}=A_{CP}x_{CP}+B_{CP}(y_{PER}(t)+y_{BODY}(t-T_{BODY}))$$

$$y_{CP}(t)=C_{CP}x_{CP}(t)$$

$$\dot{x}_{BODY}=A_{BODY}x_{BODY}+B_{BODY}y_{CP}(t-T_{LUNG})$$

$$y_{CP}(t)=C_{BODY}x_{BODY} \quad (15)$$

The input vector to the peripheral subsystem is composed of the exogenous contrast media injection through a peripheral vein and the recirculated contrast from the body subsystem:

$$u_{PER}=[(\varphi(u_{exog}(t-T_{PER}))y_{BODY}(t-T_{BODY})f_{PER}] \quad (16)$$

The blood-plasma concentration of the contrast in the body subsystem is scaled by a flow fraction, $f_{PER}$. The scalar function, $\varphi(u_{exog})$ in equation 16 defines the saturating non-linearity behavior of the venous system between the injection site and the right heart described in equation 8.

$$\varphi(u_{exog}) = \begin{cases} u_{exog}(Q_{inj}, t) = Q_{inj}(t) \cdot C_{inj}(t) & Q_{inj}(t) \le 8[\text{ml/s}] \\ u_{exog}(Q_{inj}, t) = 8 \cdot C_{inj}(t) & Q_{inj}(t) > 8[\text{ml/s}] \end{cases} \quad (17)$$

The state matrices are:

$$A_{PER} = \frac{-Q_{PER}(t)}{V_{PER}} \quad (18)$$

$$A_{CP} = \begin{bmatrix} \frac{-Q_{CO}}{V_{RH}} & 0 & 0 & 0 \\ \frac{Q_{CO}}{V_{RH}} & \frac{-Q_{CO}}{V_{LUNG\_B}} & -k_{LUNG\_BT} & 0 \\ 0 & k_{LTB} & -(k_{LUNG\_TB} + Cl_{LT}) & 0 \\ 0 & \frac{Q_{CO}}{V_{LUNG\_B}} & 0 & \frac{-Q_{CO}}{V_{LH}} \end{bmatrix} \quad (19)$$

$$A_{BODY} = \frac{-Q_{CO}}{V_{BODY}} \quad (20)$$

where the time varying flow through the peripheral circulation, $Q_{PER}(t)$ is defined in equation 4. The control matrices (B's) are:

$$B_{PER} = [1 \ 1]^T \quad (21)$$

$$B_{CP} = [1 \ 0 \ 0 \ 0]^T \quad (22)$$

$$B_{BODY} = [1] \quad (23)$$

$$C_{PER} = \left[\frac{Q_{PER}(t)}{V_{PER}}\right] \quad (24)$$

$$C_{CP} = \left[0 \ 0 \ 0 \ \frac{Q_{CO}}{V_{LH}}\right] \quad (25)$$

$$C_{BODY} = \left[\frac{Q_{CO}}{V_{BODY}}\right] \quad (26)$$

Figure 2:
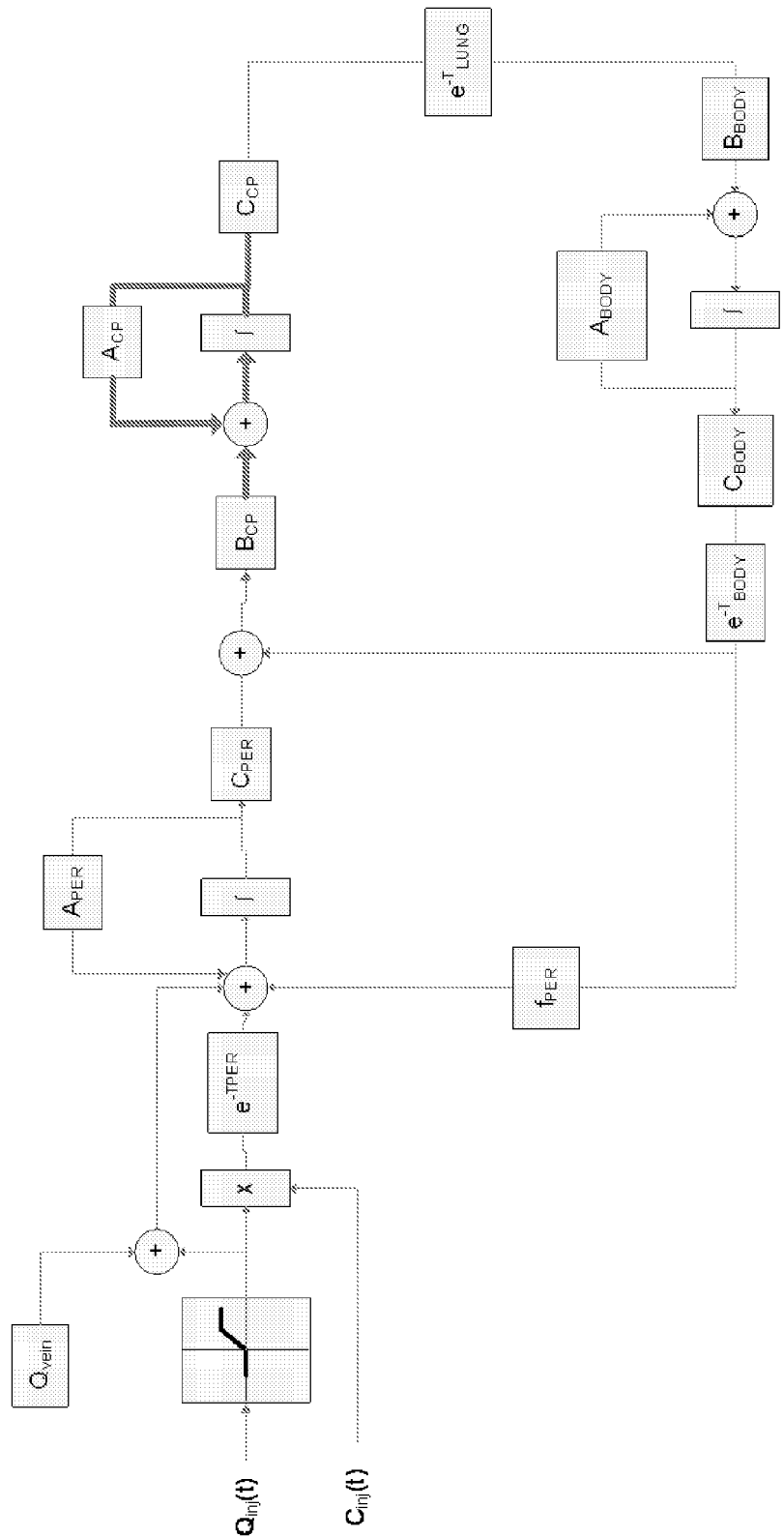
FIG. 2 illustrates an embodiment of an all-integrator view of the physiologic based pharmacokinetic model wherein the thick lines in the "CP" section denotes vector quantities, and the matrix values in are those defined in equations 18 through 26 set forth below.

An embodiment of an all-integrator view of the model is displayed in FIG. 2.

In choosing model parameter values for numerical simulations, a balance between fidelity and reasonable realizability can be made. It can be difficult to deduce parameter values for each sub-compartment which match the true, physiological parameters for an individual. In a number of embodiments, standard, physiologic "look up" tables and relationships determined via regression analyses on population data were used to determine one or more parameters. Any number of relationships can, for example, be used to determine one or more parameters. As discussed below, various PBPK model identification methods using test bolus enhancement data from patients can also be used to determine parameters. In a number of simulation studies, parameter values based solely on demographic data (height, weight, sex, age) and procedure specific values such as flow rate, volume and concentration of the contrast material were used.

Regression formulae, corrected for age, can be used to estimate cardiac output and blood volume as set forth in Guyton, A., *Circulatory physiology:cardiac output and its regulation.* 1963, Philadelphia Pa.: Saunders. In a number of embodiments, that cardiac output estimation is used here and provides the cardiac output estimation when the model is simulated. The estimator is:

$$C\hat{O}(h,w,a) = 36.36 \cdot h^{0.725} \cdot w^{0.425}(1 - 0.005(a-30)) \quad (27)$$

where the parameters h, w, and a are height [inches], weight [lbs] and age [years]. Estimation of or measurement of cardiac output is also discussed in US. Published Patent Application No. 2010/0030073. The central blood volume estimator in the model is, likewise, derived from a published regression formula and is a function of height, weight, and sex. The estimated blood volume for males is:

$$B\hat{V}(h,w) = 33.164 \cdot h^{0.725} \cdot w^{0.425} - 1229 \quad (28)$$

and for females:

$$B\hat{V}(h,w) = 34.850 \cdot h^{0.725} \cdot w^{0.425} - 1954 \quad (29)$$

The regional blood volume parameters throughout the model equals the total blood volume estimated by equation 28 or equation 29. The volumetric flow rate of blood through each sub-compartment, except for the peripheral, is the cardiac output computed by equation 27. Blood volumes in the different sub-systems can, for example, be set according to the relationships set forth in Bae, K. T., J. P. Heiken, and J. A. Brink, *Aortic and hepatic contrast medium enhancement at CT. Part I. Prediction with a computer model.* Radiology, 1998. 207(3): p. 647-55. Instead of setting the Left Heart blood volume to 3.6% of the total blood volume as by Bae et al., however, an additional 100 ml of blood is added in several embodiments of the PBPK model here to include the ascending aorta in the computations. In a number of embodiments, the procedure for configuring the blood volumes for a given subject is to compute an estimate of cardiac output and blood volume using height, weight, age and sex. The regional blood volumes are then computed using the relationships in Table 1.

TABLE 1

Regional blood volume parameters used in the novel model simulation

| Parameter | Value [Units] |
|---|---|
| $V_{PER}$ | .08 * BV(h, w, sex) [ml] |
| $V_{RH}$ | .036 * BV(h, w, sex) [ml] |
| $V_{LB}$ | .088 * BV(h, w, sex) [ml] |
| $V_{LH}$ | .056 * BV(h, w, sex) [ml] |
| $V_{SYS}$ | .848 * BV(h, w, sex) [ml] |

Additional model parameters include the rate transfer coefficients between the lung, blood and tissue compartments and contrast clearance from the central blood compartment. Because extraction of contrast material from the blood supply and tissue compartments occurs minutes after bolus injection, clearance terms ($C_{LUNG\_T}$) can be set to zero. Likewise, on the first pass of contrast material, there is little passage of contrast material through the pulmonary capillary bed, and subsequent accumulation into the tissue is minimal. The pulmonary transfer rate constants can therefore be set to zero.

The final parameters considered are the contrast bolus propagation delays through the peripheral venous circulation ($T_{PER}$), the propagation time through the pulmonary system ($T_{LUNG}$), and the recirculation delay of a bolus throughout the entire circulatory system ($T_{BODY}$).

In a number of embodiments, the system recirculation delay is held constant at, for example, 30 seconds. Consideration of one or more per-patient or patient specific variables or values, however, is made for the other two propagation delays. $T_{PER}$ is a function of the blood volume in the peripheral venous sub-system and the sum of injection rate and endogenous venous flow. Likewise, the propagation delay through the pulmonary compartment is a function of the pulmonary blood volume and the estimated cardiac output for each subject. The system recirculation delay can also be made to depend upon one or more patient specific variables. In several embodiments, an assumption of plug-flow is made for the $T_{PER}$ and $T_{LUNG}$ delays. A depiction of the transit delays used in the model is given in Table 2.

TABLE 2

Transit delay parameters

| Parameter | Value [Units] |
|---|---|
| $T_{PER}$ | $\dfrac{\left(\dfrac{V_{PER}}{2}\right)}{(Q_{vein} + Q_{Inj})}$ [sec] |
| $T_{LUNG}$ | $\dfrac{V_{LUNG\_B}}{Q_{CO}}$ [sec] |
| $T_{BODY}$ | 15 [sec] |

Performance of the model as a function of various parameters and inputs is presented below and compared to predictions by the Bae model (both published and resulting from an implementation of the model in Simulink). The new model's ability to predict contrast enhancement in a human data set is described and also compared to Bae model predictions.

In a number of simulation studies, injection parameters and model parameters were varied to demonstrate the model's ability to mimic known behaviors of contrast dynamics. Simulations demonstrating the model's ability to reproduce the effect of varied cardiac output on contrast enhancement were conducted. The saturating behavior of contrast enhancement as injection rates increase was demonstrated via simulation of the model as were the effects of saline flush after the contrast medium injection.

Figure 3:
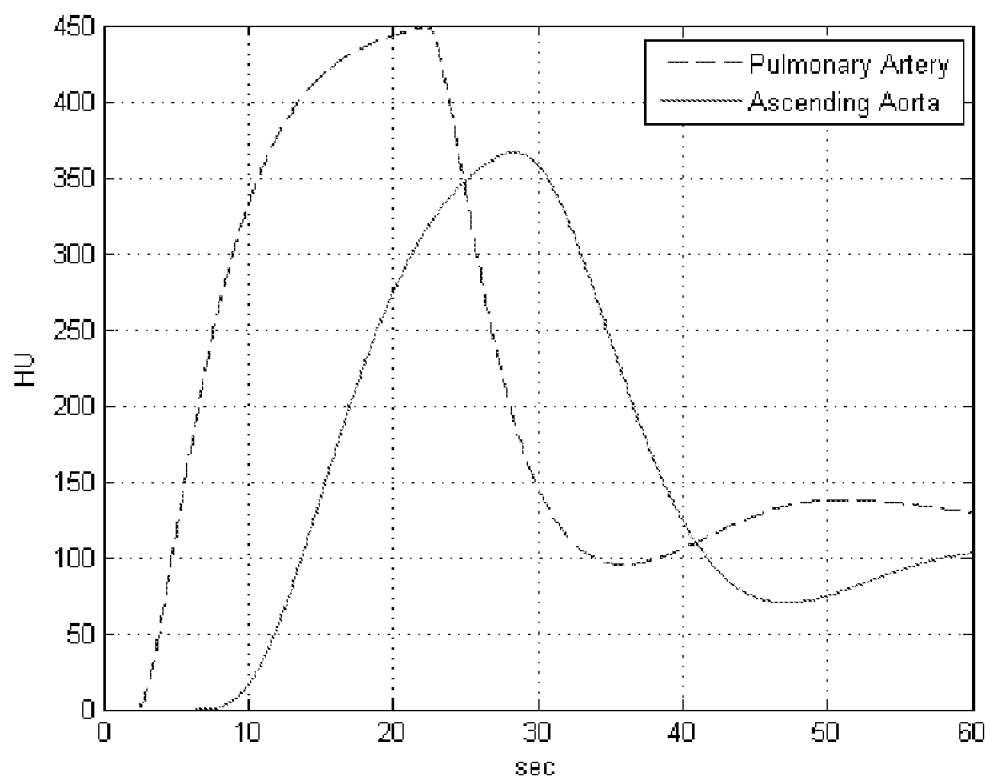
FIG. 3 illustrates simulated contrast enhancements for a normal subject.

FIG. 3 presents simulated contrast enhancement in the pulmonary artery and ascending aorta for a virtual patient with nominal attributes. The model was implemented and simulated in MATLAB (R2008b). The patient parameters for this example were, weight=170 lbs, height=68 in, sex=Male, age=35 years. Using equation 27, the estimated cardiac output was 6.60 L/min. The contrast injection protocol consisted of contrast with 370 mgI/ml concentration contrast agent, injected at a volumetric flow rate ($Q_{inj}(t)$) of 5 ml/s for 20 seconds (volume=100 ml). A 30 ml volume of saline was injected at 5 ml/s for 6 seconds. Note the enhancement in the ascending aorta peaks 5-6 seconds after maximum enhancement in the pulmonary artery as expected. Likewise, the enhancement level in the ascending aorta compartment is ~100 HU below that in the pulmonary artery as expected because the bolus was diluted between the pulmonary trunk and the ascending aorta. One can appreciate the systemic recirculation of the contrast material by noting the secondary contrast enhancement peak in the pulmonary artery at 50 seconds and the appearance in the ascending aorta of a secondary peak near 60 seconds.

Another experiment was conducted in which a series of simulations were conducted. For one simulated patient, contrast injection parameters were held constant across the set to demonstrate the model's ability to replicate the influence of cardiac output on contrast enhancement. The injection parameters were: 370 mgI/ml concentration contrast injected at 5 ml/s for 10 seconds (volume=50 ml) followed by a saline flush phase of 30 ml at 5 ml/s. The cardiac output of the virtual patient was adjusted from a low value (3 L/min) to a high value (8 L/min) in 1 L/min increments. This experiment assumed that the cardiac output can be manipulated independently of the blood volume. The blood volume for the virtual patient was held constant for each of the cardiac output values (using the same parameters as in the previous experiment: a 170 lb, 68 inch, 35 year old male). A shorter injection duration than in the previous example was used to avoid any recirculation phenomena at the low cardiac output values.

Figure 4:
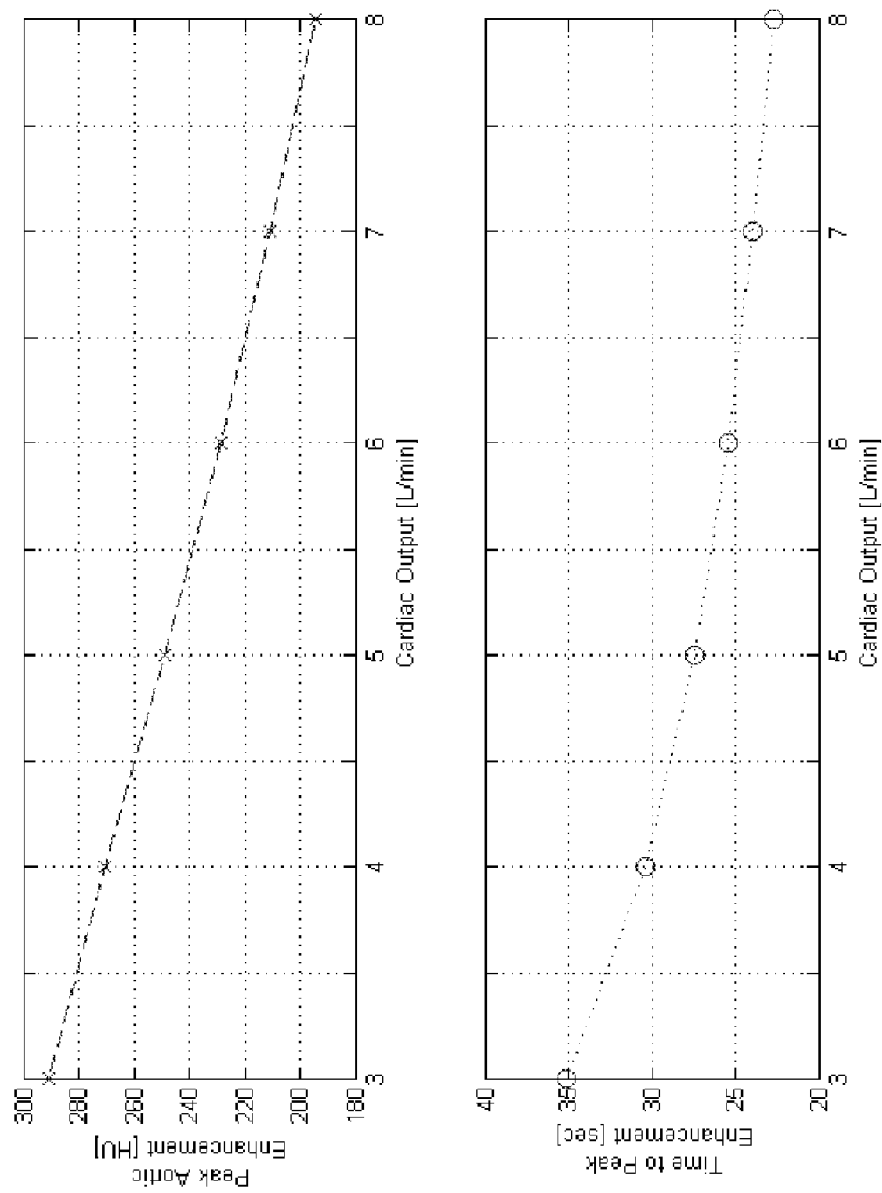
FIG. 4 illustrates simulated peak aortic enhancements and times to peak aortic enhancement plotted as functions of cardiac output in the hybrid model.

The peak contrast enhancement level in the ascending aorta and the time of maximum contrast enhancement were recorded and are graphically presented in FIG. 4. We expect to find that as the cardiac output increases, the arrival time of the contrast bolus in a vascular territory decreases. Likewise, as the cardiac output increases, we expect the contrast enhancement in the vascular structure to decrease as demonstrated theoretically and empirically in previous studies.

Figure 5:
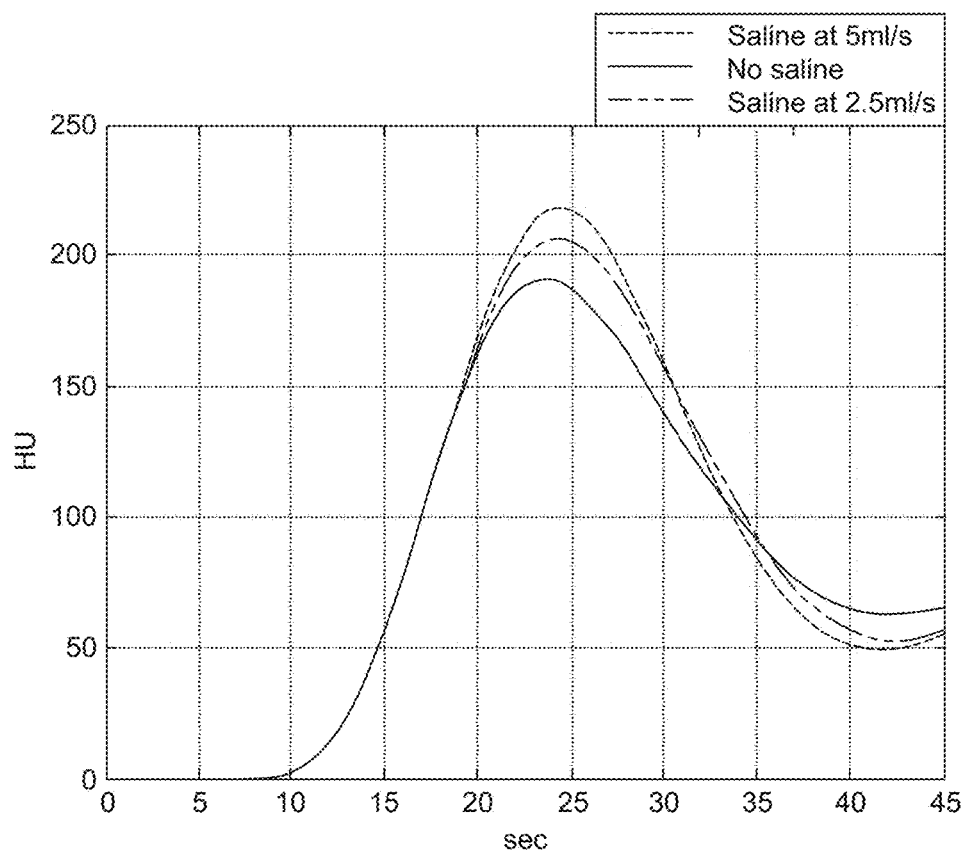
FIG. 5 illustrates simulation results demonstrating the model's ability to simulate the effect of saline flush injections.

The hybrid model was also simulated in MATLAB/Simulink using a virtual, 35 year old male, 68 inches tall and weighing 170 lbs. Three different injection protocols were used in this set of simulations—5 ml/s of 370 mgI/ml contrast for 10 seconds (volume=50 ml), followed by a saline chaser at 5 ml/s over 6 seconds (volume=30 ml), a saline chaser at a flow rate of 2.5 ml/s over 6 seconds (volume=15 ml), or no saline chaser. The resulting time enhancement curves are shown in FIG. 5. The simulations demonstrated a 14% increase in peak aortic enhancement for the protocol in which a saline flush was injected at the same flow rate of the contrast bolus. The time to peak enhancement was also delayed by 0.8 seconds. For the injection in which the saline was injected at half the flow rate of the contrast bolus, the increase in peak enhancement was 7% greater than when no saline flush was administered. The peak enhancement time was offset by 0.6 seconds. These results cannot be replicated with the Bae models, because the Bae models are not formulated to allow consideration of the effects of a saline chaser or diluent flush phase after the administration of the contrast bolus. The results demonstrated qualitative agreement of the model response with results demonstrated by others in animal models and humans.

As described above, the hybrid PBPK model results were compared to results from the Bae models. Aggregate data from a test cohort published in Bae, K. T., J. P. Heiken, and J. A. Brink, *Aortic and hepatic contrast medium enhancement at CT. Part I. Prediction with a computer model.* Radiology, 1998. 207(3): p. 647-55 facilitated the performance comparison. The patients were enrolled into three groups based on contrast injection protocol. There were three contrast protocols used in the study: a biphasic low-flow rate protocol, a uniphasic low-flow rate protocol, and a uniphasic high-flow rate protocol. A saline flush phase was not used in any of the groups of that study.

The data from the uniphasic, high-flow rate cohort were used for evaluating the new model. In that group, the mean body weight of the 27 subjects was 177 lbs and the range of values was 44.1 to 135.0 lbs. The contrast protocol consisted of injecting 320 mgI/ml contrast at 5.0 ml/s for 25 seconds (volume=125 ml). No data were reported regarding the heights, sex or age composition of the cohort but the authors use an average height of 68 inches and male sex when simulating their model. Single level scanning was performed on each of the subjects at the mid-abdominal aorta every 15 seconds for 120 seconds, and then once every 60 seconds up to 300 seconds. TECs were created by the investigators after placing a 1 cm$^2$ ROI on the abdominal aorta at the celiac axis and another one on the liver parenchyma.

The hybrid PBPK model was executed in MATLAB/Simulink. Because the empirical results were collected to 300 seconds, the contrast has sufficient time to recirculate through the vascular system. Clearance terms were added into the model to ensure adequate downslope/recirculation dynamics in the time enhancement curves or TECs. A typical Glomelular Filtration Rate (GFR) was set in the simulation of the Bae model (nominally 50-70 ml/min) as a clearance term set to 19% of the blood's volumetric flow-rate in the simulated renal artery.

A number of embodiments of the hybrid model do not contain a kidney compartment and the mechanism to mimic clearance in such embodiments can, for example, be through the lung compartment. In the simulation comparing the published Bae empirical data, a blood-tissue transfer coefficient ($k_{LUNG\_BT}$) of 0.08 sec$^{-1}$ and a compartment clearance value ($CL_{LUNG\_T}$) of 0.1 sec was used to approximate a 60 ml/min clearance rate because no meaningful physiologic process for this problem has a time scale shorter than 1 second. Too short a time step results in an inefficient simulation because excess time is taken to deliver equivalent results as one would obtain with a longer time step. Simulations conducted at times steps of 0.01 and 0.001 revealed no difference in predicted enhancements.

Figure 6:
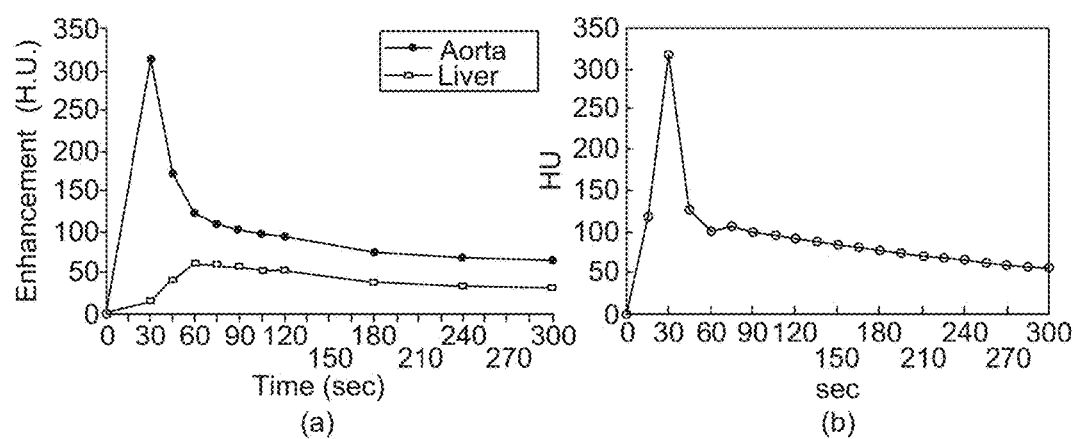
FIGS. 6A and 6B illustrate comparison of data reported by Bae et al. to the hybrid model output. (a) FIG. 6a in Bae et al. from the patient group using a 5 ml/s injection (b) predicted output from the new model in the abdominal aorta using the same contrast protocol and patient demographics as for the data in the empirical study.

The results of the hybrid model simulation using the aggregate patient data from the Bae study are shown in FIG. 6 next to the results from the aggregate enhancement data. The simulation of the model was performed with a fixed-step solver (Runge-Kutta) and a step-time of 0.1 seconds. The enhancement data were down-sampled for a better visual comparison to the empirical data.

The average peak enhancement of the high-flow rate group in Bae, K. T., J. P. Heiken, and J. A. Brink, *Aortic and hepatic contrast medium enhancement at CT. Part I. Prediction with a computer model*. Radiology, 1998. 207(3): p. 647-55 was reported as 313.7 HU and the new model generated an aortic enhancement curve with a peak enhancement of 317.3 HU, a percent difference of 1.15%. The Bae full-body model generated an enhancement curve with a peak enhancement of 321.3 HU, a percent difference of 2.42%. The time to peak enhancement predicted by the model was 31 seconds, the time to peak enhancement predicted by the Bae full-body model was 31 seconds, and the empirical data had an average peak enhancement time of 32 seconds.

The validation results presented in Bae, K. T., J. P. Heiken, and J. A. Brink, *Aortic and hepatic contrast medium enhancement at CT. Part I. Prediction with a computer model*. Radiology, 1998. 207(3): p. 647-55 did not assess the model's utility in simulating individual contrast enhancement profiles. To determine the ability of the Bae full-body model and the PBPK model hereof to predict individual contrast enhancement profiles, simulation results are presented using individual patient attributes (height, weight, age, sex) from subjects in a CTA imaging clinical trial to parameterize both models. The corresponding enhancement profiles (data extracted from the clinical images) from those patients' imaging data were then used to compare the outputs of the two models.

Three metrics were used to evaluate the predictive ability of both models—the Root Mean Square Error (RMSE), the Percent Difference in Maximum Enhancement (PDME), and a metric described in Bae, K. T., J. P. Heiken, and J. A. Brink, *Aortic and hepatic contrast medium enhancement at CT. Part I. Prediction with a computer model*. Radiology, 1998. 207(3): p. 647-55 as the "Enhancement Difference Index (EDI)" (the sum of the difference between the simulated and empiric enhancement curves, obtained from the clinical imaging data set, divided by the empirical data's area under the curve:

$$EDI = \frac{\sum_{i=1}^{N} |AUC_{Sim} - AUC_{Emp}|}{AUC_{Emp}} \quad (30)$$

where the subscripts "Sim" and "Emp" stand for the simulated response data and the empiric data respectively.

A CT angiography study data set was used to compare the performance of the hybrid model and the Bae full body model. The study's objective was to evaluate a patient-specific, optimized contrast delivery algorithm using features of timing bolus scans at the level of the pulmonary trunk. 70 subjects undergoing routine coronary CTA (cCTA) were enrolled in the study, but data from 20 of the total were used in the comparison tests presented here because test bolus enhancement data and descending aorta data could only be obtained for this number due to incomplete axial CT data set storage and transfer.

The demographics of the 20 subjects used in this analysis are summarized in Table 3. The average weight in this sample was average for adults in the United States (as set forth in Regal, K. M., et al., *Prevalance and trends in obesity among US adults*, 1999-2000. JAMA, 2002. 288: p. 4) and the average age is representative of the population typically indicated for cCTA.

TABLE 2

Summary demographic data Mean data are presented with standard deviations.

| Parameter | mean | min | max | median |
|---|---|---|---|---|
| Weight [lbs] | 196.7 +/− 57.3 | 110 | 290 | 184 |
| Height [in] | 68.1 +/− 44.3 | 61 | 76 | 68 |
| Age [yrs] | 60.1 +/ 10.2 | 37 | 74 | 60.5 |
| Heart Rate [bpm] | 65.6 +/− 8.47 | 50 | 81 | 64.5 |
| Freq. Male | 11 | | | |

All subjects in the study were scanned with a Dual Source CT scanner (Definition DS, Siemens Medical, and Malvern Pa.) using standard scan parameters. All subjects were administered a 20 ml test bolus of 300 mgI/ml contrast material followed by a 30 ml saline flush at a flow rate of 5 ml/s. The timing bolus scan was started approximately (variation arises from the scanner software) 5 seconds after the start of contrast injection, and single-level scans were acquired every 2 seconds until approximately 5 seconds after the peak enhancement in the ascending aorta. The scanner operator used discretion in stopping the data acquisition to reduce undue radiation exposure to the subject and a consistent length of acquisition data was not obtained.

TECs were created by the scanner software based on regions of interest or ROIs drawn in the pulmonary trunk and ascending aorta by the scanner operator. The times to peak and peak enhancements in those two areas were used by the investigational software to compute a patient-specific contrast flow rate, volume, contrast/saline admixture, and a personalized scan delay for the diagnostic CT scan. Summary procedure specific results are presented in Table 3 and Table 4. Many factors influence the scan duration of a CTA examination including scanner settings, patient heart rate, and the length of anatomy being imaged. The scan delay in this data set was computed by the investigational software described in Published PCT Application No. WO 2009/012023.

The contrast protocol computed by the investigational software consisted of 3 phases—a contrast only portion, a contrast and saline admixture phase, and finally a saline only "flush" phase. The volume reported in Table 4 for phase 2 refers to the volume of contrast in the phase while the phase 3 volume is the amount of saline delivered in the flush. Because the contrast was diluted in phase 2, the concentration reported in Table 4 is not the concentration of the stock solution (300 mgI/ml).

TABLE 3

Relevant scan parameters from the clinical data set, first 20 subjects. Mean values are given with standard deviations.

| Parameter | mean | min | max | median |
|---|---|---|---|---|
| Scan Duration [sec] | 10.3 +/− 2.59 | 4.3 | 16 | 18 |
| Scan Delay [sec] | 18 +/− 3.9 | 11.2 | 27 | 18 |

TABLE 4

Summary contrast protocol statistics from the clinical data set, first 20 subjects. Values are mean +/− standard deviation.

|  | Flow Rate [ml/s] | Volume [ml] | Concentration [mgI/ml] |
|---|---|---|---|
| Phase 1 | 4.18 +/− .88 | 74 +/− 12.7 | 300 |
| Phase 2 | 4.18 +/− .88 | 3.01 +/− 3.72 | 69 +/− 65.4 |
| Phase 3 | 4.18 +/− .88 | 30 | 0 |

Figure 7:
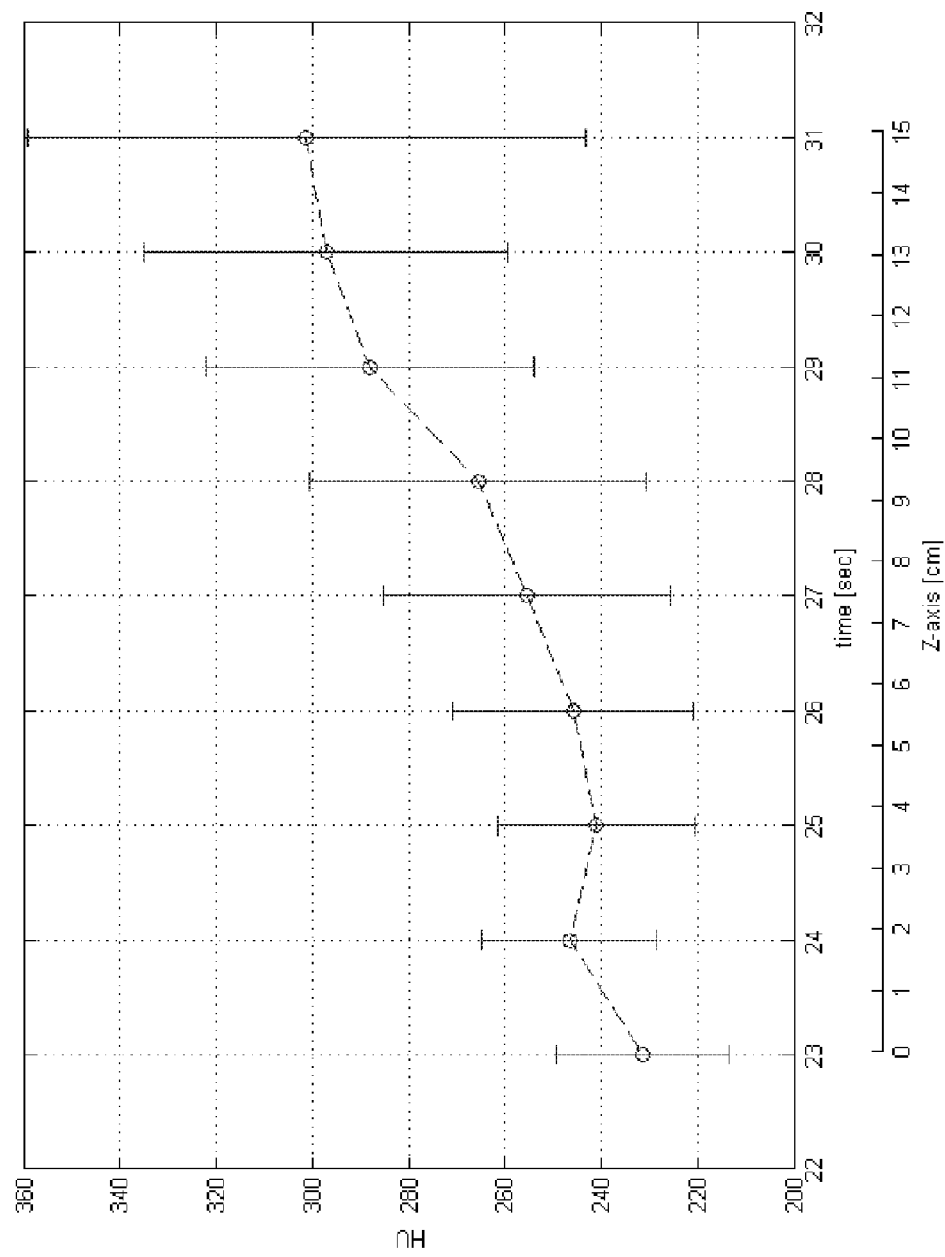
FIG. 7 illustrates one subject's (subject 1's) contrast enhancement profile extracted from the descending aorta. Error bars indicate the standard deviation of contrast enhancement at each measurement location.

A semi-automated segmentation software tool was used to extract time enhancement data from the 20 subject imaging sets (the helical imaging data are from the diagnostic scans). Each axial CT image was separated by 0.375 mm. The time between blocks of acquisition data varied between 0.75 and 1 second. An example data set is presented (subject 1) in FIG. 7. The scan delay for this particular acquisition was 23 seconds and thus the time axis begins at 23 seconds. Because the enhancement data are a function of time and space, the corresponding spatial dimension across the data set is superimposed on the figure's x-axis. Because the PK models generate predictions with respect to time in discrete "compartments", the comparisons employed here are with the temporal view of the image data extracted from the aortas of the 20 subjects.

To determine the relationship between HU value and blood-plasma concentration of the contrast material, an experiment with diluted amounts of contrast material was performed on the scanner used prior to the clinical study. Diluted contrast material was placed into radio-opaque containers and scanner using the same parameters used during the clinical trial. The conversion factor between HU and mgI/ml was computed, by linear regression, to be 27.1 HU/(mgI/ml). This constant was used in the hybrid model and Bae model simulations to convert the plasma concentration of iodine to HU.

To provide a comparison of the hybrid model against the Bae model using the clinical imaging data, an implementation of the Bae full-body PK model was made in MATLAB/Simulink. The parameters for the model described in Bae, K. T., J. P. Heiken, and J. A. Brink, *Aortic and hepatic contrast medium enhancement at CT. Part I. Prediction with a computer model*. Radiology, 1998. 207(3): p. 647-55 and further elaborated in U.S. Pat. No. 5,583,902 were used in configuring the model. A fixed-time step solver (Runge-Kutta) executed the model every 0.1 seconds. Individual subject demographic data (height, weight, sex, and age) were computed using equations 27, 28 and 29 were used to compute the cardiac output and total central blood volume estimates for each simulated subject. Because the Bae model, as published, does not allow for modeling a saline flush phase, the contrast protocols used in simulating the model only included contrast. The conversion factor of 27.1 HU/(mgI/ml) was used in converting blood-plasma concentrations to HU values.

The hybrid model was simulated using the parameters and methods presented in section 4.1.2. As with the Bae model, subject demographic data and the relationships defined in equations 27, 28 and 29 provided the values for cardiac output and blood volume. The parameter values in Tables 1 through 3 were used to configure the model. MATLAB/Simulink (R2008b) was used to simulate the model for each patient using the clinical data for patient parameters and the diagnostic phase contrast injection protocol, including the saline flush phase. As with the Bae model, the conversion factor of 27.1 HU/(mgI/ml) converted plasma concentrations to HU values.

Predicted HU values for each subject were downsampled to match the temporal resolution of the enhancement curves from the imaging data (1 sec/sample). Only the portions of the predicted enhancement curves spanning the time segment of the imaging data were used in computing the comparison metrics (MSE, PDME, EDI).

Figure 8:
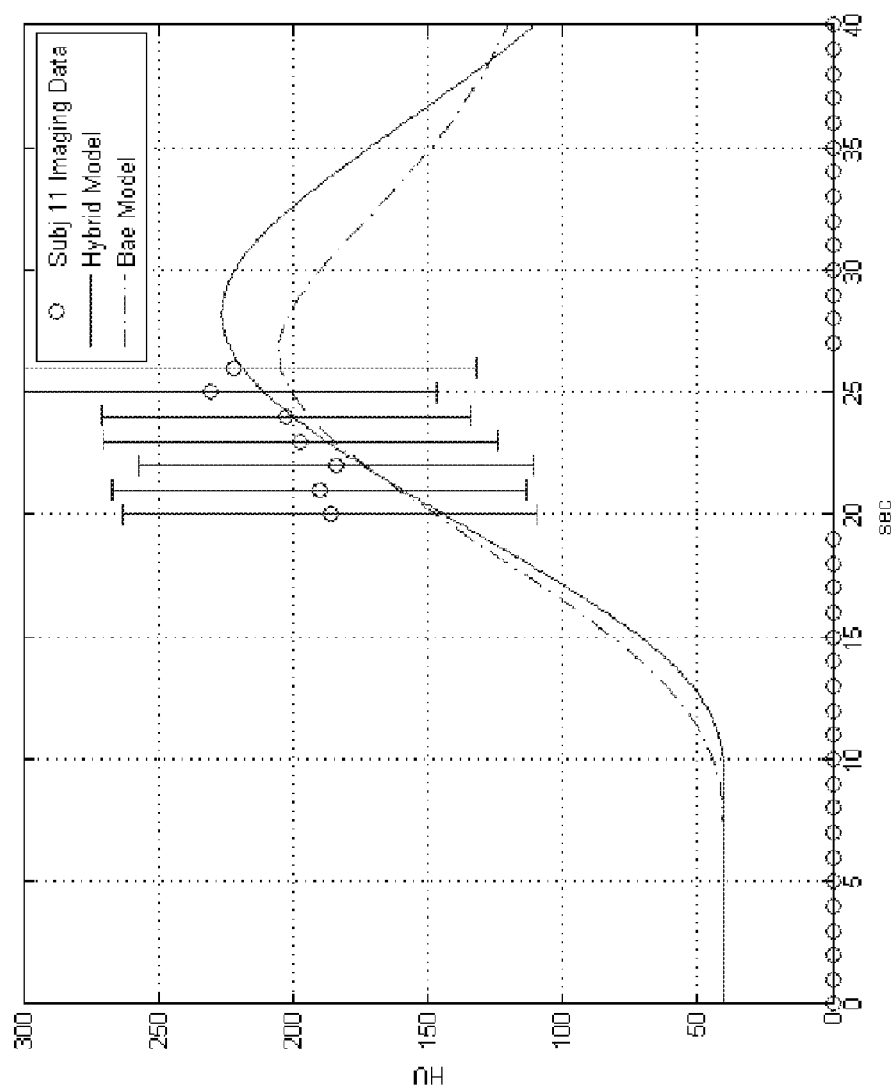
FIG. 8 illustrates one subject's (subject 11's) clinical imaging data, hybrid model simulation prediction and Bae model predictions.

All 20 sets of demographic, procedure, and imaging data were sufficient to allow simulations of the models and to allow computation of the metrics. An example simulation output using subject 11's demographic and procedure data is plotted with the contrast enhancement profile from the imaging data in FIG. 8. The error bars on each imaging data point are the standard deviations of the contrast enhancement as determined by analysis of all the pixels in the aorta at each acquisition location. Contributing to the noise at each point is intrinsic imaging noise in the CT scanner, contrast flow dynamics, image processing mechanisms, and motion of the structure.

The hybrid model using data from subject 11 a 60 year old female weighing 280 lbs with a height of 68 inches, generated an enhancement curve matching favorably—RMSE of 15 HU—to the enhancement curve acquired from the aortic imaging data for that patient. The results for this patient are displayed in FIG. 8 because the predicted enhancement curves matched very favorably to the measured data and also because heavier patients present challenges to conventional contrast dosing protocols. A total of 61 ml of 300 mgI/ml contrast was delivered at 4.1 ml/and the scan duration was 11 seconds.

Figure 9A:
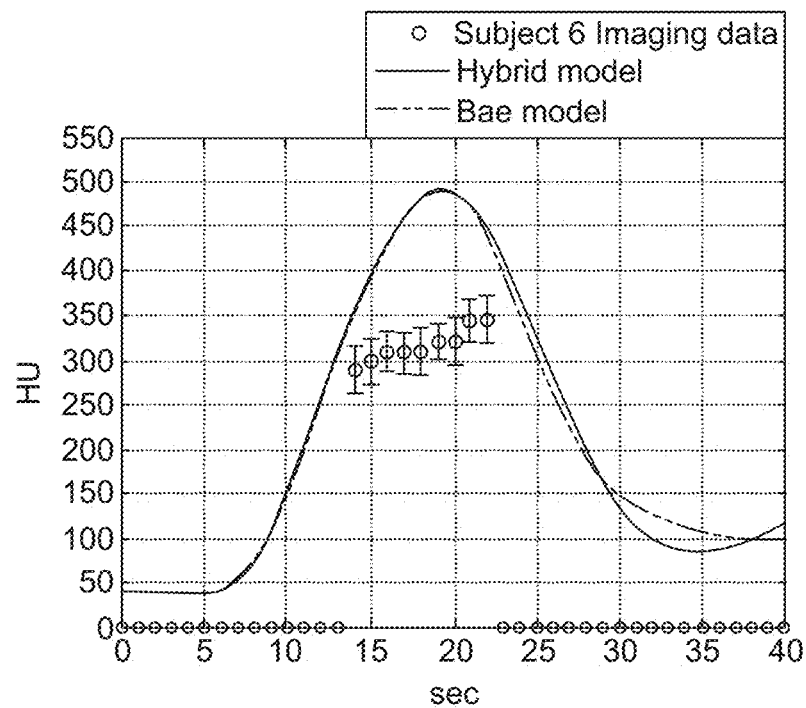
FIGS. 9A and 9B illustrate model predictions compared to clinical data for (a) subject 6 and (b) subject 8. Subject 6 was a 47 year old, 110 lb female while patient 8 was a 53 year old, 246 lb male.
Figure 9B:
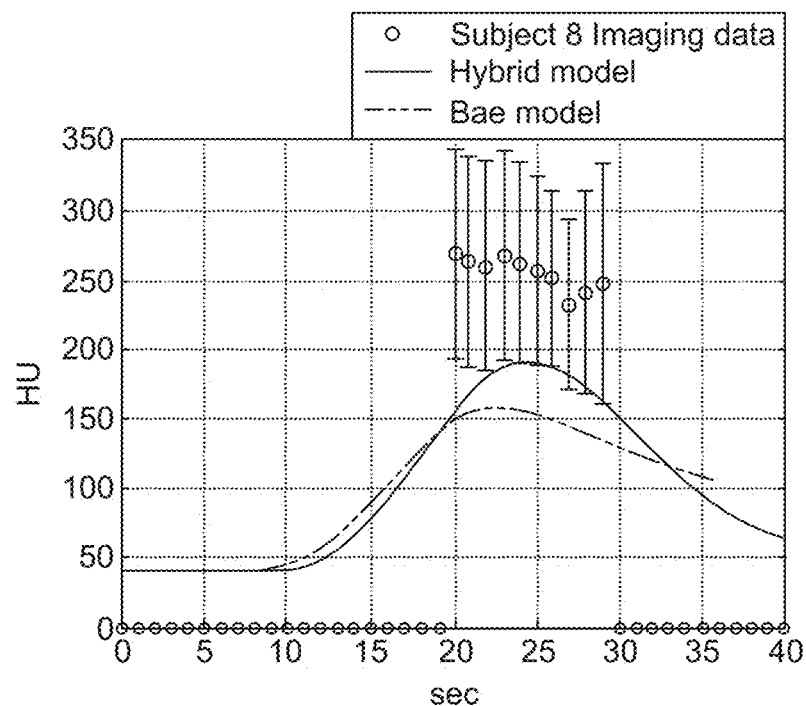

The Bae model produced an adequate enhancement curve but undershoots the empirical data by 20-40 HU. The hybrid model predicted a higher peak enhancement value than the Bae model. Linear extrapolation of the clinical data suggests the actual (assuming the ability to measure the contrast enhancement in vivo in the aorta for 10-20 more seconds) peak enhancement value should be greater than the Bae model would suggest, in agreement with the hybrid model prediction. More examples comparing enhancement predictions from the models and the two sets of imaging data are given in FIGS. 9A and 9B. The comparison of FIG. 9A is for Subject 6, who was a 37 year old female, weighing 110 lbs at a height of 61 inches with a heart rate of 80 bpm. 77 ml of 300 mgI/ml contrast material was delivered at a flow rate of 5.9 ml/s for a scan that lasted 9 seconds. Subject 8 of FIG. 9B was a 53 year old male, weighing 223 lbs at a height of 70 inches. His heart rate averaged 58 bpm. 74 ml of 300 mgI/ml contrast was injected at 4.1 ml/s and his scan duration was 12 seconds.

Both the Bae model and the hybrid model predict a contrast enhancement profile that differs from the empirical data in certain cases. For Subject 6, both the Bae and hybrid models predict enhancement maxima 200 HU less than the empirical data. For Subject 8, the hybrid model predicts a maximum enhancement 79 HU less than the empirical data's maximum. The Bae maximum prediction was 111 HU less than the empirical data's maximum. Both the Bae and hybrid models predict enhancement maxima 200 HU less than the empirical data.

Statistical results comparing the predictions of the hybrid and the Bae models are presented in tables and plots below. For each subject, the patient and procedure data were used in both models. In each instance, the model's enhancement outputs for the aortic compartment were compared to the imaging data set. Simulation data segments starting at the time point corresponding to the scan delay and lasting until the scan was completed were included in the computations of Root Mean Square Error and the Enhancement Difference Index. Tabulated results are presented in Table 5. Whereas the three comparison metrics are smaller for the hybrid model simulation, Mann-Whitney U tests do not reveal significant differences between the medians for all measures (RMSE—U=455, p=0.229; PDME—U=445, p=0.351; EDI—U=470, p=0.064).

TABLE 5

Summary results of models compared against clinical data

| metrics | Bae Model Results | | | | | Hybrid Model Results | | | | |
|---|---|---|---|---|---|---|---|---|---|---|
| | mean | stdev | min | max | median | mean | stdev | min | max | median |
| RMSE [HU] | 50.5 | 28.9 | 17.1 | 134.1 | 40.6 | 41.9 | 29.8 | 12.2 | 142.3 | 37.3 |
| PDME [%] | 18.5 | 11.7 | 3.7 | 42.9 | 15.7 | 14.6 | 10.2 | 0.8 | 42.1 | 14.5 |
| EDI [%] | 16.0 | 11.1 | 1.7 | 42.7 | 14.0 | 10.8 | 11.0 | 2.1 | 45.8 | 5.3 |

Figure 10:
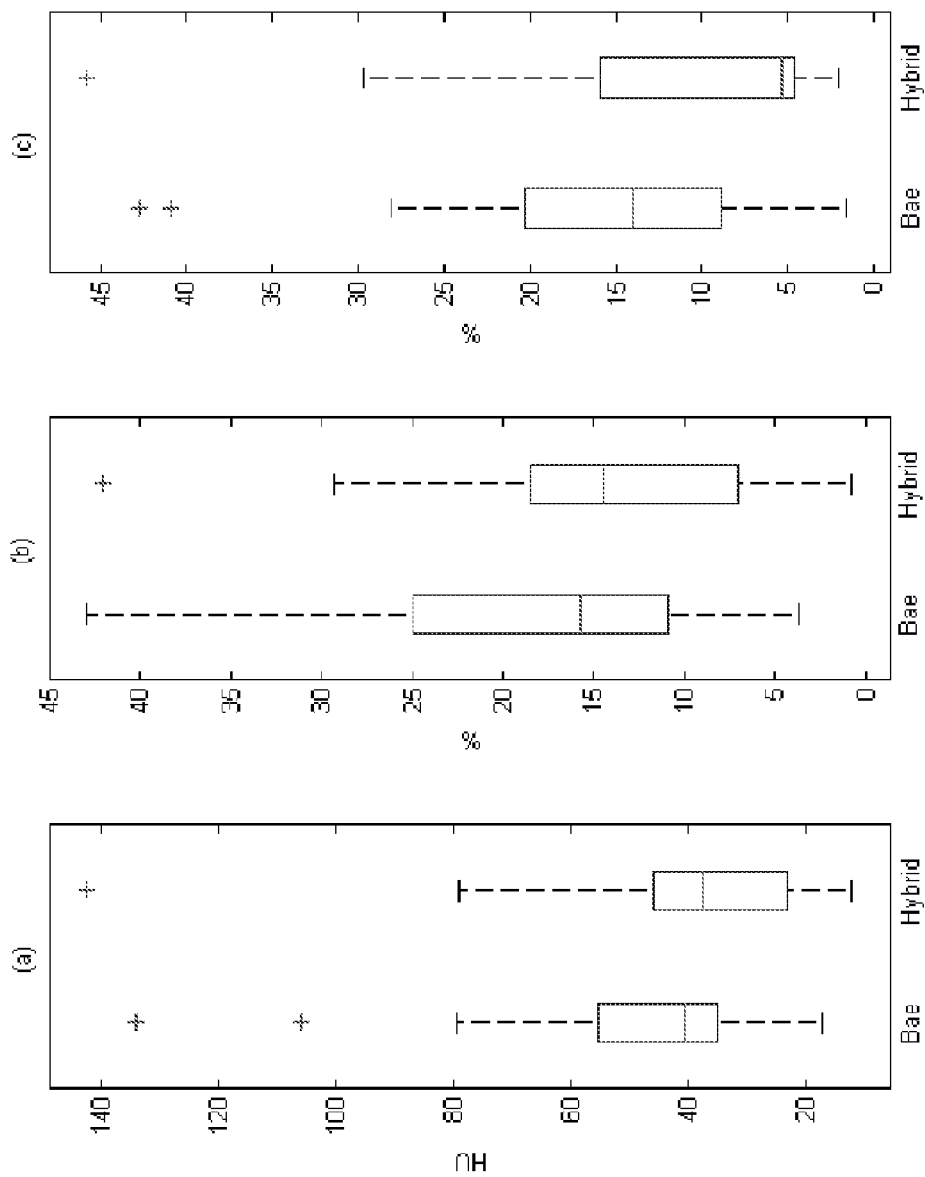
FIGS. 10A through 10C illustrate box-and-whisker plots of the summary results for (a) RMSE (b) PDME and (c) EDI.

Box-and-whisker plots for the three comparison tests reveal the skewed distribution of the data and the equivalence of medians. The box-and-whisker plots in FIG. 10 are drawn with whiskers extending to data point 1.5 times the Interquartile Range (IQR) greater or less than the median. Crosses in FIG. 10 indicate outliners that are data points greater than 1.5*IQR away from the median.

Figure 11:
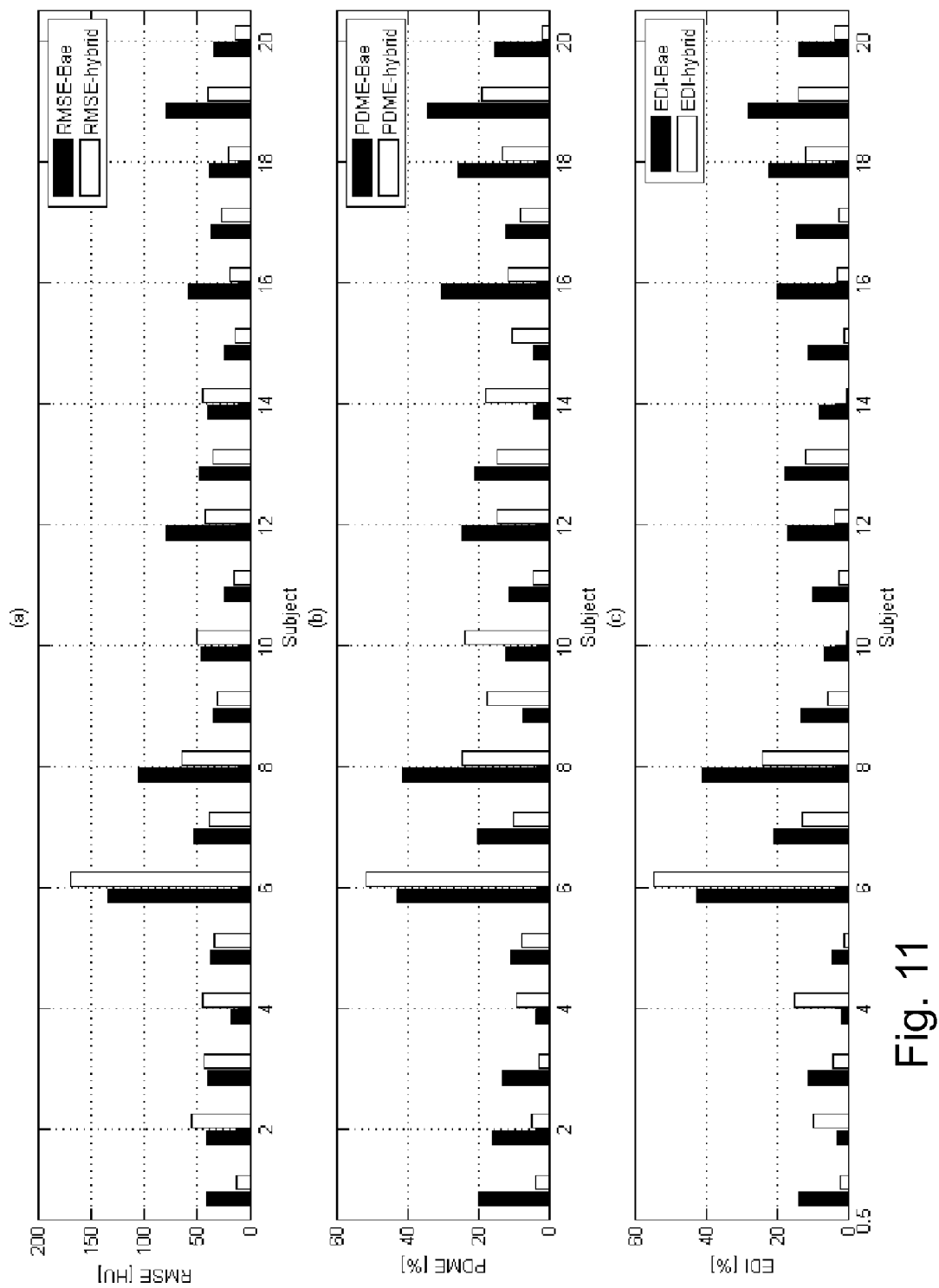
FIGS. 11A through 11C illustrate scatter plots of the simulation tests (x—=Bae model, o—=hybrid model—(a) RMSE (b) PDME (c) EDI.

Another visualization of the data is given as a series of scatter plots in FIG. 11. Visual inspection of the charts reveals the results for subjects 6, 8, 12, 16 and 19 show the greatest variation in simulation performance. The hybrid model predictions for subjects 15-20 show somewhat better agreement with the clinical data than the Bae data. The hybrid model generated lower RMSE values in 14 of the 20 subjects, lower PDME results in 13 of the 20 subjects, and lower EDI in 17 of the 20 subjects.

In comparison to the published, full-body physiologic-based pharmacokinetic of Bae et al., the hybrid model hereof has a reduced order, is discretizable, explicitly models contrast propagation delays, models the effects of saline flush injections routinely performed during CTA procedures, and models the time-varying effects of blood-plasma/contrast interactions in the peripheral venous circulation. As described above, a comparison of the hybrid model's output to clinical data published by Bae et al, shows favorable agreement. Further comparison of the hybrid model with contrast enhancement profiles derived from helical CTA data revealed close agreement with the Bae model and, in many instances, a better ability to fit the clinical data.

Use of the hybrid model to test methods to identify models from test bolus data sets is described below. In a number of studies, reduction strategies are employed, rather than attempting to fit all the parameters of the hybrid model. This model reduction can, for example, be done to reduce the computation burden and reliability of the numerical predictions.

Data-Driven Methods

In a number of embodiments, the methods, systems and models described herein are used for developing patient-specific predictions of contrast enhancement using contrast enhancement data derived from a test bolus injection. Two techniques were evaluated, one assuming a model structure (parametric) and another using a non-parametric "black box" approach. In the model-based approach, a model reduction strategy was applied to the hybrid pharmacokinetic model described above to ease the computational burden when identifying the model parameters and to overcome the challenges of modeling time varying systems.

Other approaches, including parametric and nonparametric approaches are, for example, discussed in Published U.S. Patent Application No. 2007/0255135, Published U.S. Patent Application No. 2007/0282263, Published U.S. Patent Application No. 2008/0097197, Published U.S. Patent Application No. 20080097197, Published U.S. Patent Application No. 2010/0113887, Published U.S. Patent Application No. 2010/0030073, and Published PCT International Patent Application No. WO 2009/012023, the disclosures of which are incorporated herein by reference.

Parametric (Model Based) Identification

In a number of embodiments for constructing a data-dependent, patient specific contrast propagation model with a reduced-order form of the hybrid PBPK model described above, model parameters are estimated after acquisition of, for example, two CT time-enhancement curves (sequential low-level CT scans at the level of the pulmonary trunk) resulting from the injection of a small "identification" bolus of contrast medium (10-20 ml).

Contrast agent is infused into the peripheral circulatory system, typically via intravascular access in a forearm vein or in the antecubital fossa. Several seconds later, the bolus of contrast arrives in the right heart. Next, the right ventricle pushes the contrast bolus through the pulmonary circulation. At this point, the transport of the contrast bolus is dominated by central circulatory parameters, namely the cardiac output. Between 6 and 20 seconds later, the contrast arrives in the left side of the heart and is ejected by the left ventricle into the main arterial and coronary vasculature. By positioning an axial CT acquisition at the level of the pulmonary trunk and acquiring CT images at that level every n seconds, a numerical and graphical depiction of the contrast's transport is generated.

Figure 12:
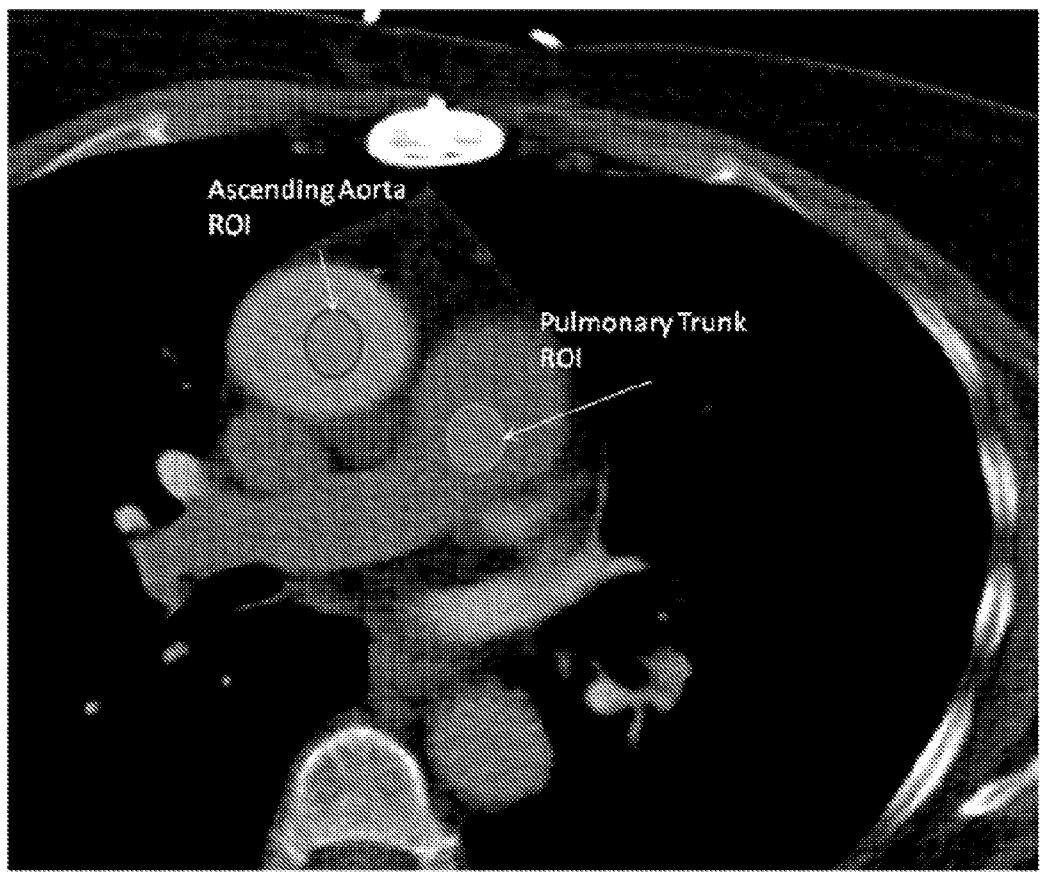
FIG. 12 illustrates an axial CT image acquired from a test bolus scan procedure.

FIG. 12 presents an axial "slice" of cross-sectional image data acquired from a patient undergoing CT Angiography. A small test bolus of contrast (20 ml of 350 mgI/ml) was injected peripherally and scans were taken at the level of the pulmonary trunk every 2 seconds. As contrast flows through the anatomy, image enhancement or brightness in vascular structures increases. Upon acquisition of the axial images, the scanner or off-line processing software performs a surface integration within the Regions of Interest (ROI's) on each image and plots the averaged attenuation value with respect to time. Standard clinical practice is to start the acquisition 5-10 seconds after the start of contrast injection and to acquire images for 20-30 seconds at a standard tube voltage (120 kV) but at a low tube current-time product (10-30 mAs).

Figure 13:
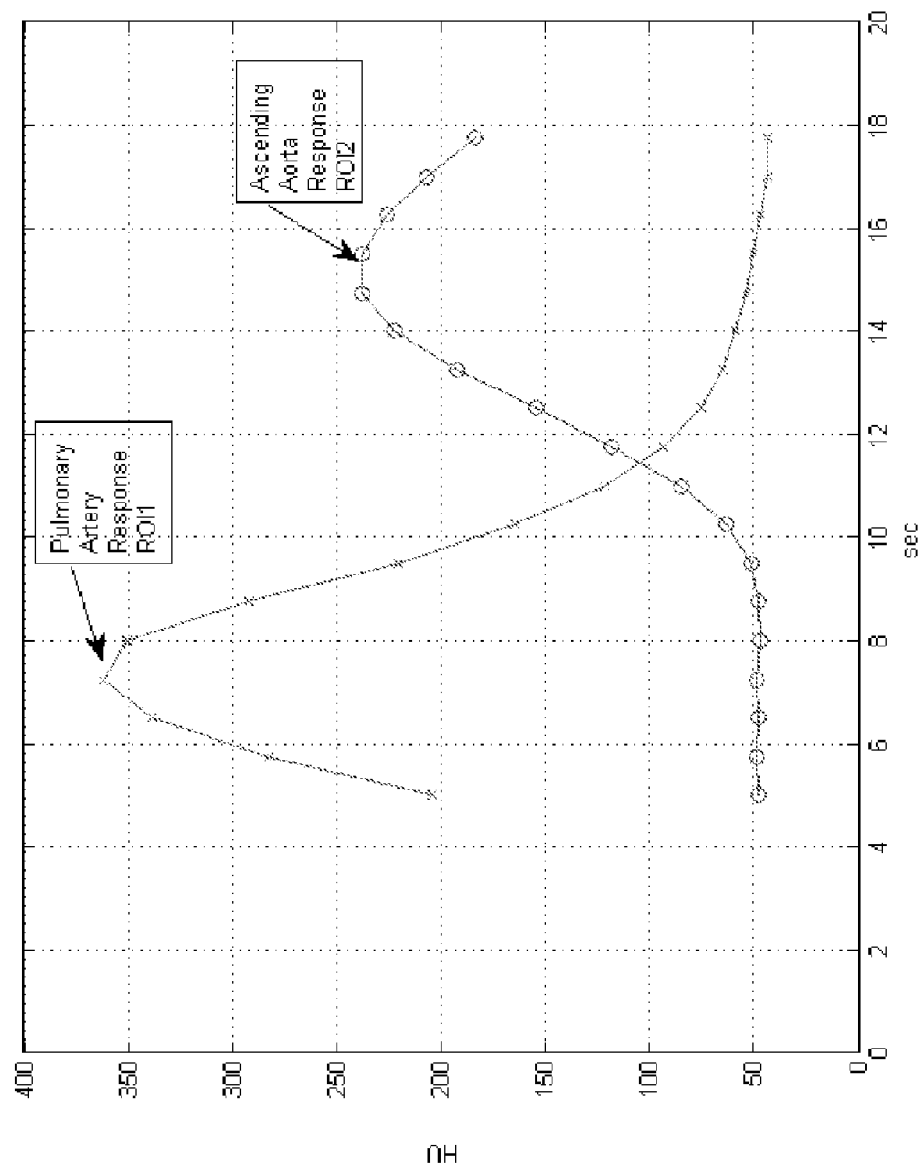
FIG. 13 illustrates time enhancement curve generated from a patient after analysis of the test bolus scan arising from a test bolus contrast injection (data set from FIG. 12).

Typical Time Enhancement Curves or TEC for a human subject are shown in FIG. 13. A region of interest (ROI) marker is placed over the subject's pulmonary artery trunk and the ascending aorta as demonstrated in FIG. 12.

An attempt to fit all the parameters of the hybrid model hereof using the limited length of data available from test bolus TECs was not made. Rather, a model reduction strategy was employed where the most relevant compartments of the hybrid model are considered during the first-pass of the contrast agent—the peripheral venous compartment, the right heart compartment, the lung compartment and the left heart/aortic compartment. This approach is justified by recognition that CTA imaging is performed during the first-pass of the contrast material and is typically ended 30 seconds after the initiation of contrast injection due to the short scan acquisition time of the scanner. There are also intrinsic challenges to statistical identification techniques when feedback is present in the system. Contrast recirculation would be considered a type of feedback in the hybrid model.

Figure 14:
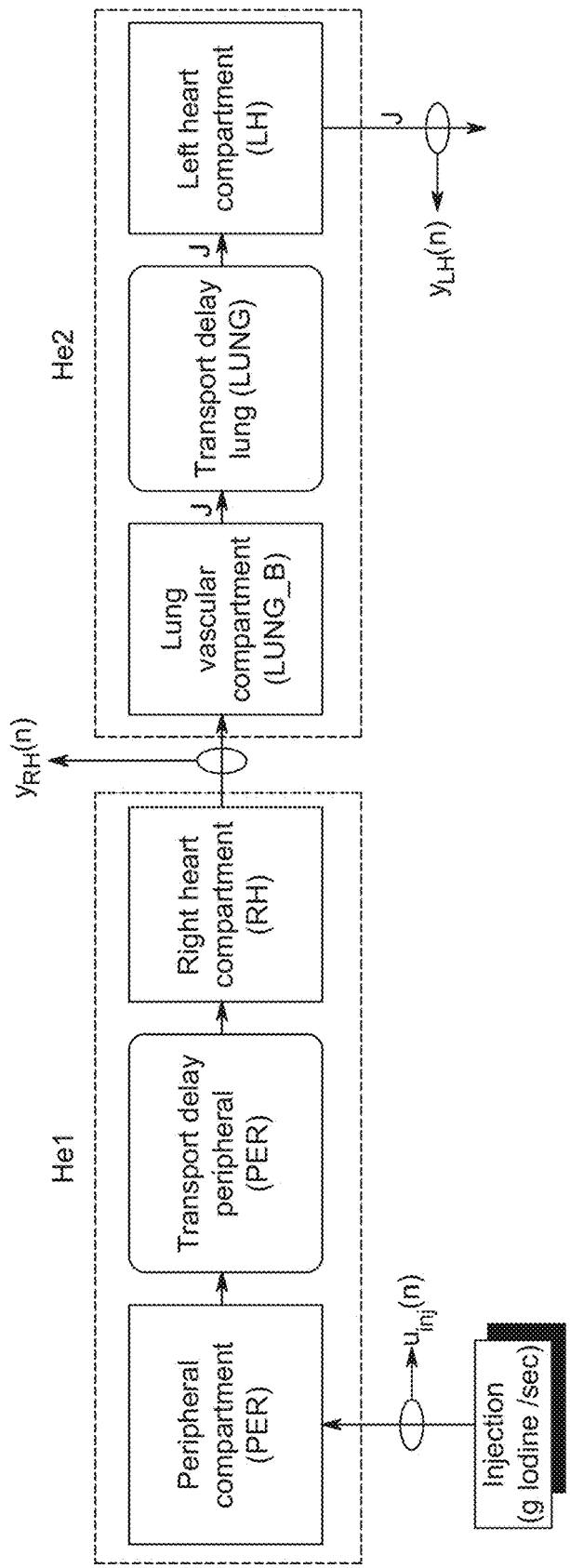
FIG. 14 illustrates an embodiment of a reduced hybrid model structure used for parameter estimation with test bolus scan data. The dashed lines represent the model subsystems combined for model identification.

FIG. 14 is an illustration of the hybrid model subsystems used for parameter estimation. The PER and RH compartments are collapsed into one transfer function, He1, where the contrast injection infusion is the input function $u_{inj}(n)$ and the measured TEC (ROI1 in FIG. 13) is an illustration of the hybrid model subsystems used for parameter estimation. The PER and RH compartments are collapsed into one transfer function, He1, where the contrast injection infusion is the input function $u_{inj}(n)$ and the measured TEC (ROI1 in FIG. 13) in the pulmonary trunk, $y_{RH}(n)$, is the output signal. $y_{RH}(n)$ is converted to blood plasma concentration using a scaling coefficient dependent on the scanner configuration and determined via calibration. Because linearity is assumed throughout the model, the transport delay describing the propagation delay of the contrast bolus from the injection site to the pulmonary artery can be positioned anywhere within the He1 block. Likewise, the LUNG_B and LH subsystems are combined into one subsystem with transfer function He2. The input function for the He2 block is $y_{RH}(n)$ and the output signal is the measured concentration TEC $y_{RH}(n)$ derived from the ROI (ROI2 in FIG. 13) placed in the aorta during a test bolus scan) in the pulmonary trunk, $y_{RH}(n)$, is the output signal. $y_{RH}(n)$ is converted to blood plasma concentration using a scaling coefficient dependent on the scanner configuration and determined via calibration. Because linearity is assumed throughout the model, the transport delay describing the propagation delay of the contrast bolus from the injection site to the pulmonary artery can be positioned anywhere within the He1 block. Likewise, the LUNG_B and LH subsystems are combined into one subsystem with transfer function He2. The input function for the He2 block is $y_{RH}(n)$ and the output signal is the measured concentration TEC $y_{RH}(n)$ derived from the ROI (ROI2 in FIG. 13) placed in the aorta during a test bolus scan.

By performing the parameter estimation in two distinct operations, computational complexity is reduced. In addition to reducing computational complexity, a theoretical reduction in parameter variance can be realized when fewer parameters are identified using input/output data. Furthermore, a reduction in the total number of parameters identified with a pair of input/output data help prevent overfitting.

Figure 15:
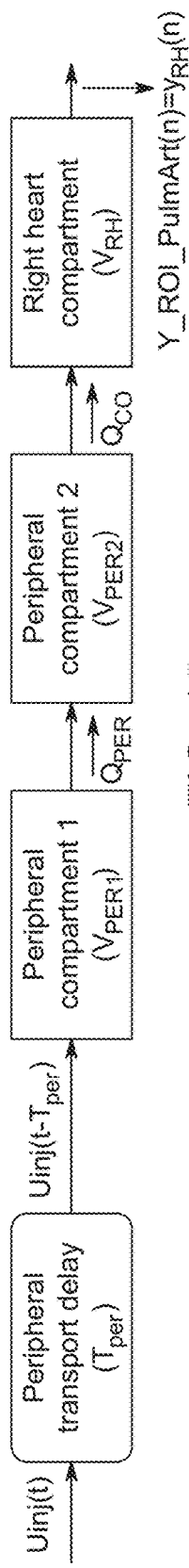
FIG. 15 illustrates an embodiment of a reformulated right heart and peripheral compartments (He1) model structure for use in the parameter estimation. The mass flow rate terms, $Q_{PER}$ and $Q_{CO}$ transport contrast from peripheral compartment one to two and from peripheral compartment two into the right heart.

Including only the RH and PER compartments, in the HE1 system, during preliminary parameter estimation resulted in non-convergence and poor fitting of experimental data. Increasing the order of the He1 system by introducing an "intermediate" compartment between the peripheral vein compartment and the right heart compartment resulted in convergence of the parameter estimators. This intermediate compartment also provides a means to model the effects of the injection flow rate within the peripheral compartment because the mass flux between the peripheral compartments is driven by a new volumetric flow rate term, $Q_{PER}$ that is neither the injection flow rate nor the flow rate of blood entering the right heart. The model structure is presented in FIG. 15 which shows $u_{inj}(t)$, the contrast bolus injection into a peripheral vein, and $y_{RH}(t)$, a TEC measured in the pulmonary artery (and converted to concentration units from HU).

The continuous time state-space formulation for He1 is:

$$A_{He1} = \begin{bmatrix} \frac{-Q_{PER}}{V_{PER1}} & 0 & 0 \\ \frac{Q_{PER}}{V_{PER1}} & \frac{-Q_{CO}}{V_{PER2}} & 0 \\ 0 & \frac{Q_{CO}}{V_{PER2}} & \frac{-Q_{CO}}{V_{RH}} \end{bmatrix} \quad (31)$$

$$B_{He1} = [1 \ 0 \ 0]^T$$

$$C_{He1} = \begin{bmatrix} 0 & 0 & \frac{1}{V_{RH}} \end{bmatrix}$$

$$D_{H1} = [0]$$

$$\dot{x}_{He1}(t) = A_{He1} x_{He1} + B_{He1} u_{inj}(t - T_{PER}) \quad (32)$$
$$y_{He1}(t) = C_{He1} x_{He1}(t)$$

and recalling that $y_{He1}(t) = y_{RH}(t)$ when measured data are available from CT data collected in a Right Heart structure, such as the pulmonary artery. The transport delay of the contrast through the peripheral venous circulation is $T_{PER}$. The input function in equation 32 is parameterized by the administration flow rate ($Q_{inj}$), the concentration of the test bolus ($C_{inj}$), and the contrast bolus duration $T_{DUR}$:

$$u_{inj}(t) = Q_{inj}(t) C_{inj}[u(t) - u(t - T_{DUR})] \quad (33)$$

where u(t) is the unit-step function.

The contrast injection flow rate ($Q_{inj}$) is omitted in the formulation of equation 31 because it is assumed that the identification data set is acquired when a saline bolus flush follows the test bolus contrast volume. A saline infusion following the test bolus maintains the flow rate in the peripheral compartments ($Q_{PER}$) for a duration of 10-14 seconds (the volume of contrast and saline divided by the flow rate). A typical diagnostic bolus has duration of 10-14 seconds (contrast) so the assumption is that the peripheral flow rate during the diagnostic injection will be the same as during the test bolus injection.

Because the CT data are acquired by single-level scanning at discrete time steps, the models used in the identification step were discretized. Discretization of the continuous state-space system defined in equation 31 was obtained by a standard transformation of Linear System Theory:

$$A_{He1D} = e^{A_{He1}\Delta} \quad (34)$$

$$B_{He1D} = \int_{\tau=0}^{\Delta} e^{A_{He1}\tau} B_{He1} d\tau$$

The subscript "D" refers to the discretized state-space matrix form and Δ is the sampling interval defined by the time between single-level scans. This approach yields the following state-space matrices:

$$A_{He1D} = \begin{bmatrix} e^{\frac{-Q_{PER}}{V_{PER}}\Delta} & 1 & 1 \\ e^{\frac{Q_{PER}}{V_{PER1}}\Delta} & e^{\frac{-Q_{CO}}{V_{PER2}}\Delta} & 1 \\ 1 & e^{\frac{Q_{CO}}{V_{PER2}}\Delta} & e^{\frac{-Q_{CO}}{V_{RH}}\Delta} \end{bmatrix} \quad 35$$

-continued $$B_{He1D} = \begin{bmatrix} -\frac{V_{PER1}}{Q_{PER}}\left(e^{-\frac{Q_{PER}}{V_{PER1}}\Delta} - 1\right) \\ \frac{V_{PER1}}{Q_{PER}}\left(e^{\frac{Q_{PER}}{V_{PER1}}\Delta} - 1\right) \\ 0 \end{bmatrix}$$

$$C_{He1D} = \begin{bmatrix} 0 & 0 & \frac{1}{V_{RH}} \end{bmatrix}$$

$$D_{He1D} = [0]$$

Figure 16:
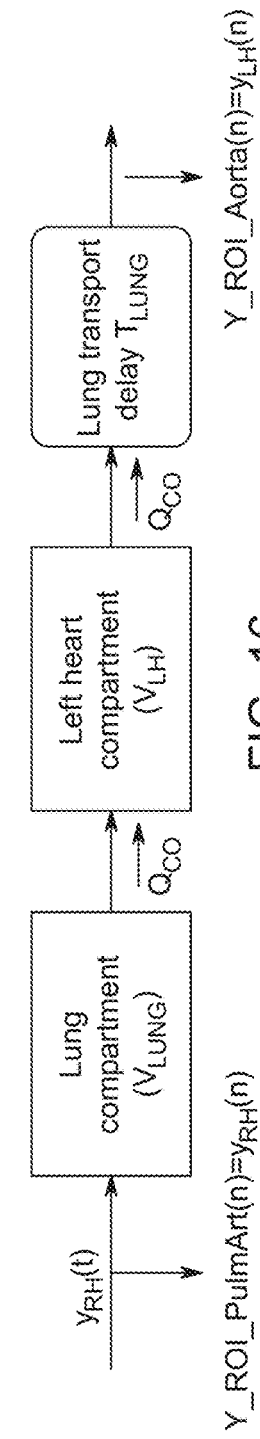
FIG. 16 illustrates an embodiment of a reformulated left heart and lung compartment (He2) model structure for use in the parameter estimation. The cardiac output ($Q_{CO}$) transports the contrast bolus from the Lung compartment to the Left Heart compartment.

The second sub-system of the model is a combination of the Lung and Left-Heart compartments, denoted as He2 in FIG. 14. Because first-pass circulatory effects dominate when predicting contrast enhancement for CT Angiography, the transport of contrast from the vascular region to lung tissue can be ignored. As in the derivations of the hybrid model, the propagation delay of contrast material through the cardiopulmonary circuit is lumped into a transport delay, $T_{LUNG}$. A graphical depiction of the isolated He2 sub-system is presented in FIG. 16.

The continuous time state-space dynamics for He2 are:

$$A_{He2} = \begin{bmatrix} \frac{-Q_{CO}}{V_{LUNG}} & 0 \\ \frac{Q_{CO}}{V_{LUNG}} & \frac{-Q_{CO}}{V_{LH}} \end{bmatrix} \quad (36)$$

$$B_{He2} = [Q_{CO} \ 0]^T$$

$$C_{He2} = \begin{bmatrix} 0 & \frac{1}{V_{LH}} \end{bmatrix}$$

$$D_{He2} = [0]$$

$$x_{He2}(t) = A_{He2}x_{He2} + B_{He2}y_{RH}(t - T_{LUNG}) \quad (37)$$
$$y_{He2}(t) = C_{He2}x_{He2}(t)$$

and $y_{He2}(t)=y_{LH}(t)$ when TEC data are available from a left heart structure, such as the ascending aorta. Applying equation 34 to the system equations results in the discrete-time representation for the A and B matrices (the C and D matrices are equivalent to the continuous-time version), with $\Delta$ representing the sampling time:

$$A_{He2D} = \begin{bmatrix} e^{-\frac{Q_{CO}}{V_{LH}}\Delta} & 1 \\ e^{\frac{Q_{CO}}{V_{LUNG}}\Delta} & e^{-\frac{Q_{CO}}{V_{LH}}\Delta} \end{bmatrix} \quad (38)$$

$$B_{He2D} = \begin{bmatrix} -V_{LH}\left(e^{-\frac{Q_{CO}}{V_{LH}}\Delta} + 1\right) \\ V_L\left(e^{\frac{Q_{CO}}{V_{LUNG}}\Delta} - 1\right) \end{bmatrix}$$

$$C_{He2D} = \begin{bmatrix} 0 & \frac{1}{V_{LH}} \end{bmatrix}$$

$$D_{He2D} = [0]$$

Figure 17:
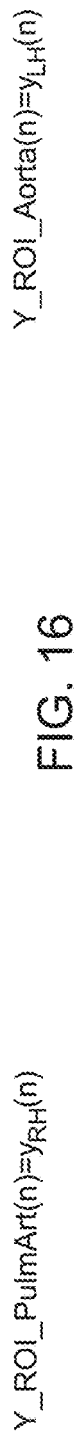
FIG. 17 illustrates a block diagram of an embodiment of a discrete model used for identifying parameters with a maximum likelihood estimator.

The two discrete systems serve as the basis for embodiments of data-driven parameter estimation technique developed herein. Input to the first discrete system (He1D) is a sampled injection input signal, $u_{inj}(n)$ (discrete version of equation 33) and the output is the TEC measured in the pulmonary trunk, $y_{RH}(n)$ (ROI1 in FIG. 13). The input to the second discrete system, He2D, is $y_{RH}(n)$ and the output vector is the TEC measured from the Ascending Aorta, $y_{LH}(n)$ (ROI2 in FIG. 13). FIG. 17 presents a block-diagram view of the two discrete systems and the respective inputs and outputs for the systems. The two, discrete, state-space systems used in the parameter estimation are:

$$x_{He1D}(n)=A_{He1D}x_{He1D}+B_{He1D}u_{inj}(n-T_{PER})$$

$$\hat{y}_{RH}(n)=C_{He1D}x_{He1D}(n) \quad (39)$$

$$x_{He2D}(n)=A_{He2D}x_{He2D}+B_{He2D}y_{RH}(n-T_{LUNG})$$

$$\hat{y}_{LH}(n)=C_{He2D}x_{He2D}(n) \quad (40)$$

The parameters to be estimated in the first system, He1D, are: $V_{PER1}$, $V_{PER2}$, $V_{RH}$, $Q_{PER}$, $Q_{CO}$, and the transport delay $T_{PER}$. Parameters to be estimated in the second system are: $V_{LH}$, $V_{LUNG}$, $Q_{CO}$, and the transport delay through the pulmonary system $T_{LUNG}$.

Maximum Likelihood Estimator

In a number of embodiments of estimating parameters from scan data acquired after the injection of a small bolus of contrast medium or material into a patient, parameter estimation occurs in two distinct steps. By using two measured signals, $y_{RH}(n)$ and $y_{LH}(n)$, and estimating the two systems serially, the convergence time, computation burden and parameter variability are reduced because fewer parameters need to be identified in one single identification step by numerical optimization. For example, instead of estimating 10 parameters with the sampled test bolus enhancement data, six parameters are identified in He1D using the known input function, $u_{inj}(n)$ and the output signal $y_{RH}(n)$ (which might only have 10 data points) and then only 4 parameters for He2D are identified in another separate parameter estimation step (using $y_{RH}(n)$ and $y_{LH}(n)$ as input/output data).

First, the "He2" system is parameterized using the scan data from a test bolus injection and the resulting TECs measured in the pulmonary artery and the ascending aorta—$y_{RH}(n)$ and $y_{LH}(n)$. Next, the "He1" system is parameterized using the signals $u_{inj}(n)$ and $y_{RH}(n)$, the input injection function and the TEC measured in the pulmonary artery. After estimating the parameters, an individual model for that patient is constructed using equations 39 and 40. Goodness-of-fit is determined by comparing the predicted enhancement in the ascending aorta (with a test bolus injection) against the measured data.

Because a large number of noise sources influence the measurement process, including the Zero-Order sampling process, it can, for example, be assumed the errors are normally distributed throughout the system. With the assumption of Gaussian distributed error and independent noise processes, Maximum Likelihood Estimation (MLE) can be used for estimating the unknown model parameters. Other methods can, for example, be used to estimate unknown parameters as clear to those skilled in the art. The cost function used in the MLE when estimating the parameters of He1D and He2D is the sum of squared differences between the measured test bolus TEC data $y_{RH}(n)$ and $y_{LH}(n)$ and the estimated test bolus response in those structures, $\hat{y}_{RH}(n)$ and $\hat{y}_{LH}(n)$:

$$\hat{\theta}_{He1D} = \arg\min_{\theta_{He1D}} \frac{1}{2\sigma_{meas}^2} \sum_{i=1}^{N} (y_{RH}(i) - \hat{y}_{RH}(\theta_{He1D}, i))^2 \quad (41)$$

$$\hat{\theta}_{He2D} = \arg\min_{\theta_{He2D}} \frac{1}{2\sigma_{meas}^2} \sum_{i=1}^{N} (y_{LH}(i) - \hat{y}_{LH}(\theta_{He2D}, i))^2 \quad (42)$$

where the parameter estimate vectors ("hat" notation, ^, signifies estimated parameters):

$$\hat{\theta}_{He1D} = [V_{PER1} V_{PER2} V_{RH} Q_{PER} Q_{CO_r} T_{PER}]^T$$

$$\hat{\theta}_{He2D} = [V_{LUNG} V_{LH} Q_{CO} T_{LUNG}]^2 \quad (43)$$

recognizing that maximum likelihood estimation is equivalent to least squares fitting when the noise processes are Gaussian. The variance term, $\sigma_{meas}^2$ in equations 42 and 42 does not enter into the cost function and may be estimated post-hoc, based on noise estimates from the measured TECs. In the summations of equation 41 and equation 42, N is the number of TEC samples available from the test bolus enhancement data, and the index variable, i, ranges across the discrete-time samples.

In matrix notation, the problem is stated as minimizing the sum of squares of residuals through a function of the estimated parameters:

$$J_{RH}(\hat{\theta}_{He1D}) = \|r_{RH}(\hat{\theta}_{He1D})\|^2 = \|y_{RH} - f_{RH}(\hat{\theta}_{He1D})\|^2 \quad (44)$$

$$J_{LH}(\hat{\theta}_{He2D}) = \|r_{LH}(\hat{\theta}_{He2D})\|^2 = \|y_{LH} - f(\hat{\theta}_{He2D})\|^2 \quad (45)$$

where $f(\hat{\theta}_i)$ are n-vectors that estimate the LH and RH signals given the p-value parameter estimates $\hat{\theta}_{He1D}$ and $\hat{\theta}_{He2D}$ (p=6 and p=4) and inputs. The vectors $r_{RH}(\hat{\theta}_{He1D})$ and $r_{LH}(\hat{\theta}_{He2D})$ are the residuals for the estimates of the He1D and He2D systems:

$$r_{RH}(\hat{\theta}_{He1D}) = y_{RH} - (C_{He1D} x_{He1D} + \eta(n)) \quad (46)$$

$$r_{LH}(\hat{\theta}_{He2D}) = y_{LH} - (C_{He2D} x_{He2D} + \eta(n)) \quad (47)$$

with $\eta(n)$ representing the model and measurement uncertainty.

The n×p Jacobian matrices, $\mathbf{V}_{RH}$, $(\hat{\theta}_{He1D})$ and $\mathbf{V}_{LH}$ $(\hat{\theta}_{He2D})$ are constructed from the first derivatives of the residual vectors with respect to the parameter vectors. Note that bold V notation is used for the Jacobians while V (non-bold) is used for volume. The $i^{th}$ and $j^{th}$ elements of the Jacobian matrices are:

$$V_{i,j}^{RH} = \frac{\partial r_i}{\partial \theta_j^{RH}} = \frac{\partial (y_{RH}(i) - C_{RH} x_i^{RH})}{\partial \theta_j^{RH}} \quad (48)$$

$$V_{i,j}^{LH} = \frac{\partial r_i^{LH}}{\partial \theta_j^{LH}} = \frac{\partial (y_{LH}(i) - C_{LH} x_i^{LH})}{\partial \theta_j^{LH}} \quad (49)$$

The maximum likelihood estimates of the parameter vectors are normally distributed with covariance of $\Sigma = \sigma^2 (V^T V)^{-1}$ where the estimators of variance are [55]:

$$\hat{\sigma}_{RH}^2 = \frac{J_{RH}(\hat{\theta}_{RH})}{(n-p)} \quad (50)$$

$$\hat{\sigma}_{LH}^2 = \frac{J_{LH}(\hat{\theta}_{LH})}{(n-p)}$$

The variance of the parameter estimates can also be expressed as the inverse of the Fisher Information Matrix (the inverse of the Hessian), which is often accessible from numerical computing packages such as MATLAB's optimization toolbox.

An approximate expression for the parameter bias, that is the difference between the estimated and the true parameter, can be expressed in terms of the Jacobian matrices:

$$E\{\hat{\theta} - \theta\} \approx (V^T V)^{-1} V^T d \quad (51)$$

where $$d = \sigma_2^2 (\text{trace}((V^T V)^{-1} H))^T$$

where H is the p×p Hessian matrix (derivative of the Jacobian).

Because the model, as defined by equation 39 and equation 40, is non-linear in the parameters the minimization of the cost functions is a non-linear Least Squares (NLS) problem. There are numerous iterative techniques for solving NLS problems. An optimization scheme for this problem can provide non-negativity constraints on the parameters. Also, it is reasonable to enforce physiologic bounds on the parameter estimates. Because the problem is a constrained minimization, line-search techniques like Gaus-Newton, simplex or hybrid techniques like the classic Levenberg-Marquardt are not applicable. For this reason, a subspace trust-region method, based on an interior-reflective Newton method as implemented in the MATLAB Optimization toolbox (nonlinsq), was used to estimate the parameter vectors in equation 43. The algorithm computes an approximate solution at each iteration of the solver using a Precondition Conjugate Gradient (PCG) technique. Finite difference approximations were used to construct the Jacobian and Hessian matrices during the solution process.

In the experiments described below, the minimizations were run with convergence criteria of $10^{-5}$ on the cost function evaluation and a tolerance of $10^{-5}$ on the parameters. A maximum number of function evaluations of 400 was set and the maximum number of iterations at each solution step allowed was 500. The parameter bounds for $\hat{\theta}_{He1D}$ and $\hat{\theta}_{He2D}$ used in the experiments are presented in Table 6.

TABLE 6

Upper and lower boundaries or constraints on the estimated parameters

| $\hat{\theta}_{He1D}$ | | | $\hat{\theta}_{He2D}$ | | |
|---|---|---|---|---|---|
| Parameter | Lower Bound | Upper Bound | Parameter | Lower Bound | Upper Bound |
| $V_{RH}$ [ml] | 30 | 400 | $V_{LH}$ [ml] | 50 | 400 |
| $V_{PER1}$ [ml] | 10 | 90 | $V_{LUNG}$ [ml] | 250 | 825 |
| $V_{PER2}$ [ml] | 10 | 200 | $Q_{CO}$ [ml/s] | 30 | 200 |
| $T_{PER}$ [sec] | 1 | 5 | $T_{LUNG}$ [sec] | 1 | 8 |
| $Q_{PER}$ [ml/s] | 1 | 80 | | | |
| $Q_{CO_r}$ [ml/s] | 30 | 170 | | | |

The parameters were initialized, prior to starting the estimation, at 50% midpoints of the upper and lower parameter bounds. To investigate the sensitivity of the solver to initial condition selection, five solver runs were executed per parameter estimation. The initialization vector with the best-fit output curve was selected as the starting estimate. The estimated output vector for the He1D system, $\hat{y}_{RH}(n)$ was used as the input to He2D system when performing forward predictions of contrast enhancement.

Parametric Estimator Evaluation Methods.

To demonstrate the effectiveness of the parameter estimation technique, three distinct experiments were conducted. The first two experiments used synthetic data to determine properties of the estimator (bias, variance) and its robustness to truncated input/output data and variations in temporal sampling of the data. Retrospective clinical data were then used to determine the estimator's performance in predicting aortic contrast enhancement in human subjects, based on timing bolus scan TECs measured in the pulmonary trunk and the ascending aorta.

Model-to-Model Comparisons.

To characterize the estimator, a synthetic data set was created using the system defined by equations 39 and 40, the same equations used by the estimator. The hybrid model, therefore, did not generate the data used in these experiments. The intent of this methodology was to isolate the performance of the estimator independent of the measurement data. This type of comparison has been termed a "model-to-model" comparison in the literature and is useful for studying the behavior of an estimator independent of other factors such as model accuracy, sampling noise and variability in noise processes. The model-to-model terminology indicates that the same model used for estimating the parameters generated the data. It is also useful for visualizing the solution space and assessing the performance of the estimators because the "true" parameters, $\theta_{He1D}^{true}$ for i=1, 2 are known. A data set was computed using the parameter values specified in Table 7.

TABLE 7

Parameter values used in the model-to-model simulations and comparisons.

| $\theta_{He1D}^{true}$ | | $\theta_{He2D}^{true}$ | |
|---|---|---|---|
| Parameter | Value | Parameter | Value |
| $V_{RH}$ [ml] | 200 | $V_{LH}$ [ml] | 325 |
| $V_{PER1}$ [ml] | 30 | $V_L$ [ml] | 310 |
| $V_{PER2}$ [ml] | 100 | $Q_{CO}$ [ml/s] | 90 |
| $T_{PER}$ [sec] | 2 | $T_{LUNG}$ [sec] | 3 |
| $Q_{PER}$ [ml/s] | 4 | | |
| $Q_{COr}$ [ml/s] | 80 | | |

The input function, $u_{inj}(t)$ of equation 33 was parameterized by contrast concentration of 370 mgI/ml ($C_{inj}$) for a duration of 5 seconds ($T_{DUR}$), at a flow rate of 5 ml/s ($Q_{inj}$). Simulations were performed in MATLAB using a time-step of 0.10 sec/sample. The simulated TECs were downsampled at rates of 1 sec/sample, 2 sec/sample and 5 sec/sample to mimic the effect of sampling on the TECs by the CT scanner.

Simulations were also performed with the "true" parameters corrupted with synthetic measurement noise (AWGN) having standard deviations of 0, 1 and 2 HU ($\eta(n)$ in equations 46 and 47 to develop estimates of bias and variance. For every combination of noise level and sample time, 30 parameter estimations were performed. For each simulation run, the initial parameter estimates were varied by 25% of the nominal values. Five parameter estimates were computed and the best set of parameters was determined by choosing the set which generated the minimum residual Mean Square Error between the predicted enhancement curve from the parameter estimation and that generated by the model, $\hat{y}_{RH}^{Test}(n)$, $\hat{y}_{LH}^{TEST}(n)$.

Finally, noise-free simulations were performed with true parameter values varied by +/−20% in 2% increments to generate graphical illustrations of the cost functions $J_{RH}$ ($\theta_{He1D}$), and $J_{LH}(\theta_{He2D})$. These simulations also allow for analysis of the sensitivity of the estimator to initial condition selection. Five simulations using with the initial conditions randomly varied within 25% of the values in Table 7 were executed. The Root Mean Square Error between the predicted test bolus and the simulated test bolus enhancement for each set of initial conditions were recorded and analyzed.

Estimator Performance Using Hybrid Model Data.

The estimator's performance was determined in the presence of noise and sensitivity to truncated test bolus enhancement data using hybrid model data. The hybrid model was simulated using the parameters and methods presented above, wherein simulated subject demographic data, and the relationships defined in equations 27, 28 and 29 provided the values for cardiac output and blood volume. The parameter values in Tables 1 through 3 configured the model. MATLAB/Simulink (R2008b) was used to simulate the model for each patient using the clinical data for patient parameters and the diagnostic phase contrast injection protocol, including the saline flush phase. The same parameter set was used to create synthetic, discrete test bolus data $y_{RH}^{Test,H}(n)$ and $y_{LH}^{Test,H}(n)$ from equation 9 and 11 where the superscript (Test,H) denotes a simulated test bolus injection response created from the hybrid model. The patient demographics used for simulations described above parameterized the model system as set forth in equation 15. A fixed flow rate and contrast volume injection signal (uDiag(n)) was delivered to each simulated "subject" to generate a simulated enhancement curve $y_{LH}^{Diag,H}(n)$. The injection protocol, $u_{Diag}(n)$, was parameterized with the following values: Qinj=5 ml/s, Cinj=350 mgI/ml, for 25 seconds followed by a saline phase at a flow rate of 5 ml/s and duration of 8 seconds.

Parameter estimation was performed with Gaussian noise vectors with standard deviations of: 0.1, 0.25, 0.5, 1.0, 2.0, 5.0, 10, and 20 HU added to the hybrid model test bolus data. Performance of the predicted enhancement against the "true" enhancement as simulated by the hybrid-model for the twenty data sets were assessed using the metrics developed in 4.0—RMSE, Percent Difference in Max Enhancement (PDME), and Enhancement Difference Index (EDI).

It is common practice for the technologist performing the study to stop data collection from a test bolus scan shortly after the peak contrast enhancement. Reasons for stopping the data acquisition include concern of excess radiation exposure to the patient and a desire to make the study time short. Because the test bolus data record may contain only a few samples of data after peak enhancement, patient-specific contrast delivery algorithms must function in the presence of truncated data sets.

Experiments were conducted with truncated test bolus data vectors created with the simulated hybrid model to determine the effect of truncated test bolus scan data on the MLE parameter estimator. The vectors were truncated at durations of 20, 25, 30, and 35 seconds with no additive noise present. Next, simulated test bolus TECs were truncated at 25 and 35 seconds and noise was added. The AWGN were created with standard deviations of 0.1, 0.25, 0.5, 1.0, 2.0, 5.0, 10, and 20 HU. In all cases, the first data points of $y_{RH}^{Test,H}(n)$ and $y_{LH}^{Test,H}(n)$ were 5 seconds after the start of injection. The truncation times of 25 and 35 were chosen as specific test points because a 25 second acquisition duration can be expected in clinical practice and 35 seconds ensures the capture of the contrast peak and a number of samples after the peak in the left heart compartment for most procedures.

Estimator Performance Using Retrospectively Gathered Clinical Data

The estimator performance was assessed against clinical data collected during an IRB approved clinical trial at the Medical University of South Carolina (Somatom Definition DS, Siemens Healthcare Malvern Pa.). The data set and methods used to collect the data are described above. The test bolus TECs collected during the clinical trial were used to derive parameter estimates and the semi-automated aortic contrast enhancement data were used to compare the estimator's predicted output, identical to the methods described above.

During the clinical trial, scanner operators acquired the test bolus scan data by placing ROIs on the pulmonary trunk and the ascending aorta. Data collection started at 5 seconds after the injection of contrast started. Single-level scan acquisition was stopped by the operator two to four seconds after the peak of contrast enhancement in the ascending aorta was observed. The scanner software then processed the data and created TECs which were exported to data files and saved. Diagnostic scan enhancement profile data was extracted as described above.

An outline of the experimental methodology is: (1) Extract test-bolus TEC data; (2) Perform parametric estimation using MLE technique; (3) Generate predicted contrast enhancement using the diagnostic injection protocol from the clinical data set and the identified parameters from 2; (4) Extract the enhancement curve from the clinical data set; (5) Compare the predicted contrast enhancement against the clinical data (from the scan delay to the end of the scan acquisition).

Predicted outputs from the data-drive estimator were compared to the actual, clinical data using RMSE, PDME, and EDI.

All simulations and analyses were conducted with MATLAB (r2008b), the Optimization Toolbox (v4.1) and Simulink (v7.2).

Estimator Performance Using Model to Model Comparisons

The results from the model-model simulation are presented in Table 9 through Table 12. The resulting mean estimator bias for each parameter in the cardiopulmonary system, He2D, is listed in Table 9. The goodness of fit criteria used to gauge the performance of the estimators is the Mean Square Error between the predicted $\hat{y}_{LH}(n)$ and estimated yLH. The mean of MSE across the 30 simulations (and the square root of the MSE) are tabulated in addition to the percent bias for each parameter. Bias results for the He1D subsystem parameter estimation are summarized in Table 10.

Parameter estimation bias increased independently of the additive noise in the He2D subsystem, except for the $Q_{co}$, and $T_{LUNG}$ parameters at sampling periods of 0.5 and 1 sec/sample. The MSE of the fit appears to be independent of the sampling period because it increases similarly as a function of the noise sigma for all three sample periods. Parameter estimation bias increased in the He1D subsystem when data sampling periods exceeded one sec/sample. The MSE of the residual between the estimator's prediction and the true values increased as the noise contribution increased and for sampling periods greater than 1 sec/sample.

TABLE 9

Summary of parameter bias for $\theta_{He2D}$. Values are percent bias from the nominal values. MSE is the Mean Square Error of the residual error for the estimated and actual enhancement signal, $y_{LH}$

| Ts | $\sigma_{HU}$ | $V_{LH}$ | $V_{LUNG}$ | $Q_{CO}$ | $T_{LUNG}$ | MSE |
|---|---|---|---|---|---|---|
| 0.5 | 0 | −2.2 | 9.6 | 3.7 | −8.1 | 0.0 |
|  | 1 | −6.6 | 11.6 | 2.5 | −7.2 | 1.0 |
|  | 2 | −10.5 | 18.1 | 4.3 | −5.7 | 4.2 |
| 1 | 0 | −5.1 | 8.2 | 1.7 | −15.9 | 0.0 |
|  | 1 | −4.5 | 14.3 | 5.2 | −15.4 | 1.0 |
|  | 2 | −9.2 | 23.0 | 7.0 | −14.3 | 4.1 |
| 2 | 0 | −14.9 | 18.4 | 2.9 | −29.8 | 0.0 |
|  | 1 | −13.7 | 16.7 | 2.8 | −29.2 | 1.0 |
|  | 2 | −17.3 | 32.2 | 9.9 | −25.6 | 3.7 |

TABLE 10

Summary of parameter bias for $\theta_{He1D}$. Values are percent bias from the nominal values. MSE is the Mean Square Error of the residual error for the estimated and actual enhancement signal, $y_{RH}$

| Ts | $\sigma_{HU}$ | $V_{RH}$ | $V_{PER1}$ | $V_{PER2}$ | $T_{PER}$ | $Q_{PER}$ | $Q_{COr}$ | MSE |
|---|---|---|---|---|---|---|---|---|
| 0.5 | 0 | 0.0 | 3.0 | 12.5 | −0.4 | 0.4 | 10.0 | 0.0 |
|  | 1 | −10.2 | 2.1 | 22.8 | −0.4 | 0.3 | 9.9 | 1.0 |
|  | 2 | −4.4 | 3.1 | 19.1 | −0.4 | 0.4 | 10.1 | 3.8 |
| 1 | 0 | 0.0 | 2.7 | 12.5 | −0.9 | 0.4 | 10.0 | 0.0 |
|  | 1 | −4.5 | 2.3 | 17.4 | −0.9 | 0.3 | 10.0 | 1.0 |
|  | 2 | −4.5 | 1.3 | 16.2 | −0.9 | 0.2 | 10.1 | 3.7 |
| 2 | 0 | 35.1 | 1.9 | −90.0 | −1.0 | 0.3 | 10.7 | 2.4 |
|  | 1 | 34.9 | 3.3 | −90.0 | −1.0 | 0.5 | 10.6 | 3.4 |
|  | 2 | 38.1 | 3.3 | −90.0 | −1.0 | 0.5 | 10.8 | 5.3 |

Variance of the parameter estimates for both systems are shown in Table 8 and Table 9. Parameter estimation variance was the largest, for all sampling times, when the standard deviation of the noise contribution was 2 HU. The variance of the transport delay parameter, $T_{Lung}$, was the largest among all the parameters.

TABLE 8

Summary of parameter estimation variance for He2D

| Ts | $\sigma_{HU}$ | $V_{LH}$ | $V_{LUNG}$ | $Q_{CO}$ | $T_{LUNG}$ |
|---|---|---|---|---|---|
| 0.5 | 0 | 4.14E−07 | 4.01E−07 | 2.02E−05 | 4.92E−03 |
|  | 1 | 2.01E−02 | 1.88E−02 | 9.50E−01 | 2.30E+02 |
|  | 2 | 3.38E−04 | 3.08E−04 | 1.55E−02 | 3.79E+00 |
| 1 | 0 | 4.20E−06 | 4.01E−06 | 2.02E−04 | 4.69E−02 |
|  | 1 | 9.80E−03 | 9.02E−03 | 4.56E−01 | 1.14E+02 |
|  | 2 | 1.52E−04 | 1.35E−04 | 6.92E−03 | 1.84E+00 |
| 2 | 0 | 4.87E−05 | 4.23E−05 | 2.16E−03 | 5.16E−01 |
|  | 1 | 5.25E−03 | 4.67E−03 | 2.34E−01 | 5.61E+01 |
|  | 2 | 7.00E−05 | 5.80E−05 | 2.88E−03 | 8.32E−01 |

TABLE 9

Summary of parameter estimation variance for the He1D system

| Ts | $\sigma_{HU}$ | $V_{RH}$ | $V_{PER1}$ | $V_{PER2}$ | $T_{PER}$ | $Q_{PER}$ | $Q_{COr}$ |
|---|---|---|---|---|---|---|---|
| 0.5 | 0 | 6.23E−12 | 1.06E−09 | 7.83E−12 | 7.58E−08 | 5.96E−08 | 3.56E−10 |
|  | 1 | 3.83E−03 | 6.26E−01 | 4.55E−03 | 4.51E+01 | 3.55E+01 | 2.13E−01 |
|  | 2 | 5.85E−05 | 8.95E−03 | 7.09E−05 | 7.00E−01 | 4.99E−01 | 3.29E−03 |
| 1 | 0 | 3.50E−11 | 5.50E−09 | 4.39E−11 | 4.25E−07 | 3.09E−07 | 2.00E−09 |
|  | 1 | 1.88E−03 | 3.04E−01 | 2.32E−03 | 2.26E+01 | 1.70E+01 | 1.06E−01 |
|  | 2 | 2.83E−05 | 4.87E−03 | 3.47E−05 | 3.39E−01 | 2.71E−01 | 1.57E−03 |
| 2 | 0 | 2.22E−03 | 3.94E−01 | 3.59E−03 | 2.97E+01 | 2.19E+01 | 1.21E−01 |
|  | 1 | 3.14E−03 | 5.16E−01 | 5.08E−03 | 4.20E+01 | 2.87E+01 | 1.71E−01 |
|  | 2 | 1.87E−05 | 3.08E−03 | 3.05E−05 | 2.52E−01 | 1.70E−01 | 1.02E−03 |

Figure 18:
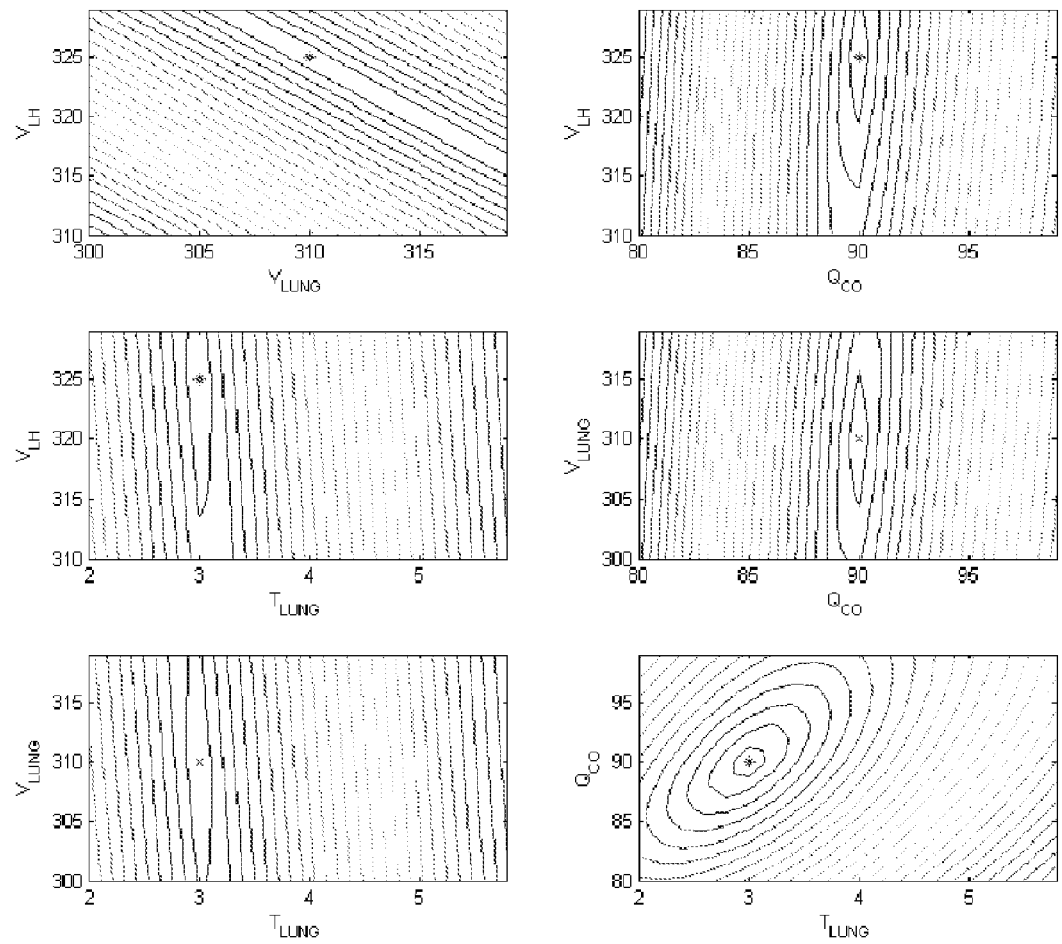
FIG. 18 illustrates contour plots of the $J_{LH}$ cost-function for parameter pairs for the He2D subsystem.
Figure 19:
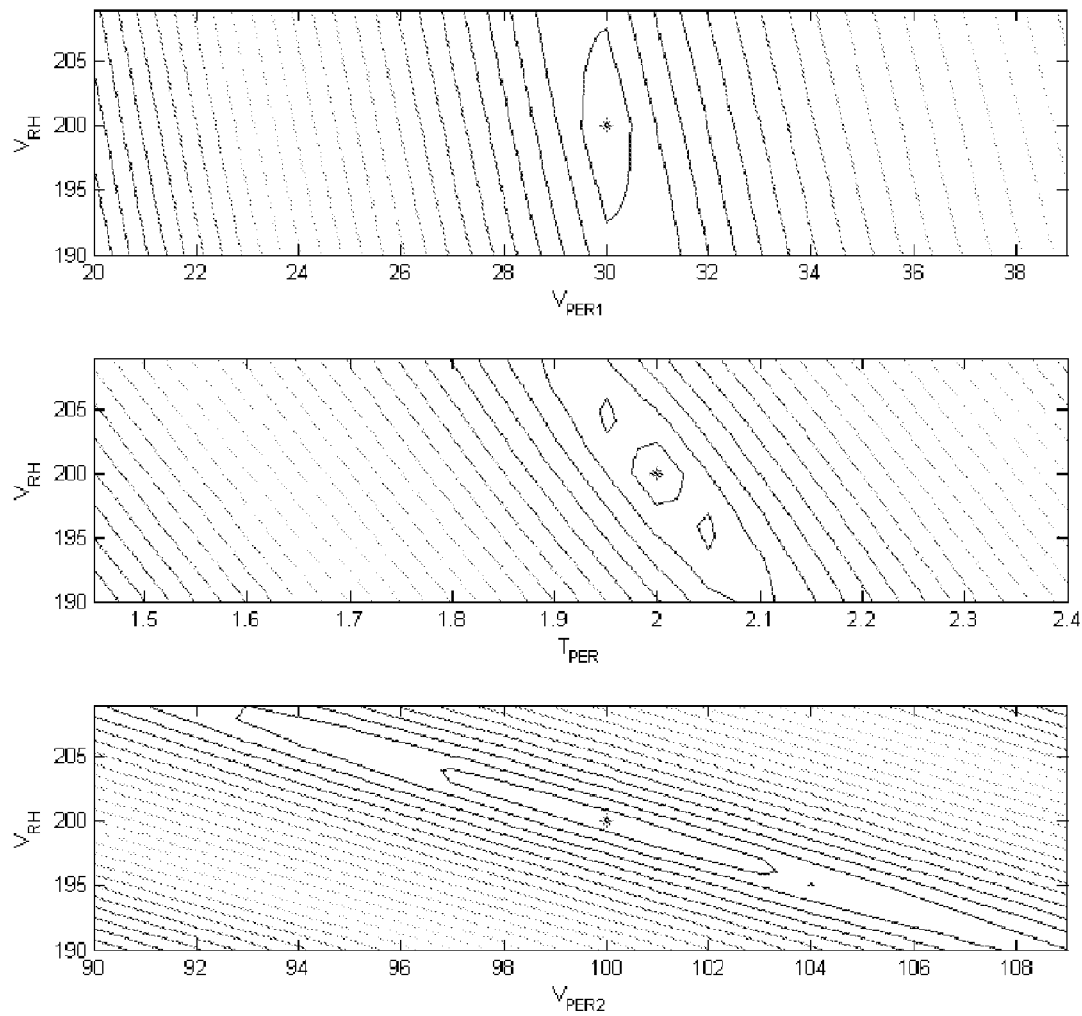
FIG. 19 illustrates contour plots showing projection of the $J_{RH}$ cost function as a function of parameter pairs.

Contour plots of the noise-free cost-functions for the left heart and right heart estimators (equations 44 and 45) were created for a range of parameters and are shown in FIG. 18 and FIG. 19. In each plot, two parameters were varied about a nominal value while the other parameters in the model were fixed. The resulting plots are 2D projections of the n-space hyperplanes defining the parameter space over the specified range. When the ellipsoids near the minimum of the solution space are elongated, this gives an indication that numerical solvers could have trouble converging on the true minimum and increased variance. The contour plots display single minima. Many of the parameter pairs exhibit long and narrow ellipses near the minimum—in particular the $V_{LH}$, $V_{LUNG}$ pair for the He2D subsystem.

Hybrid Model Parameter Estimation Results

Results from parameter estimation experiments using the hybrid model as the source of enhancement data for 20 subjects are presented below. In all 20 subjects, test bolus enhancement data were generated in the left and right heart compartments of the hybrid model using an input injection of 20 ml, 350 mgI/ml concentration contrast injected at 5 ml/s followed by 40 ml of saline. AWGN (standard deviation=2.5 HU) was added to the simulations response vectors and the test bolus enhancement signals were truncated at 35 seconds.

Figure 20:
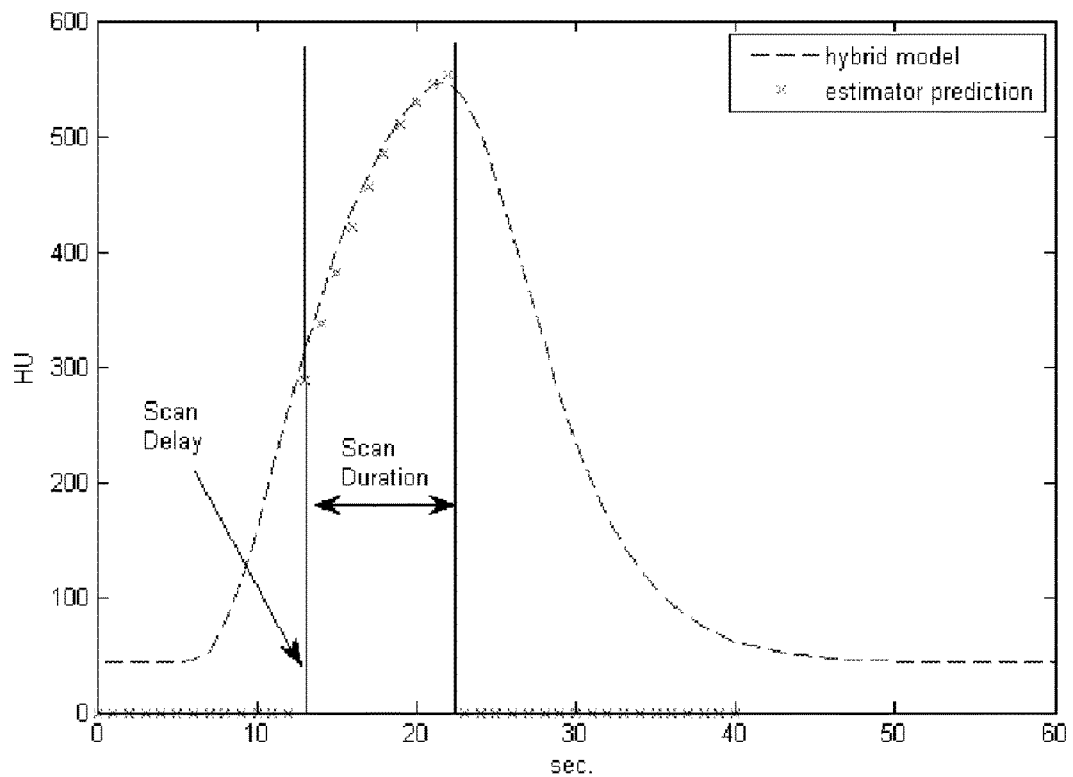
FIG. 20 illustrates hybrid model simulation for a diagnostic injection, using Subject 6 data, and estimated enhancement curve using the MLE methodology. The scan delay and scan duration values were extracted from the clinical data set for subject 6 as well.

The diagnostic injection for the simulated data set was a 75 ml bolus of 350 mgI/ml at 5 ml/s and followed by 40 ml of saline at 5 ml/s. Only data between the scan delay and the end of the scan were used in the comparisons between the estimated and simulated data (the scan delay and scan duration for each subject came from the clinical data set) as illustrated in FIG. 20. For all subjects, the data points between the two vertical lines were included in the computations of RMSE, PDME, and EDI as defined above.

The mean Root Mean Square Error between the simulated and estimated response was 7.78+/−4.40 HU. The average maximum percent difference between maximum enhancement (PDME) for both curves across the 20 subjects was 1.29+/−1.12%, and the mean Enhancement Difference Index was 1.57+/−1.16%.

Figure 22:
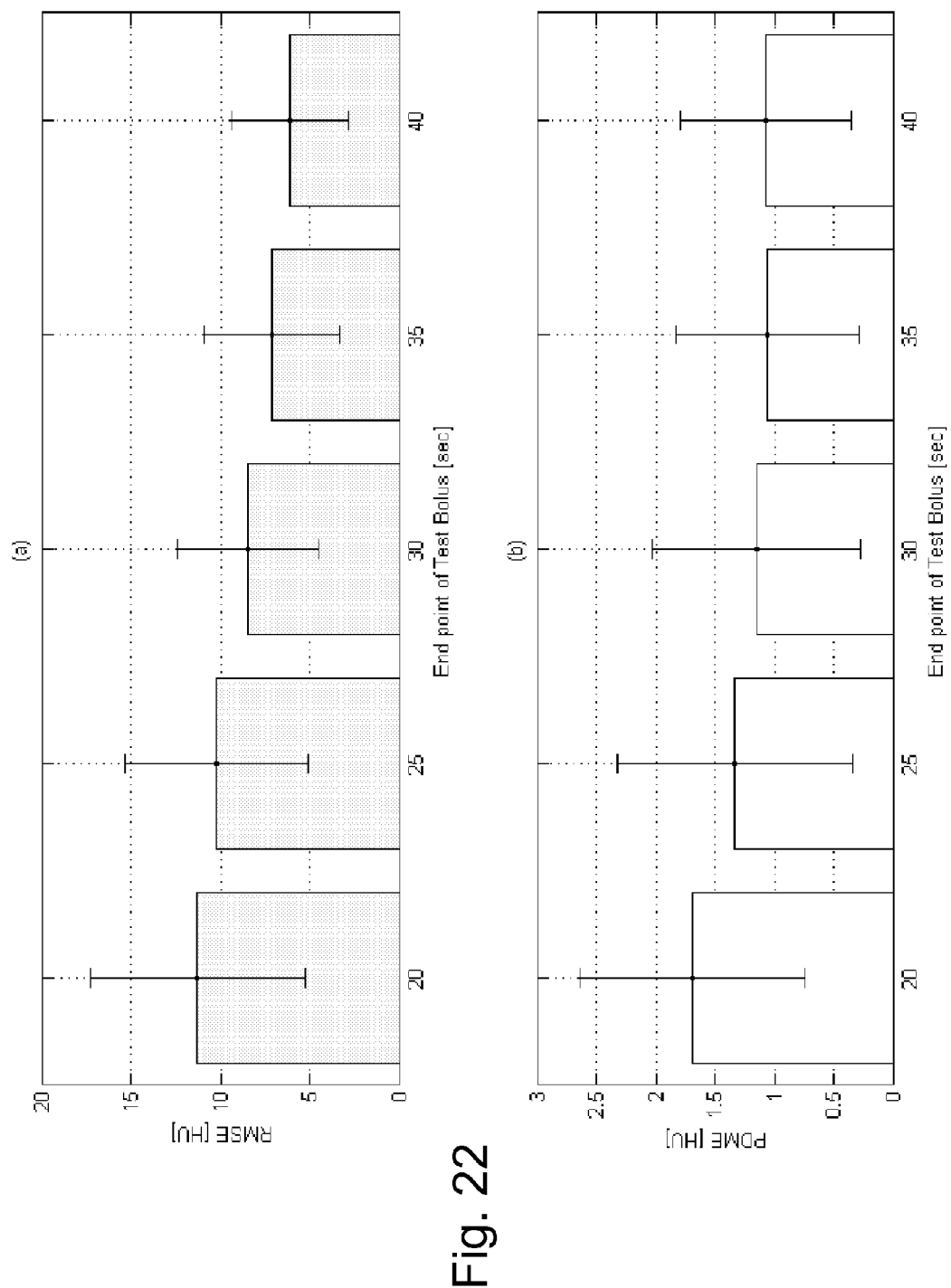
FIGS. 22A and 22B illustrate simulation results using the MLE methodology from hybrid model data. Each bar represents the mean across all 20 subjects when different length timing bolus data generated parameter estimates. Error bars indicate one standard deviation of the mean. a) Root Mean Square Error (RMSE) between simulation and predicted enhancements b) Percent Difference Maximum Enhancement (PDME) between simulation and predicted enhancement data.

The impact of test bolus data length and additive noise on the estimator's performance are shown in FIG. 22. Hybrid model simulations of the twenty subjects in the clinical set were performed using the same diagnostic injection for all subjects (75 ml of 350 mgI/ml concentration contrast at 5 ml/s followed by 40 ml of saline).

In the experiments that generated FIG. 22, the additive noise was zero. As the test bolus data vector decreased, the RMSE and PDME increased. It is not expected that scanner operators will acquire test bolus data many seconds after the appearance of the peak contrast opacification because of increased patient radiation exposure. Typical peak times in the ascending aorta from a test bolus injection are 17 to 24 seconds. The mean time to peak in the simulation cohort was 21.1+/−2.1 seconds. When the test bolus curves were truncated at 20 seconds, the peak enhancement was missing in most instances. Nonetheless, the estimator was still able to generate estimates of the system dynamics with 12 HU RMS error.

Figure 23:
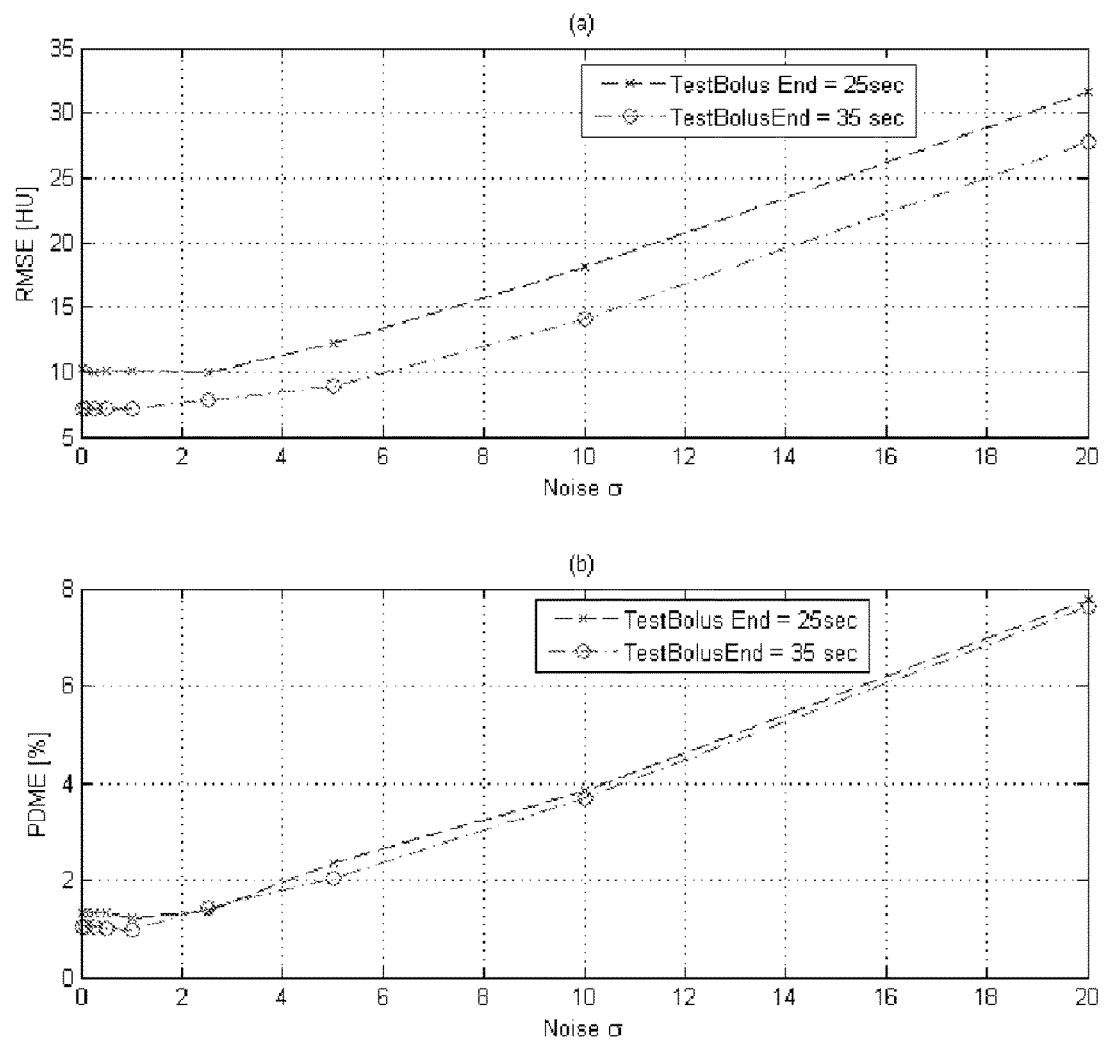
FIGS. 23A and 23B illustrate results demonstrating the impact of reduced length test bolus for identification and noise contribution on estimator performance a) RMSE between hybrid model simulation outputs and the estimator's predictions for test bolus data ending at 25 and 35 seconds b) PDME between the hybrid model simulation outputs and estimator's predictions for test bolus data truncated at 25 and 35 seconds.

FIG. 23 illustrates the performance of the estimator when additive noise between 0.1 and 20 HU is added to test bolus enhancement data truncated at 25 and 35 seconds. There is a consistent separation of approximately 3 HU for RMSE and there is less RMSE for longer test bolus enhancement curves. Prediction of maximum contrast enhancement is less sensitive to the length of test bolus measurement data vector. Typical noise on clinical test bolus enhancement data ranges between 2 and 10 HU. The difference in PDME between 25 and 35 second test bolus vectors is less than 0.5%. Both comparison metrics remain constant until the additive noise sigma exceeds 2 HU. Then the errors increase linearly.

Maximum Likelihood Estimation Results with Clinical Data

This section presents the ability of the estimator to predict contrast enhancement using the retrospective clinical data set. For each subject, the test bolus TEC data measured in the pulmonary trunk and the ascending aorta were used as inputs to the MLE algorithm. Comparisons between the estimated model (based on the MLE fitting) and the diagnostic scan contrast enhancement in the aorta were made. The injection protocol and scan parameters from the clinical data set were used in making the comparisons and only data points between the scan delay and the end of the scan were included in the computation of RMSE, PDME and EDI (as demonstrated with FIG. 20).

Figure 24:
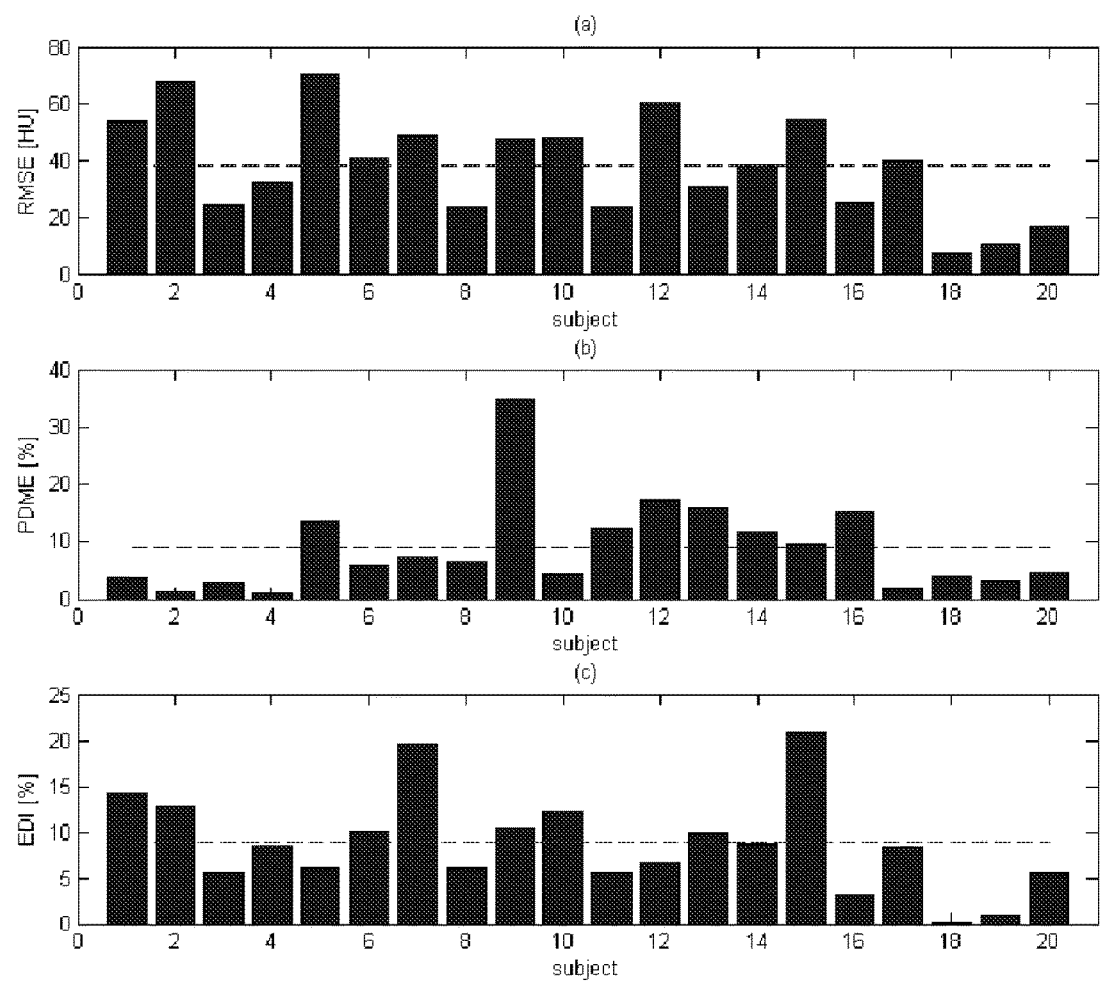
FIGS. 24A through 24C illustrate performance metrics of the MLE methodology using the clinical data set. Dashed horizontal lines indicate mean value.

FIG. 24 presents the results for all 20 subjects estimated using the test bolus data and the MLE technique. The horizontal, dashed lines indicate the sample mean for each performance metric. Subjects seven, nine and fifteen have the largest errors across all three categories. Numerical results from the analysis using the MLE are in Table 13 along with the prediction results when using the hybrid model parameterized with only subject demographic data. The MLE method resulted in lower mean RMSE, PDME and EDI (PDME was significantly different, p<0.05), a smaller range of data for all 3 metrics, and lower valued standard deviations. The maximum RMSE for the hybrid simulation was 142.3 HU while the RMSE was 70.5 HU using MLE.

TABLE 13

Summary results comparing the MLE and hybrid model prediction results

| | MLE Prediction Results | | | | | Hybrid Model Results | | | | |
|---|---|---|---|---|---|---|---|---|---|---|
| metrics | mean | stdev | min | max | median | mean | stdev | min | max | median |
| RMSE [HU] | 38.2 | 18.1 | 7.3 | 70.5 | 38.7 | 41.9 | 29.8 | 12.2 | 142.3 | 37.3 |
| PDME [%] | 8.9 | 8.1 | 1.0 | 35.0 | 6.3 | 14.6 | 10.2 | 0.8 | 42.1 | 14.5 |
| EDI [%] | 8.8 | 5.4 | 0.1 | 21.0 | 8.4 | 10.8 | 11.0 | 2.1 | 45.8 | 5.3 |

Figure 25:
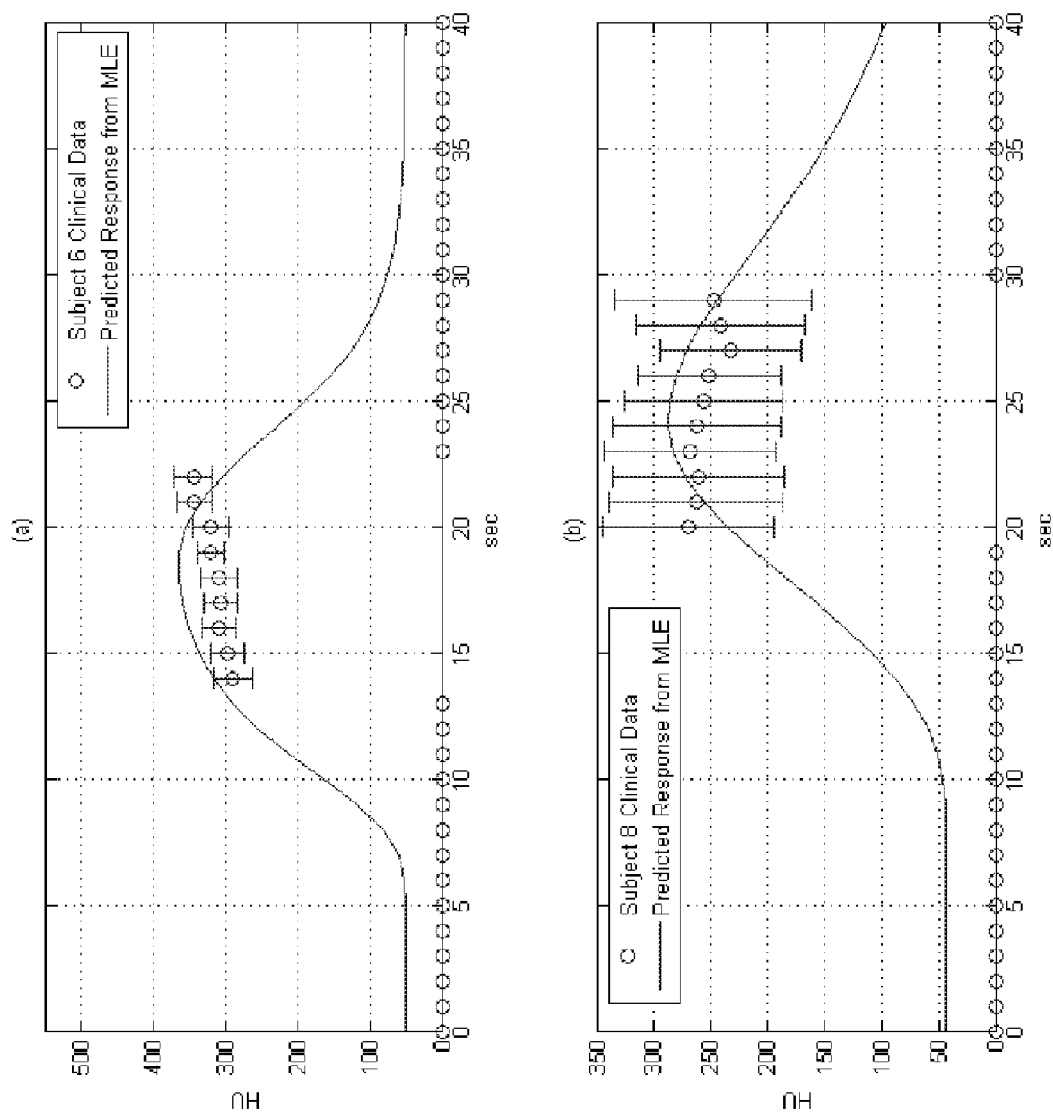
FIGS. 25A and B illustrate MLE prediction results using clinical data for (a) subject 6 and (b) subject 8. Error bars indicate plus/minus one standard deviation of the mean, as measured in the aorta at the particular z-axis location.

FIG. 25 plots the predicted contrast enhancement and diagnostic contrast enhancement for two subjects (6 and 8). The predicted enhancements for these patients using the hybrid model were presented in FIG. 9. Their prediction performance was the worst among all 20 subjects. Using the test bolus TEC from the clinical data and the MLE methodology, better contrast enhancement prediction was achieved for these two subjects (RMSE of 39 HU vs. 160 HU for subject 6 and 21 HU vs. 57 HU for subject 8—MLE and hybrid results).

Figure 26:
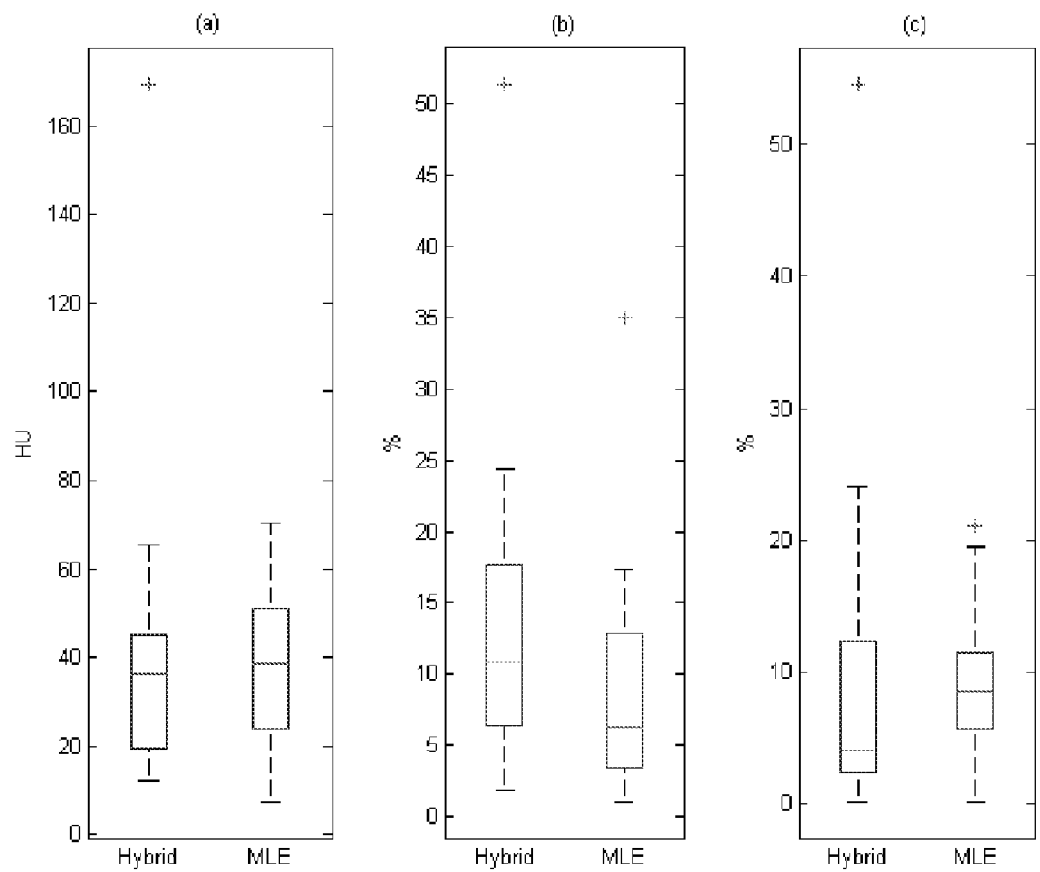
FIGS. 26A through 26C illustrate box-and-whisker plots for results of predicted enhancements using the hybrid model (Hybrid) and the MLE methodology (MLE) to predict contrast enhancement in the clinical data set (a) RMSE (b) PDME (c) EDI.

FIG. 26 presents box-whisker plots graphically comparing the results from the hybrid model and MLE across the 20 subjects. The horizontal line in each box indicates the median data value and the edges of the vertical boxes indicate $1^{st}$ and $3^{rd}$ quartile of data.

Non-Parametric Identification

The methodology and results (simulation and clinical data) for embodiments of a non-parametric identification technique for prediction of contrast enhancement using the test-bolus paradigm are set forth below. A truncated Singular Value Decomposition method is introduced, its performance on simulation and retrospective clinical data are presented and a comparison to the MLE methodology is presented.

As describe above, a parametric identification methodology was developed for estimating and predicting contrast enhancement on an individual basis using test-bolus enhancement data to parameterize a reduced-order pharmacokinetic model. Alternatively, a non-parametric (or model-independent) approach that is also dependent on data from a test-bolus injection and scan, but, for example, requires data from only one scan location, can be used. In several studies, the ascending aorta is used as the scan location. One advantage of a non-parametric approach is that assumptions, such as the model structure and order, are not required. The assumption that the underlying system dynamics can be modeled as a LTI system can, for example, be made, however.

The non-parametric methodology poses the contrast enhancement problem as an inverse problem in which the output (image data from the ascending aorta upon administration of a test-bolus) and the input (test bolus Iodine administration profile) are known. A regularization method, the truncated Singular Value Decomposition (tSVD) as described below is used to estimate the impulse response (or residue function) of the drug and cardiopulmonary system. A clear to those skilled in the art, other methods can be used to estimate the impulse response.

A truncation index that adapts to measurement noise and that balances residual error and solution error can be selected for the tSVD to produce the desired results. As discussed in Appendix 1 hereof at the end of this description, the adaptive truncation index and the tSVD is more robust to data variation than the Fleischmann/Hittmair Fourier deconvolution methodology because in that approach only a low pass filter with a fixed cutoff frequency was used.

Figure 27:
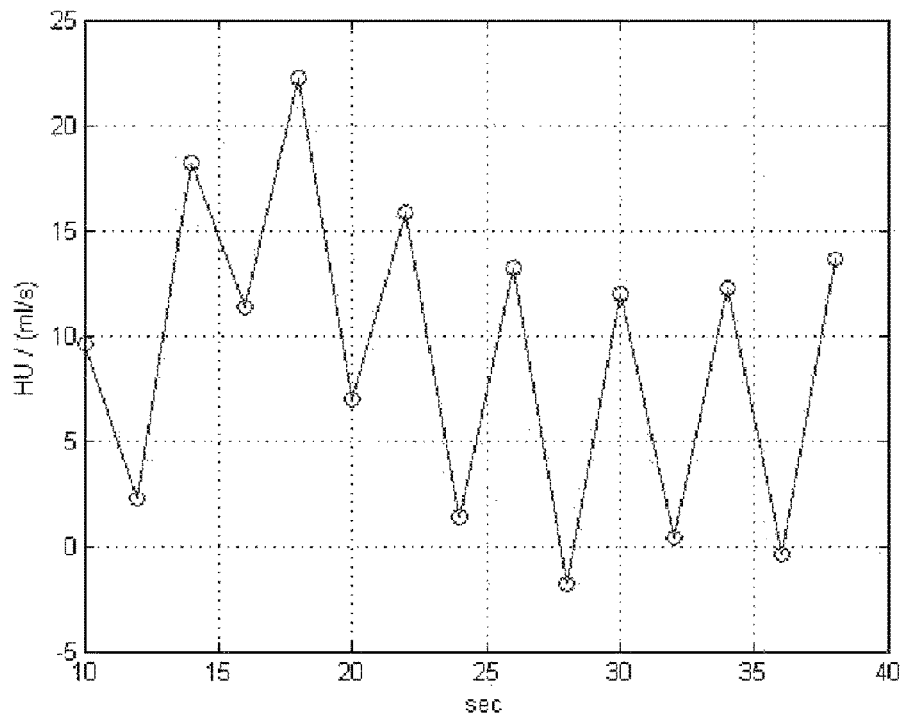
FIG. 27 illustrates a solution for the impulse response, $h_{sys}$, using subject 7 data and matrix division (least squares solution).

Benefits of a regularization technique, like tSVD, when creating predictive contrast enhancement techniques is demonstrated with an example. An estimated impulse response, $h_{sys}$, for Subject 7 in the clinical data set (test bolus TEC data) was generated by using standard linear least squares (MATLAB's matrix left division operator). The enhancement dynamics were defined by the matrix product of the impulse response and a lower triangular, Toeplitz matrix formed from the input function A1 of Appendix 1: $y_{LH} = U_{inj} h_{sys}$. FIG. 27 plots a linear least squares solution for $h_{sys}$, using the clinical enhancement data from the left heart generated from a test bolus injected at 5 ml/s for 20 seconds (350 mgI/ml concentration contrast). Clearly evident are the oscillations introduced by the measurement noise. The linear least squares method inability to filter the noise prohibits the robust estimation of the system impulse response.

Figure 28:
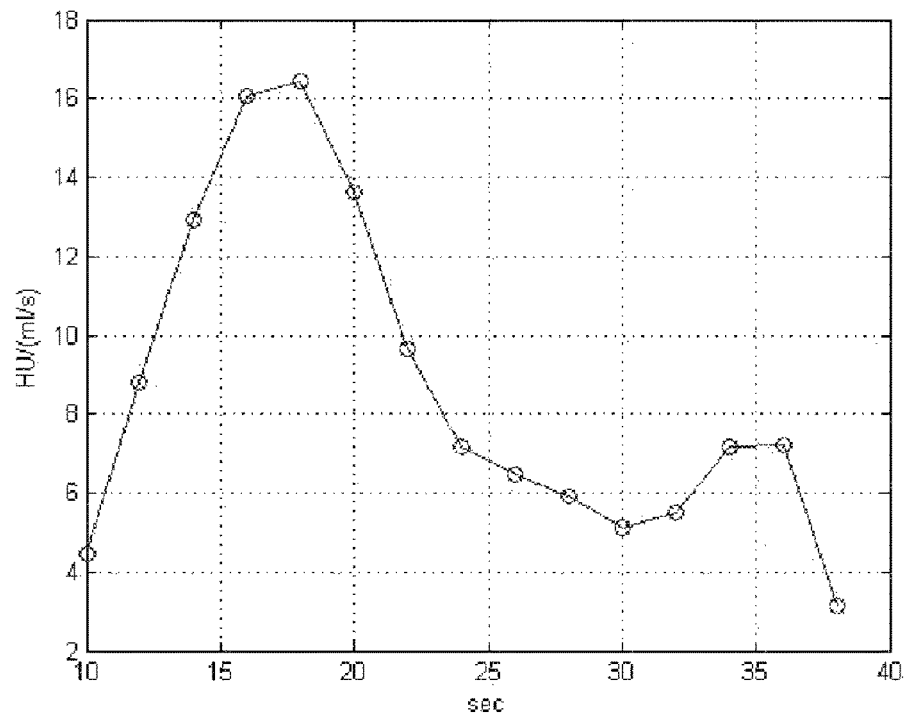
FIG. 28 illustrates estimated impulse response for subject 7 data using the tSVD method.

Contrasted with the impulse response estimate using simple Least Squares is the plot in FIG. 28 which is an estimated impulse response for Subject 7 using the tSVD methodology developed in this section. The detailed algorithm for creating a contrast enhancement prediction using the tSVD is presented below in Table 14.

TABLE 10

Non-parametric estimation algorithm

1. Acquire and process test-bolus enhancement data from the Left Heart compartment (ie: Ascending Aorta), $y_{LH}^{Test}$ (n) generated by a test-bolus injection, $u_{inj}(n)$.
2. Define the system in matrix notation as in equation A1 of Appendix 1:
   $y_{Test} = H \cdot U_{Test}$
   a. Construct a Toeplitz Matrix $U_{temp}$ from the scalar input function, $u_{Test}(n) = Q_{inj}C_{inj}[u(n) - u(n-N_{inj})]$ where $Q_{inj}$, $C_{inj}$, and $N_{inj}$ are the flow rate, concentration and duration of the test bolus injection.
   b. $U_{Test}$ is the lower triangular portion of $U_{temp}$
3. $H = U_{Test}^{-1} \cdot y_{Test}$
4. Decompose $U_{Test}$ into its singular vectors (U, V) and singular value matrix (Σ) by the Singular Value Decomposition:
   a. $H = (U \Sigma V^T)^{-1} y_{Test}$
5. The columns of H are (per equation A4 of Appendix 1):
   a. $h_k = \sum_{i=1}^{k} \frac{u_i y}{\sigma_i} v_i$
6. Determine the system impulse response estimate, $h_{sys}$, by selection of an optimal truncation index, k. Select k by the method of:
   a. Piecewise linear-fit method. Koh TS, W.X., Cheong LH, Lim CCT, *Assesment of Perfusion by Dynamic Contrast-Enhanced Imaging Using a Deconvolution Approach Based on Regression and Singular Value Decomposition*. IEEE Trans Med Imaging, 2004. 23(12): p. 1532-1542.
   b. Adaptive pruning method of Hansen, P.C., *The truncated SVD as a method for regularization*. BIT, 1987. 27: p. 534-55.
7. Compute RMSE between $\hat{y}_{Test} = h_{sys} \cdot u_{Test}$ and $y_{Test}$
8. Compute estimate of diagnostic enhancement $\hat{y}_{Diag} = h_{sys} \cdot u_{Diag}$ for an arbitrary injection input, $u_{Diag} = Q_{Diag}C_{Diag}[u(n) - u(n-N_{Diag})]$ Two approaches for selecting the truncation index, k, in the singular value decomposition were investigated and implemented—the linear piece-wise fit method of Koh et al and the adaptive pruning L-curve criterion of Hansen et al.

Koh T S, W. X., Cheong L H, Lim C C T, *Assesment of Perfusion by Dynamic Contrast-Enhanced Imaging Using a Deconvolution Approach Based on Regression and Singular Value Decomposition.* IEEE Trans Med Imaging, 2004. 23(12): p. 1532-1542. Hansen, P. C., *The truncated SVD as a method for regularization.* BIT, 1987. 27: p. 534-55. The truncated singular value decomposition method provided in the Regularization toolbox, freely distributed on the Internet, (tsvd.m) was used to create impulse response estimates. Hansen, P. C., *Regularization tools: a MATLAB package for analysis and solution of discrete ill-posed problems.* Numer. Algorithms, 1994. 6: p. 35.

As presented in Appendix 1, the Koh method computes the truncation index by approximating the Picard plot with a piece-wise, linear function. A Picard plot is a log plot of the Fourier coefficients against an index variable ranging over the length of the data samples in the observation vector, $y_{LH}^{Test}$. The system of linear equations for the problem is:

$$U_{inj} \cdot h_{sys} = y_{LH}^{Test} \quad (52)$$

which is similar to the standard notation of Ax=b for a linear system. The Fourier coefficients are the absolute values of the product of the left singular vectors (columns of the left singular matrix from a singular value decomposition) and the observation vector $|u_i^T y_{Test}|$. The coefficients for the approximation to the Picard plot were determined by solving:

$$\beta_{lsq} = \frac{X^T Y}{X^T X} \quad (53)$$

where Y is the vector of Fourier coefficients, $|u_i^T y_{Test}|$. The X matrix was formulated as described in Appendix 1. MATLAB's internal matrix multiplication and inversion utilities were used to solve equation 53. Finally, a vector consisting of the sum of squared errors, SSE indexed by k, was constructed:

$$SSE_k = (Y - X\beta_{lsq})^T (Y - X\beta_{lsq}) \quad 54$$

Per Koh's algorithm, the optimal truncation index was selected as the index belonging to the element of the SSE array with the smallest value.

The adaptive pruning algorithm for determining the truncation index is described fully in Hansen, P. C., T. K. Jensen, and G. Rodriguez, *An adaptive pruning algorithm for the discrete L-curve criterion.* Journal of Comput and Appl Math, 2007. 198: p. 9. In summary, the technique constructs a discrete L-curve, which is simply a plot of the solution norm $\|h_{sys}\|_2^2$ versus the residual norms $\|Uh_{sys} - y_{Test}\|_2^2$. The Hensen adaptive pruning algorithm searches for the L-curve's corner by systematically removing points from the discrete L-curve in two stages. The corner function in Hansen's Regularization Toolbox implements the pruning algorithm, and it was used to compute the truncation index, k. Hansen, P. C., *Regularization tools: a MATLAB package for analysis and solution of discrete ill-posed problems.* Numer. Algorithms, 1994. 6: p. 35.

Simulations of the hybrid model were used to determine the preferred methodology to compute the truncation index. The same twenty subjects simulated in section 5.1.4.2 were simulated, using a fixed flow rate and volume of contrast (5 ml/s of 350 mgI/ml contrast for 4 seconds) as the injection for all the simulations. Two simulation runs were completed. The first used the L-curve adaptive pruning algorithm to determine the optimal truncation index for the tSVD and the second used the Koh method to select the truncation index. A comparison of RMSEs between the two methodologies was performed to determine the preferred method.

Mean values for the three performance metrics, RMSE, PDME and EDI across the 20 subjects are given in Table 15. The Koh method produces predicted enhancement with 11% less RMS error, 22% less maximum difference error, and 10% less average EDI percentage. Also, the resulting impulse responses and reconstructed test bolus curves were smoother when the Koh technique computed the truncation index. Also, the Koh method computed lower valued truncation indices than the adaptive pruning algorithm for this problem. The Koh method was selected, based on these results, for the subsequent experimentation.

TABLE 11

Simulation analysis results comparing the two methods of determining the tSVD truncation index

| Truncation Method | Mean RMSE [HU] | Mean PDME [%] | Mean EDI [%] |
|---|---|---|---|
| Adaptive Pruning | 7.9 | 2.2 | 1.9 |
| Koh | 7.0 | 1.7 | 1.7 |

Evaluation Methods

One set of experiments used the hybrid PBPK model to generate enhancement data and was conducted to determine the performance of the non-parametric estimator in the presence of additive noise and with truncated test bolus measurement vectors. Next, retrospective clinical data (the same set as used with the parametric MLE technique described above) were used to ascertain the performance of the non-parametric technique with human subject data. The performance metrics were then compared to those from the parametric method described above.

Hybrid Model Simulation Experiments

Once again, a set of 20 subjects were numerically simulated using the hybrid PBPK model and the patient demographics from the clinical data set using the same methodology described above. Only the test bolus response in the left heart compartment, $y_{LH}^{Test}(n)$, was used in generating the non-parametric estimate of the system. The block of 20 subjects had AWGN added to the test bolus data (0, 0.1, 0.25, 0.5, 1, 2, 5, 10, 20 HU). The impact of the test bolus vector on performance was investigated by performing simulations with variable length test bolus enhancement data.

Clinical Data Experiments.

Experiments using the retrospective clinical data set were conducted, again using the methods described above. The same performance metrics, RMSE, PDME and EDI, were used to describe the performance of the estimation and prediction technique. Comparison to the results using the MLE methodology was also conducted.

Figure 21:
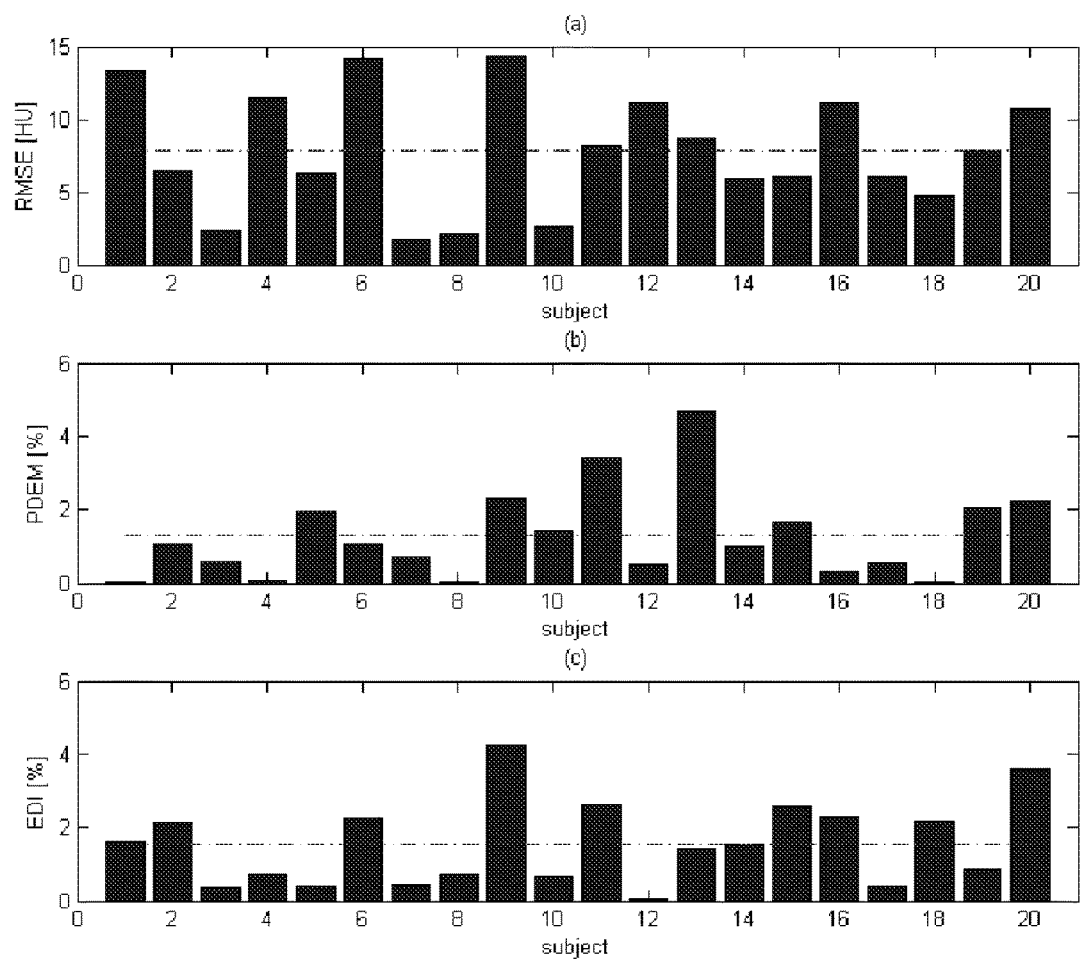
FIGS. 21A through 21C illustrate results from the hybrid model simulation set using the Maximum Likelihood Estimator. a) Root Mean Square Error between 20 patients simulated with the hybrid model and the predicted enhancement b) The Predicted Difference Maximum Enhancement between the simulated hybrid model data and the estimated response c) Enhancement Difference Index results. Dashed lines represent the mean value for each data set.
Figure 29:
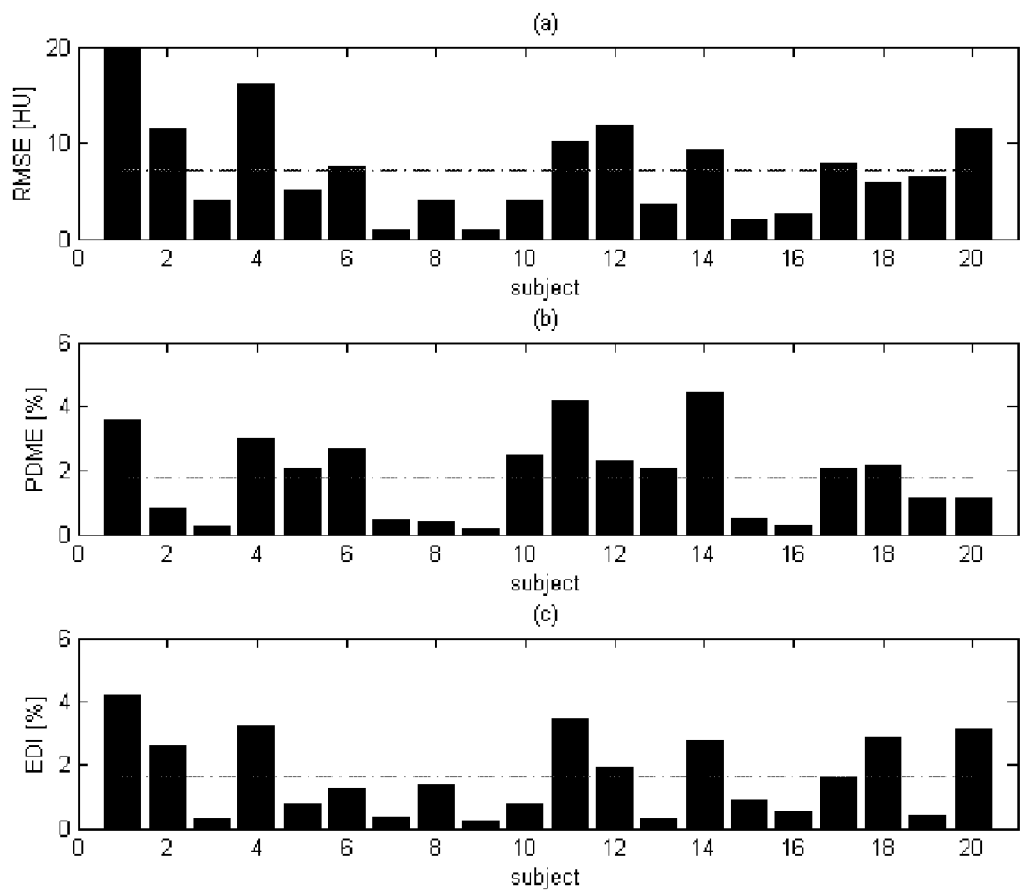
FIGS. 29A through 29C illustrate performance metrics for the tSVD estimating left-heart enhancement with the hybrid model data. The horizontal, dashed blue line represents mean (a) Root Mean Square Error (b) Percent Difference Maximum Enhancement (c) Enhancement Difference Index.

The mean RMSE, PDME and EDI results for all 20 subjects using tSVD to predict contrast enhancement using simulated data from hybrid model simulation are presented in FIG. 29. Comparisons were made between the simulated and predicted enhancement in the left heart compartment when the same diagnostic injection protocol was delivered to all 20 simulated patients. These results are comparable to those in FIG. 21 where the MLE method estimated the contrast enhancement for these 20 subjects. The RMSE (mean+/−standard deviation) between the enhancement values was 7.3+/−5.1 HU, the PDME was 1.8+/−1.3%, and EDI was 1.6+/−1.3%. Using the MLE with these same data resulted in RMSE, PDME, and EDI of 7.78+/−4.40 HU, 1.29+/−1.1%, and 1.57+/−1.2% (see FIG. 21).

Figure 30:
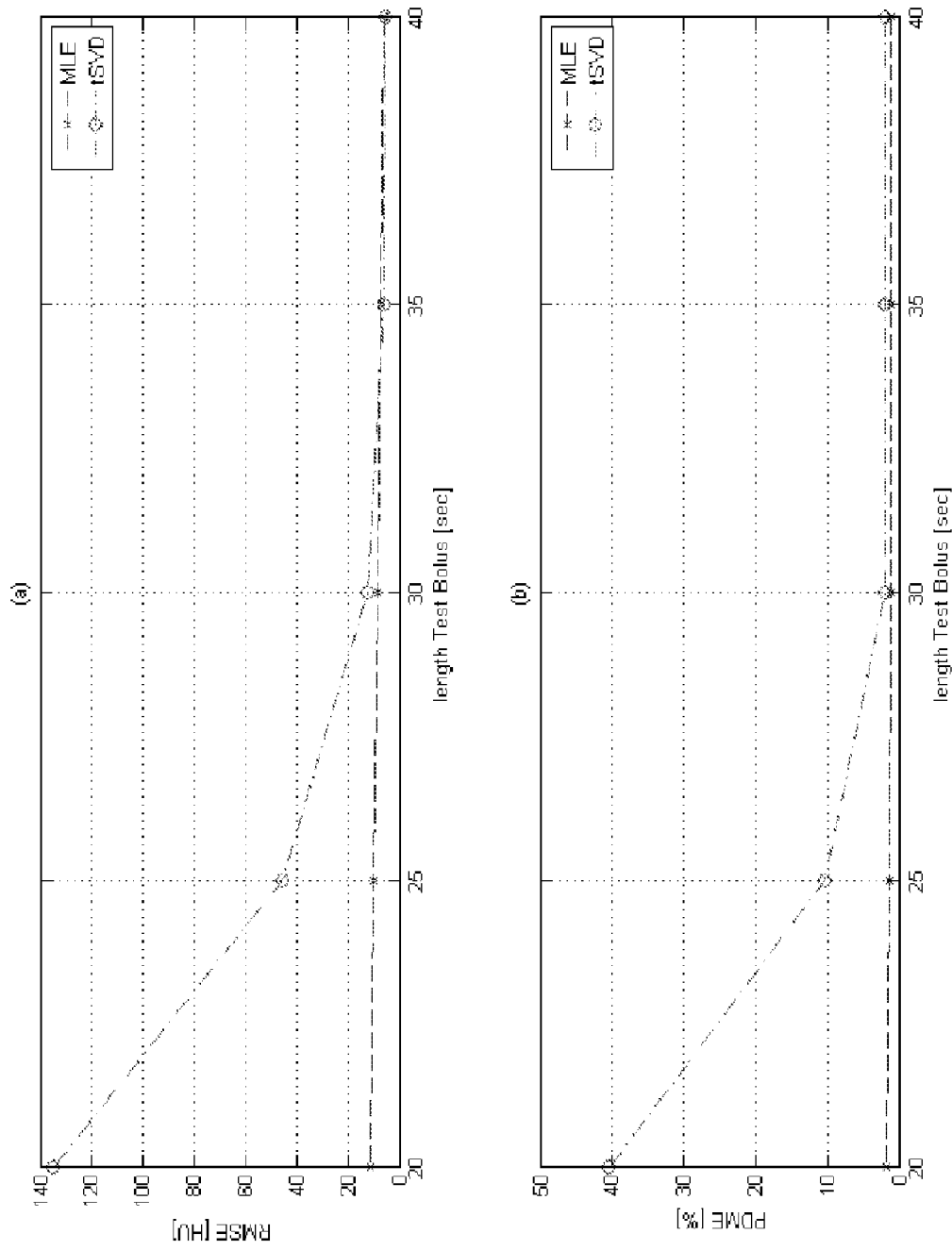
FIGS. 30A and 30B illustrate hybrid model simulation results comparing the performance of the MLE and tSVD estimation methodologies as the length of the test bolus vectors ranged from 20 to 40 seconds. In all simulations, there was no additive noise present on the test bolus data (a) RMSE results (b) PDME results.

The impact of variable length test bolus enhancement data (20 to 40 seconds) on tSVD estimator performance are presented in FIG. 30. The data are average values taken across all 20 subjects at each test bolus enhancement vector length. No noise was added to the test bolus enhancement data for these experiments.

Figure 31:
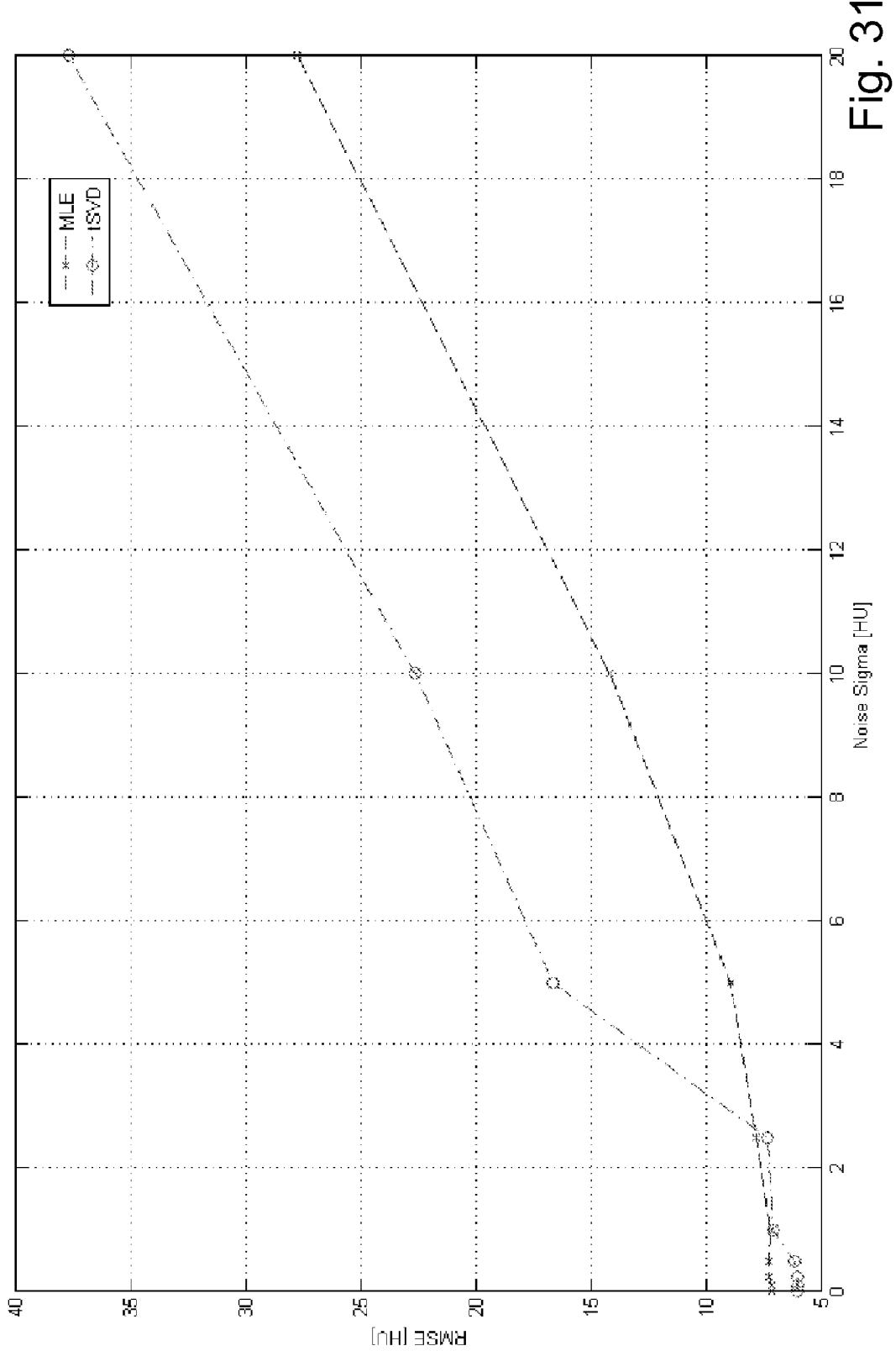
FIG. 31 illustrates simulation results for test bolus length of 35 seconds but when AWGN (sigma) added to the test bolus data varied from 0 to 20 HU. Each data point is the mean of 20 simulated subjects using the hybrid model.
Figure 32:
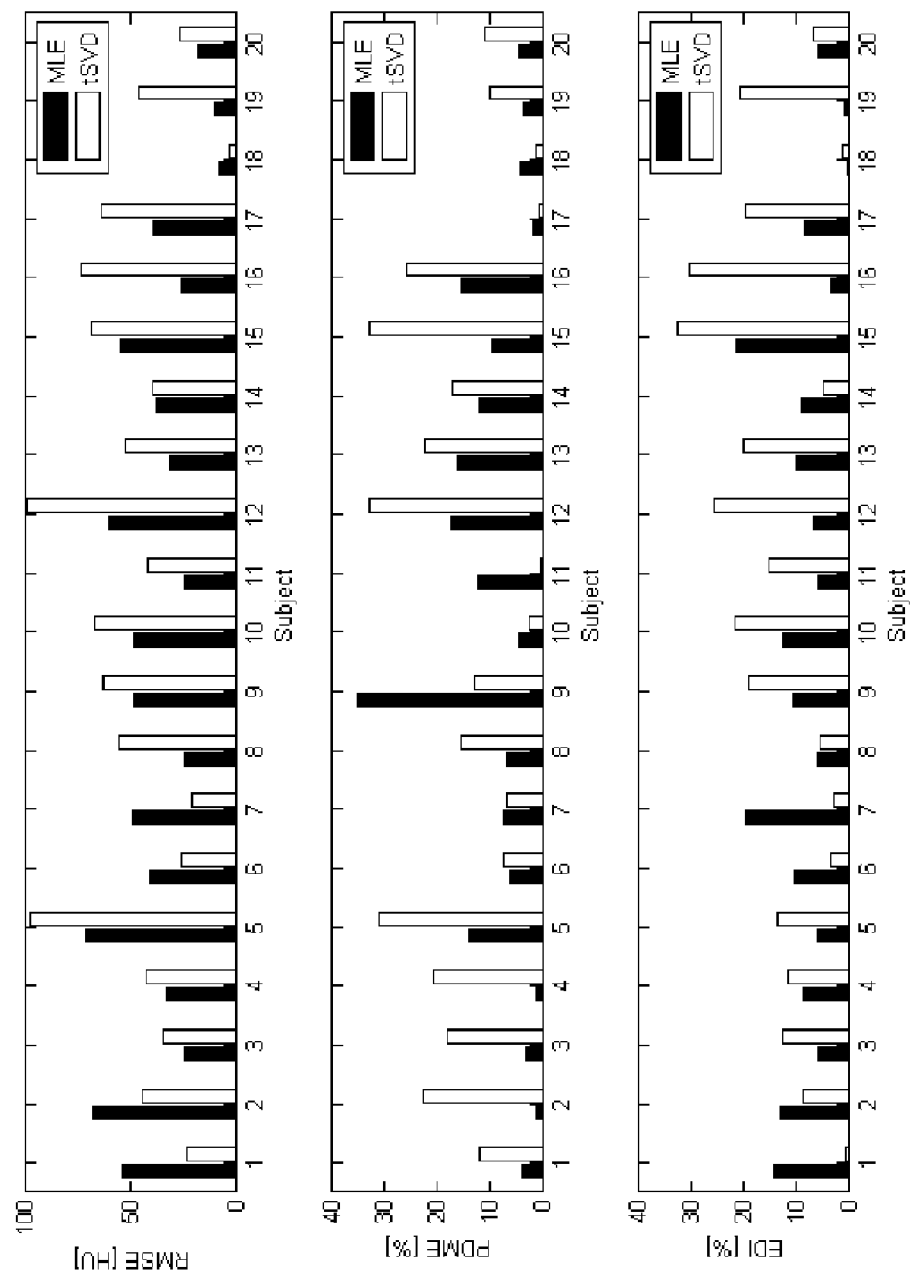
FIG. 32 illustrates results from the two estimation methodologies, MLE and tSVD, using the clinical data set test bolus vectors and diagnostic enhancement data (a) RMSE (b) PDME (c) EDI.

The performance of the tSVD estimator when the test bolus enhancement data were corrupted with AWGN is presented in FIG. 31. Twenty simulations were performed using the demographic data from the clinical data set. Test bolus vectors were truncated at 35 seconds for all the simulations. Additive Gaussian noise with standard deviations of 0, 0.1, 0.25, 0.5, 1.0, 2.5, 5.0, 10 and 20 HU were added to the test bolus data for each block of 20 subjects. The average RMSE values for the tSVD and MLE estimators are plotted together in the figure. Note that when the additive noise was greater than 2.5 HU, the MLE performed better. For low levels of additive noise (0.1, 0.2, 0.5, and 1.0 HU sigma), the tSVD performed slightly better.

Comparative results for the tSVD and MLE methodologies, using the clinical data as the source of the test bolus and diagnostic enhancement data, are given in FIG. 31. The MLE estimation technique produced enhancement estimates with lower RMSE, PDME and EDI in 14/20, 13/20, and 13/20 subjects, respectively. Summary results for the three performance metrics RMSE, PDME, and EDI were (mean+/−SD): 49.1+/−24.7 HU, 14.9+/−10.5%, and 13.6+/−9.6%.

Figure 33:
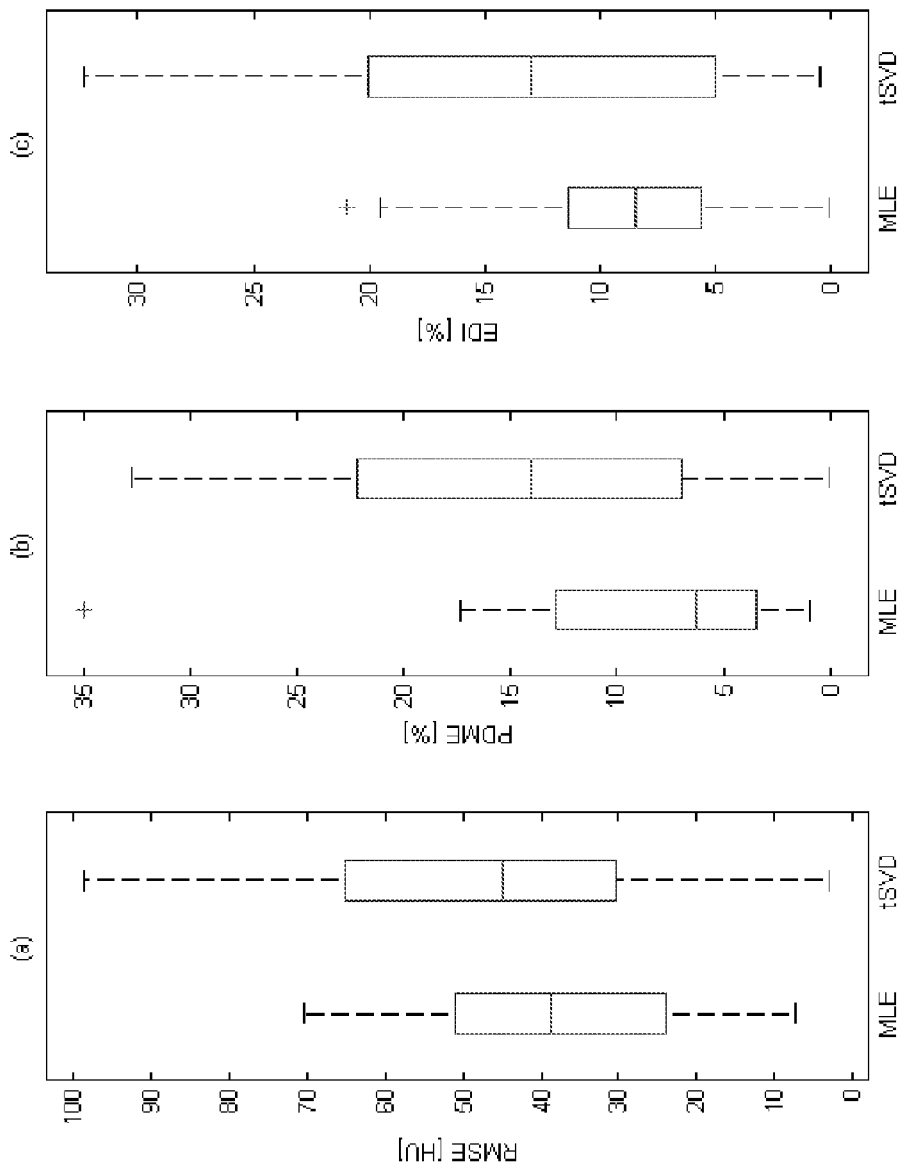
FIGS. 33A through 33C illustrate box and whisker plots comparing the two estimation techniques using the clinical data set as the basis of comparison. (a) RMSE (b) PDME (c) EDI.
Figure 34:
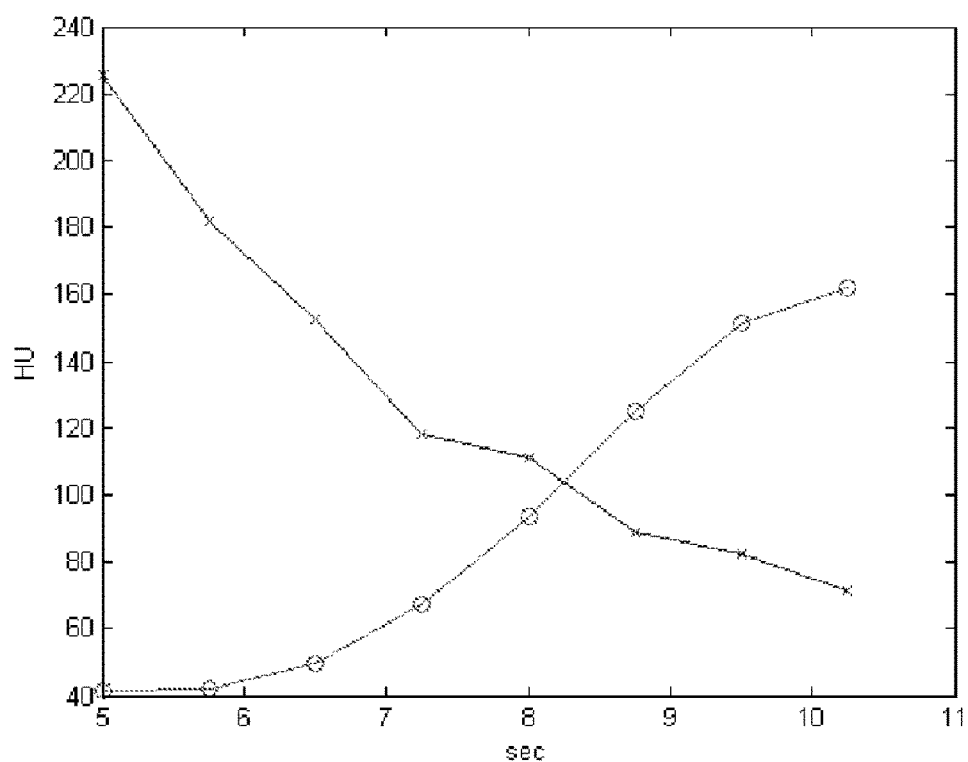
FIG. 34 illustrates a test bolus for one subject (Subject 15) in the clinical data set. The curved marked with the "x"'s is the pulmonary artery TEC and the curve annotated with circles is the ascending aorta TEC.

The box and whisker plot in FIG. 33 show that the MLE method produced lower RMSE, PDME and EDI across the 20 subjects, but the differences were not statistically significant. It is apparent from the box-whisker plot that the estimated enhancements using tSVD resulted in wider variability around the median. Mann-Whitney U tests on the three sets of metrics reveals a significant difference only for the PDME results (p<0.05).

In some cases, however, statistical significance for all three metrics was demonstrated between the two methods. Subjects 5, 12, and 19 had significantly greater mean RMSE and PDME with tSVD than MLE (p<0.05, Sign-Rank test). These subjects showed the greatest discrepancy between the two data-driven estimation techniques.

The results indicate that the MLE method is superior to the tSVD method for predicting patient-specific contrast enhancement, especially when considering the constraints and practicalities of actual clinical practice. Specifically, the MLE is more robust to changes in test bolus enhancement data vector lengths, it has favorable noise rejection characteristics, and it provides parametric estimates of physiologic variables that could have utility in quantifying the status of the patient (eg: cardiac output estimation). If test bolus enhancement data are available that extend several seconds beyond the peak of contrast enhancement, then the tSVD and MLE methods perform similarly. In clinical practice, however, it is difficult to ensure that data acquisition during the test bolus scan will routinely contain data points after the peak is achieved.

Whereas the tSVD appears to have superior noise immunity for low levels of AWGN, the MLE has better noise immunity when the test bolus data are corrupted with large values of AWGN. The tSVD has a main advantage in that only one TEC curve is required for estimation and it is computationally less burdensome. However, the optimization within the MLE was performed in seconds using a Pentium III (not exceptional hardware) and widely available numerical methods.

Parametric bias and variance were favorable using the MLE. Visualization of the solution space also revealed well defined minima, albeit they were long and broad in some instances. There is evidence, therefore, to support that the cost function used in the MLE are adequate for computing the required parametric estimations for patient-specific contrast enhancement prediction based on the performance metrics when the hybrid model simulation data tested the MLE method.

Poor concordance in some cases between predicted and clinical data can be attributed to noisy and/or incomplete test bolus TECs from the clinical data set. The large error for subject 15 in both the MLE and tSVD experiments can be directly attributed to an incomplete test bolus curve. Subject 15's TEC is plotted in FIG. 24. Peak enhancement values in the pulmonary artery and ascending aorta were not captured. Despite these missing features, the MLE was still able to produce a contrast enhancement with morphology not too dissimilar from the clinical data, albeit shifted in time. The three performance metrics using the tSVD on this subject, however, were all well above the sample mean, illustrating the impact of limited test bolus data on the tSVD's performance.

The second worst EDI score for the MLE outcome was for subject 7. Inspection of the diagnostic enhancement data and the predicted enhancement profile shows that the enhancement prediction tracks the diagnostic, clinical data but is offset by 40-80 HU. Perhaps the baseline attenuation for this subject was lower than 50 HU.

Subject five had the highest RMSE error for the MLE data. There is general agreement between the predicted contrast enhancement and the clinical data for this subject, but the predicted enhancement profile has an upslope that starts several seconds too early. Perhaps the test bolus data were improperly timed or the clinical data set scan delay was improperly recorded. The highest RMSE results with the tSVD predictions were seen with subjects 5, 12, and 16. Subject 15 had the worst performance for all three metrics, attributable to the poor test bolus data for that subject.

In general, the clinical scan data used in this chapter are not ideal for testing the identification methods because they were generated with diagnostic injection protocols having different flow rates from the test bolus injection protocol. As discussed above, injection flow rates alter the peripheral compartment flow rate. The dynamics for the model made by fitting the test bolus at one flow rate during the test bolus injection and scan can be slightly different for a diagnostic injection with a different flow rate. An ideal diagnostic injection protocol for comparing the identification methods would be similar to the one used with the hybrid model comparisons—a fixed flow rate and same volume for all patients.

The method by which the diagnostic enhancement data were generated must also be considered a limitation of the analyses because the TECs were not generated from a single-level scan at the same level from which the timing bolus TEC was constructed. Rather, the data were constructed from the spatiotemporal distribution of contrast in the aorta. The generation of the enhancement data from the helical data set could lead to unanticipated error and variability. Examination of the error bars on the diagnostic scan TECs in the plots shows there was substantial variability in the TEC data (largely a result of the selection of thin-slice CT data for these analyses). Unfortunately, the ideal validation scenario in which a single level scan is performed at the ascending aorta during the diagnostic injection is not feasible with humans because of the excess radiation and contrast material to which the subjects would be exposed. For these reasons, animal and phantom models are needed to adequately study contrast prediction models and contrast protocol generation techniques. Animal testing can be expensive, so a validated and realistic cardiovascular phantom that mimics the transport and distribution of contrast material has much value. Such a phantom is, for example, described in U.S. patent application Ser. No. 12/397,713.

Because the data-driven identification estimation techniques use data derived from the system (using a test bolus), they should produce greater prediction accuracy. As expected, the prediction error in subjects 6, 8 and 12, who had the greatest prediction errors with the hybrid model as described above, decreased because the estimators rely upon image data acquired from the subjects. With a larger clinical data set, a statistically significant reduction in prediction error could be realized.

Whereas the MLE method was found to be a superior approach, for example, when two TECs were available, consideration must be made in a clinical algorithm when two ROIs can not be placed or when the data from the first ROI is corrupted. It is anticipated, therefore, that a clinical algorithm should use a tSVD or other non-parametric methodology as a secondary approach for estimating contrast enhancement in the scenario just mentioned. A classification can, for example, be used to determine whether the TEC data are adequate for use by the MLE technique.

In summary, comparison of the two data-driven contrast enhancement methods revealed the MLE was more robust to real-life considerations encountered in the clinic. Specifically, the MLE can better predict contrast enhancement when shorter segments of test-bolus enhancement data are available. The tSVD method, however, only requires the placement of one ROI and is potentially less computationally burdensome. Maximum likelihood estimation was successfully used in identifying the reduced order PBPK model developed to enable patient-specific contrast enhancement predictions. Comparison tests using the hybrid model and retrospective clinical data demonstrated that the MLE was superior to the tSVD. As discussed above, a clinical system, method or algorithm can, for example, consider both data-driven techniques (parametric and not parametric) for estimating patient-specific contrast enhancement because there will be situations in which sufficient or suitable data (for example, two TECs) cannot be generated from a test bolus injection to determine parameters in a parametric technique. In such cases, the algorithm can, for example, attempt to generate the contrast enhancement prediction using the tSVD method.

Patient Specific Contrast Protocol/Parameter Generation

Patient specific and data-driven techniques for identifying and predicting contrast pharmacokinetics in the human cardio-vascular system were set forth above. Such techniques are suitable not only to predict contrast enhancement, but to provide a method to compute an injection protocol that achieves prospectively chosen enhancement targets for an individual patient and procedure while using a minimal volume of contrast material. In a number of representative embodiments, system and methods for computing individualized injection protocols for contrast-enhanced, cardiothoracic CT Angiography are described. Such systems and methods were tested using the hybrid PBPK model described above as a surrogate for human data.

The problem can, for example, be posed as a non-linear minimization problem, with a non-negativity constraint placed on the input function. A distinct difference between the approach developed here and previously published efforts to compute individualized contrast protocols is that an effort is not made to force the predicted contrast enhancement to a specific trapezoidal function. In a number of such approaches, a contrast injection protocol was derived that attempted to achieve a constant, uniform contrast enhancement throughout the duration of the scan. An unfavorable effect of those approaches is that excess control energy (contrast volume) was exerted to achieve the uniform peak enhancement as compared to attempting to focus on achieving peak enhancement.

In the past, typical acquisition times for CTA scans ranged between 20-40 seconds. With the current generation of CT scanners, the acquisition window for CTA data rarely exceeds 10 seconds. It is less important, with very short scan acquisitions, to design injection protocols that minimize or prevent skewed, peaked enhancement profiles. Rather, a modern injection protocol generation technique can, for example, attempt to ensure that the scan occurs during the peak contrast enhancement and that a sufficient contrast enhancement is achieved at the start of data acquisition and at the end of the scan acquisition. The scan durations for the clinical data set used in the comparisons described above averaged 10 seconds and were collected in 2006 and 2007. In the past few years, CT technology has advanced such that those scan times are now longer than the typical scan duration.

Figure 35:
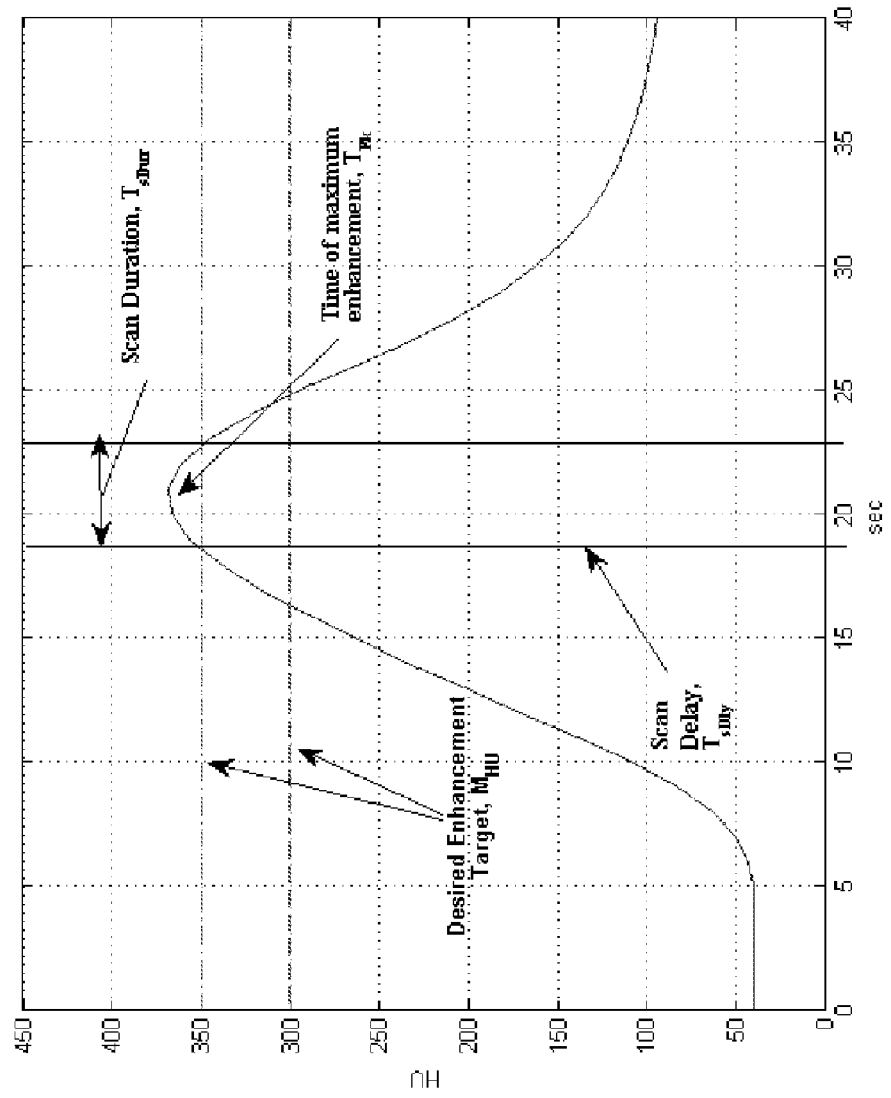
FIG. 35 illustrates a depiction of a desirable outcome from individualized protocol generation. The solid, curved line is a contrast enhancement profile computed with the hybrid PK model, the vertical lines represent the CT scan acquisition window and the dashed horizontal lines represent desired enhancement levels.

Several goals of CTA contrast enhancement, and guiding the protocol generation methodology described herein, are graphically depicted in FIG. 35. A hybrid PBPK model simulation produced the contrast enhancement profile shown in that figure. The vertical lines represent a 4 second CTA acquisition window—a scan duration typical with contemporary CT scanners. The scan is timed so that it is positioned on the enhancement profile to ensure that peak contrast opacification is obtained during scan acquisition. At the start of scan acquisition (the scan delay) and at the end of the scan, the contrast attenuation is greater than 350 HU. If the scan duration was 8 seconds in this example and the desired enhancement target was 300 HU, then the goal would also have been satisfied by the injection profile assuming that the scan delay was adjusted appropriately to ensure the scan started at 300 HU. An individual protocol generation algorithm can also compute an individual scan delay because the optimal scan acquisition time varies as a function of the injection protocol, the patient's hemodynamics and the selected contrast enhancement target.

The contrast enhancement level is a parameter that can, for example, be free for the radiologist to choose, and the appropriate enhancement target will depend upon the preferences of the radiologist dictated by the suspected pathology, and any procedural constraints. A general consensus has emerged that a minimum contrast enhancement of 250 HU is acceptable to differentiate vasculature lumen from plaques, thrombus and other pathophysiology during cardiothoracic CTA. At coronary artery CTA, it was recently demonstrated that an increased sensitivity for detecting accurate coronary stenoses when coronary contrast enhancement is greater than 320 HU. In certain instances, when a patient has renal insufficiency or disease, a lower enhancement level may be tolerated if that means the contrast volume is minimized to help prevent or mitigate renal damage.

Regardless of the precise clinical motivation, a rational and patient-specific contrast protocol generation algorithm can, for example, provide the ability to prospectively target a contrast enhancement level for an individual patient. The algorithm can then attempt to achieve a desired maximum contrast enhancement and a minimum enhancement throughout the entire scan duration.

Important considerations of a rational contrast protocol generation algorithm were discussed above. To achieve such goals, a cost function is presented that is a component of a number of embodiments of a contrast protocol or parameter generation method, system or algorithm. The cost function is minimized via numerical optimization. In a number of embodiments, the result of the minimization is an injection protocol with the minimum flow rate and injection duration sufficient to minimize the cost. The cost function used by the contrast protocol algorithm is a function of $\hat{y}_{LH}(n)$, the predicted contrast enhancement in the Left Heart compartment generated by the data-driven, estimation methods set forth above. It is:

$$J_{Prot} = |\hat{y}_{LH}(T_{sDly}) - M_{HU}| + |\hat{y}_{LH}(T_{sDly} + T_{sDur}) - M_{HU}| + |\hat{y}_{LH}(T_{Pk}) - (M_{HU} + 50)| \quad (55)$$

where $T_{sDly}$ is the scan delay of the CT study as computed by the protocol generation algorithm, $T_{sDur}$ is the scan duration of the CTA acquisition, $T_{Pk}$ is the time of maximum contrast enhancement, and $M_{HU}$ is the desired target enhancement level. All of the parameters are identified in FIG. 35. Fifty HU is added to the peak target enhancement recognizing that the contrast enhancement will be peaked and no efforts are made to flatten the enhancement profile. Fifty HU was chosen as the target because two sections of aortic vasculature differing in contrast enhancement of 50 HU are typically not clinically relevant. Because the simulations and computations are performed in discrete time, the time parameters ($T_{sDur}$, $T_{sDly}$, and $T_{Pk}$) in the cost function are discrete time values.

The predicted Left Heart enhancement is a function of the parameter vectors and the contrast injection:

$$\hat{y}_{LH}(n) = f(\hat{\theta}_{He1D}, \hat{\theta}_{He2D}, u_{inj}(n)) \quad (56)$$

and the input function for the predicted enhancement, $\hat{y}_{LH}$ is a pulse:

$$u_{inj}(n) = Q_{inj} C_{inj}[u(n) - u(n - T_{inj})] \quad (57)$$

The last term in the cost function defined in equation 55 penalizes deviations of enhancement greater than 50 HU above the target enhancement level and is added into the cost function to prevent the situation in which the target HU is achieved but the peak is much higher than necessary (and using, therefore, more contrast than necessary to achieve the target goals).

Put within context of the injection protocol generation, the minimization procedure is stated as:

$$\arg\min_{\phi \in [\phi_{min}, \phi_{max}]} J_{Prot}(\phi) \quad (58)$$

where the arguments in the vector, $\phi$, are the flow rate of the injection protocol ($\hat{Q}_{inj}$) and the duration of the injection ($\hat{T}_{inj}$), $$\phi = [\hat{Q}_{inj}, \hat{T}_{inj}] \quad (59)$$

which parameterize the input function, equation 57.

The minimization is bounded because upper and lower limits are placed on the injection flow rate and injection duration. The obvious lower constraint is non-negativity, but the upper limits are problem specific. For example, the maximum flow rate may be determined as a function of the intravenous catheter's inner diameter or the preference of the nursing staff. The maximum injection duration is a function of the maximum volume of contrast available in the syringe. Because the upper limit of flow rate and volume are dictated by clinical constraints and are user-configurable, the upper limit of the injection duration is the maximum volume divided by the minimum flow rate. The lower flow rate limit is set to 3 ml/s and the minimum injection duration is eight seconds. Injections at flow rates less than 3 ml/s are not appropriate for CTA because they likely result in enhancements less than 250 HU for the majority of patients. Injection durations less than eight seconds at the lowest flow rate of 3 ml/s also may result in contrast volumes equivalent to the test bolus.

Figure 36:
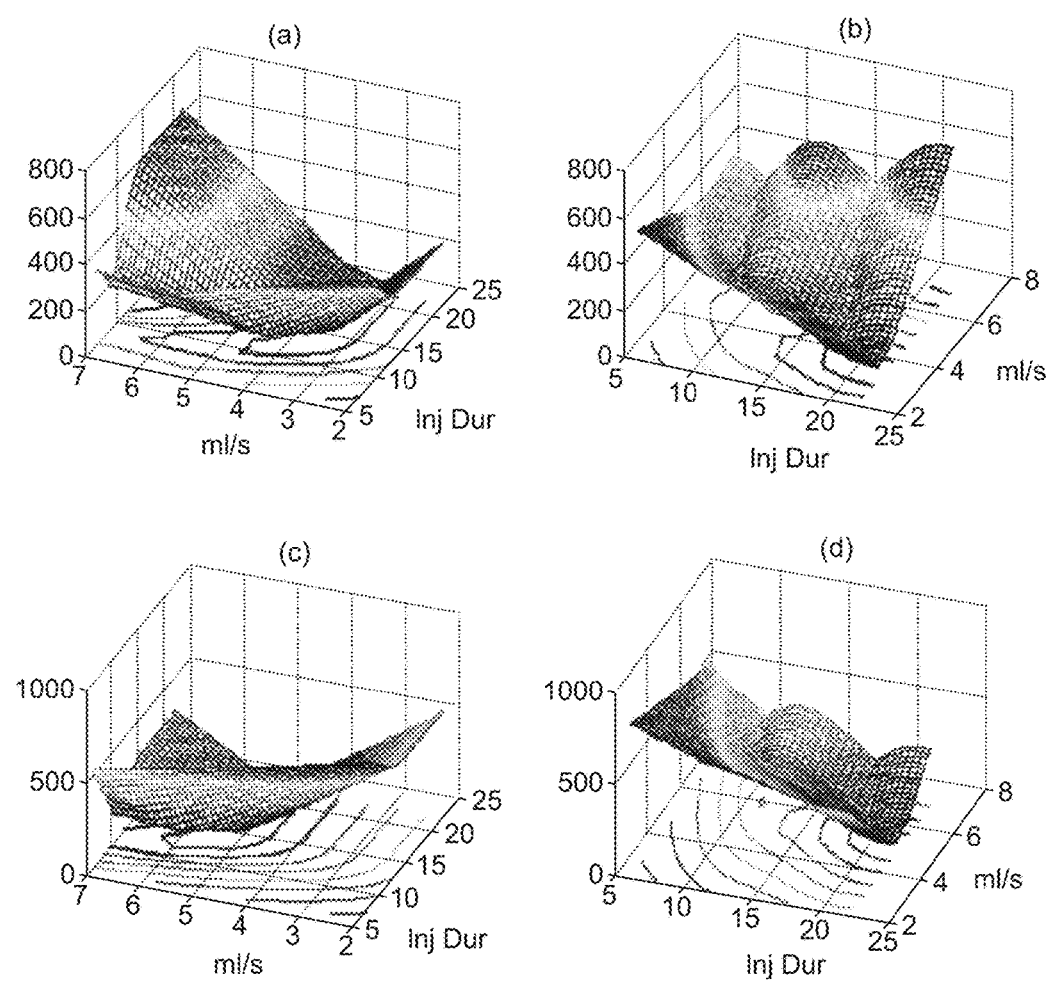
FIGS. 36A through 36D illustrate 3D surface plots of the proposed cost function using simulation data and different procedure characteristics (a) Cost function for subject 6 with a 250 HU target and a 2 second scan duration (b) Subject 6 cost function with a 250 HU target and a 8 second scan duration (c) Subject 6 cost function with a 350 HU target and a 2 second scan duration (d) Subject 6 cost function with a 350 HU target and 8 second scan duration.
Figure 37:
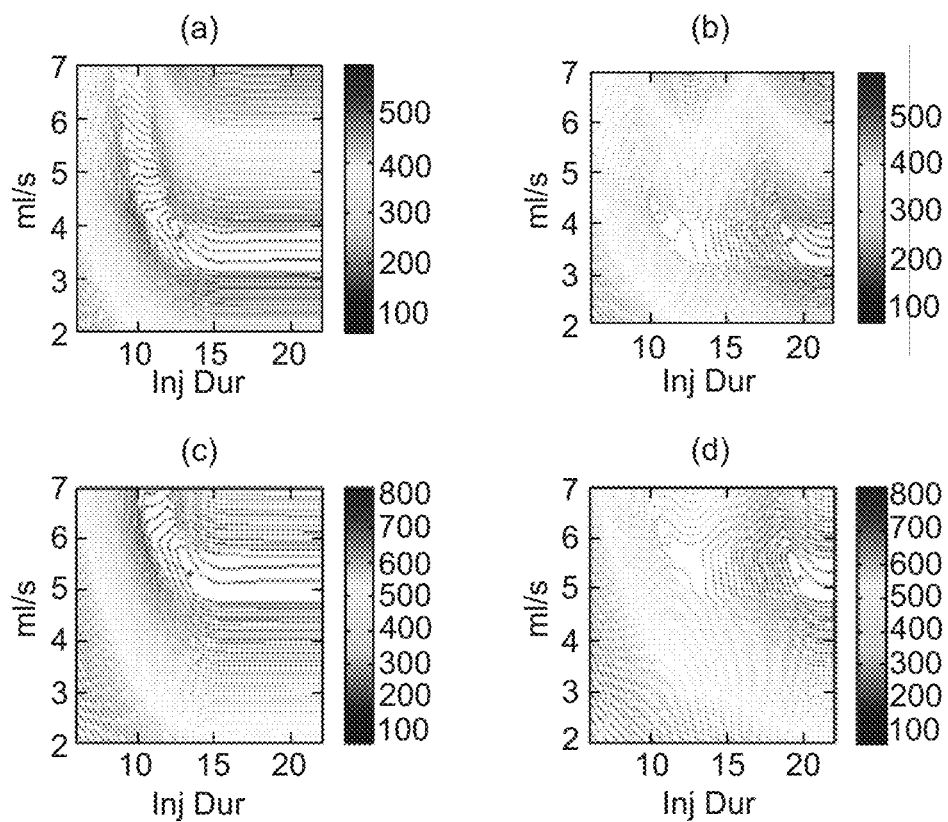
FIGS. 37A through 37D illustrates 2D contour plots of cost function for subject 6 simulated data and the proposed cost function. The cross indicates the true minimum of each projection. (a) Cost function for subject 6 with a 250 HU target and a 2 second scan duration (b) Subject 6 cost function with a 250 HU target and a 8 second scan duration (c) Subject 6 cost function with a 350 HU target and a 2 second scan duration (d) Subject 6 cost function with a 350 HU target and 8 second scan duration.

The presence of local minima and discontinuities in the cost function can, for example, be investigated prior to conducting numerical experiments and to that end, a few surface plots of the cost function given by equation 55 were generated using simulated contrast enhancement data created with the hybrid PBPK model. The parameters of the input function ranged from 2 to 7 ml/s (for Qinj) in 0.1 ml/s increments and from 6 to 22 seconds in 0.5 second increments. Subject 6's demographic data from the clinical data set were used to generate contrast enhancement predictions, $y_{LH}(n)$, at each pair of injection flow rate and duration. The contrast enhancement targets and scan durations used to generate plots of the cost function space were 250 HU, 350 HU target and 2 and 8 seconds respectively. These values represent typical upper and lower limits based on current CT scanning technology and clinical preferences. Three dimensional surface plots of the four cases are presented in FIG. 36 and 2D projections of the solution space are presented as contour plots in FIG. 37.

Inspection of the cost function surfaces show that even for one patient there is a wide variety in the morphology of the solution space as the procedural parameters vary. The 8 second scans display two minima but a well-defined global minimum. For the 2 second scan duration cases, the global minimum is distinct, but it lies in a long trough indicating potential difficulties for a numerical solver to reach the true global minimum. The long trough indicates there may be multiple pairs of injection durations and flow rates that can satisfy the target criterion (achieving the desire target contrast enhancement for an interval equal to the scan duration). These findings influenced the development of the protocol or parameter generation methodology described below.

As discussed above, a robust contrast protocol generation algorithm should adapt to each subject and scan duration, allow a radiologist to select desired contrast enhancement targets, and ensure these targets are met at the beginning and end of the scan acquisition. It should also compute a patient-specific scan delay, satisfy the requirements within the parameter constraints of lower and upper bounds, and minimize the total volume of contrast. To achieve these goals, a numerical minimization scheme was developed using the cost function defined in equations 55 and 58 with an iterative procedure that adapts initial conditions and upper parameter bounds (when possible) and then tests the solution against the target enhancement goals. Implicit to the protocol generation technique is the use of a timing bolus to generate a patient-specific estimate of contrast enhancement. The general steps of the algorithm are: (1) Inject the patient with a test bolus; (2) Process the timing bolus scan data to generate a patient-specific model of contrast enhancement (using the techniques described above) using initial conditions in $u_{inj}$ $Q_{inj}^+$, $T_{inj}^+$; and (3) Given the desired target enhancement levels (HU) and scan duration, compute an injection protocol with a flow rate and duration that satisfies equation 58.

Some parameters in the cost function of equation 55 are determined by the preference of the radiologist (target contrast enhancement, $M_{HU}$) and the procedure (scan duration, $T_{sDur}$, maximum Volume, $V_{max}$ and flow rate, $Q_{max}$) while the time of maximum contrast enhancement ($T_{Pk}$) is determined by the predicted contrast enhancement and the input function, $u_{inj}(n)$.

Consideration can be given to the parameterization of $T_{sDly}$ because it is not easily defined by the radiologist or scanner operator. It is the time on the upslope of contrast enhancement ($\hat{y}_{LH}^{Diag}(n)$) when scan acquisition should commence and is a function of the time to maximum enhancement of the test bolus enhancement, $y_{LH}^{Test}(n)$, measured in the left heart compartment (aorta).

Because the test bolus has shorter injection duration than the full diagnostic injection, the time to reach maximum test bolus contrast enhancement should not be the time to start scan acquisition during the diagnostic scan. It is common practice to compute the scan delay for the diagnostic scan as the time of maximum enhancement from the test bolus TEC plus an offset term, $T_{Offset}$. In previous studies, $T_{Offset}$ was 4 or 6 seconds based on the duration of the scan. For short scans, a longer offset time is used in an attempt to position the short scan window on the peak of contrast enhancement. When the scan is long, the scan should start earlier to help ensure the peak and the target threshold values fit inside the scan window. This scan timing approach is expressed as:

$$T_{sDly} = T_{Pk}^{Test} + T_{Offset} \tag{60}$$

where $T_{Pk}^{Test}$ is the peak time of the test bolus TEC. $T_{Offset}$ is four seconds when the scan duration is longer than or equal to four seconds, and is six seconds for scan durations shorter than four seconds. An algorithmic description is presented in Table 16.

TABLE 16

Protocol Generation Algorithm

Begin A: ESTIMATE PATIENT MODEL
  1. Use techniques in Chapter 5 based on test bolus data, $y_{LH}^{Test}$ (n) and $y_{RH}^{Test}$ (n) if using MLE technique
  2. Compute and store, $T_{Pk}^{Test}$ from $y_{LH}^{Test}$ (n)
End A
Begin B: COMPUTE CONTRAST PROTOCOL
  1. Get and store: $M_{HU}$, $T_{sDur}$, $V_{Max}$, $Q_{Max}$
  2. Set upper and lower limits on the parameter vector
    1. $\varphi_{min}$ [3 8]
    2. $\phi_{max} = \left[ Q_{max} \quad \dfrac{V_{max}}{Q_{max}} \right]$
  3. Initialize $T_{Offset}$ and $\varphi$
    1. If $T_{sDur} \geq 4$ sec
    2. $T_{Offset} = 4$ sec
    3.   $\varphi_0 = [4.5\ 15]$
    4. else
    5. $T_{Offset} = 6$ sec
    6.   $\varphi_0 = [5\ 13]$
    7. end If
    8. m = 0
    9.
  4. while targetMet != true
    1. run minimization - equation 58 - until convergence
      i. update $\varphi = [\hat{Q}_{inj}\ \hat{T}_{inj}]$
    2. compute estimated enhancement using estimated patient model $\{\theta_{He1D}, \theta_{He2D}\}$ or $h_{est}$ and $u_{inj}(t)$ with $\varphi = [\hat{Q}_{inj}\ \hat{T}_{inj}]$ TABLE 16-continued Protocol Generation Algorithm 3. Find $t_i$ s.t. $\hat{y}_{LH}^{Diag}(t_i) \geq M_{HU}$
    4. Compute $T_D$, time $\geq M_{HU}$ from $t_i$
    5. If $T_D \geq T_{sDur}$
      i. update: $T_{sDly} = t_1$, the first element of $t_i$
      ii. targetMet = true
    6. else
      i. increment m
      ii. If m ≤ 5
        1. update: $\hat{T}_{inj} = \hat{T}_{inj} + 1$
      iii. ElseIf m > 5 & m ≤ 7
        1. If $T_{Offset} == 6$
          a. $T_{Offset} = 4$
        2. elseIf $T_{Offset} == 4$
          a. $T_{Offset} = 2$
        3. end If
      iv. else
        1. Can't satisfy constraints
        2. targetMet = true
      v. end If
    7. end If
    8. end While
END B $V_{Max}$ is the maximum upper bound constraint for the minimization and is selected by the radiologist. $Q_{max}$ is the maximum flow rate for the individual patient dictated by venous access or IV catheter gauge. Both $Q_{max}$ and $V_{max}$ determine the upper constraint on the minimization routine.

A comparison with prior published results was made by implementing the Fleischmann and Hittmair algorithm and using test bolus enhancement data published in Fleischmann, D. and K. Hittmair, *Mathematical analysis of arterial enhancement and optimization of bolus geometry for CT angiography using the discrete fourier transform*. J Comput Assist Tomogr, 1999. 23(3): p. 474-84, as the input and output data. The same test bolus enhancement data was also used by the protocol generation algorithm in Table 16, and the contrast protocols generated with both methods were compared.

Validation of the protocol generation algorithm presented here was performed using the same 20 simulated data sets created with the hybrid model in as described above. Multiple combinations of scan durations and target enhancements defined the procedure data. The generated injection protocols from the numerical minimization and protocol algorithm were used as inputs for hybrid PK model simulations for each subject. The outcome was deemed successful if the contrast enhancement profile generated by the algorithm exceeded the target enhancement ($M_{HU}$) for the duration of the scan, $T_{sDur}$.

The algorithm was implemented and executed in MATLAB (R2008b) using the Optimization toolbox function fmincon as the numerical optimization method. The fmincon function performs nonlinear, constrained optimization as a Sequential Quadratic Programming (SQP) problem. SQP techniques break the larger problem into smaller, Quadratic Programming (QP) subproblems at each iteration of the solver. The method uses a line-search technique (an approximation of the Hessian is made at each iteration and a quasi-Newton method updates the Lagrangian) and a merit function to solve each subproblem. More details of the solver may be found in Coleman and Branch, *Optimization Toolbox for Use with MATLAB, User's Guide*, T. Mathworks, Editor 2007.

The solver specific constraints were: convergence tolerance on the parameters (TolX)=1E-4, convergence tolerance on the function (TolFun)=1E-4, minimum increment for the finite difference subroutine (DiffMinChange)=0.01, maximum increment for the finite difference subroutine (DiffMaxChange)=2.0, and the maximum number of function evaluations at each iteration was 400. The maximum number of iterations (maxIter) was set at 100.

An implementation of the Fleischmann and Hittmair methodology, as summarized in Appendix 2 hereof at the end of this description, was made in MATLAB using the published test bolus enhancement data (as numerically tabulated in an Appendix of Fleischmann, D. and K. Hittmair, *Mathematical analysis of arterial enhancement and optimization of bolus geometry for CT angiography using the discrete fourier transform*. J Comput Assist Tomogr, 1999. 23(3): p. 474-84), and desired enhancement levels. The test bolus-enhancement response from a human subject (enhancement values reported in Fleischmann, D. and K. Hittmair, *Mathematical analysis of arterial enhancement and optimization of bolus geometry for CT angiography using the discrete fourier transform*. J Comput Assist Tomogr, 1999. 23(3): p. 474-84.) is presented in FIG. 38 and was used to generate contrast protocols. The test bolus enhancement response is typical of short bolus injections measured at the descending aorta by a CT scanner. The desired enhancement was defined as a level of 200 HU starting at the peak of the test bolus enhancement. An increasing ramp ranging from 0 to 200 HU and a decreasing ramp from 200 HU to 0 were added to the leading and trailing edges of the desired enhancement profile to generate a trapezoidal enhancement profile. The slope of the leading and trailing ramps matched those reported by Fleischmann and Hittmair.

Figure 39:
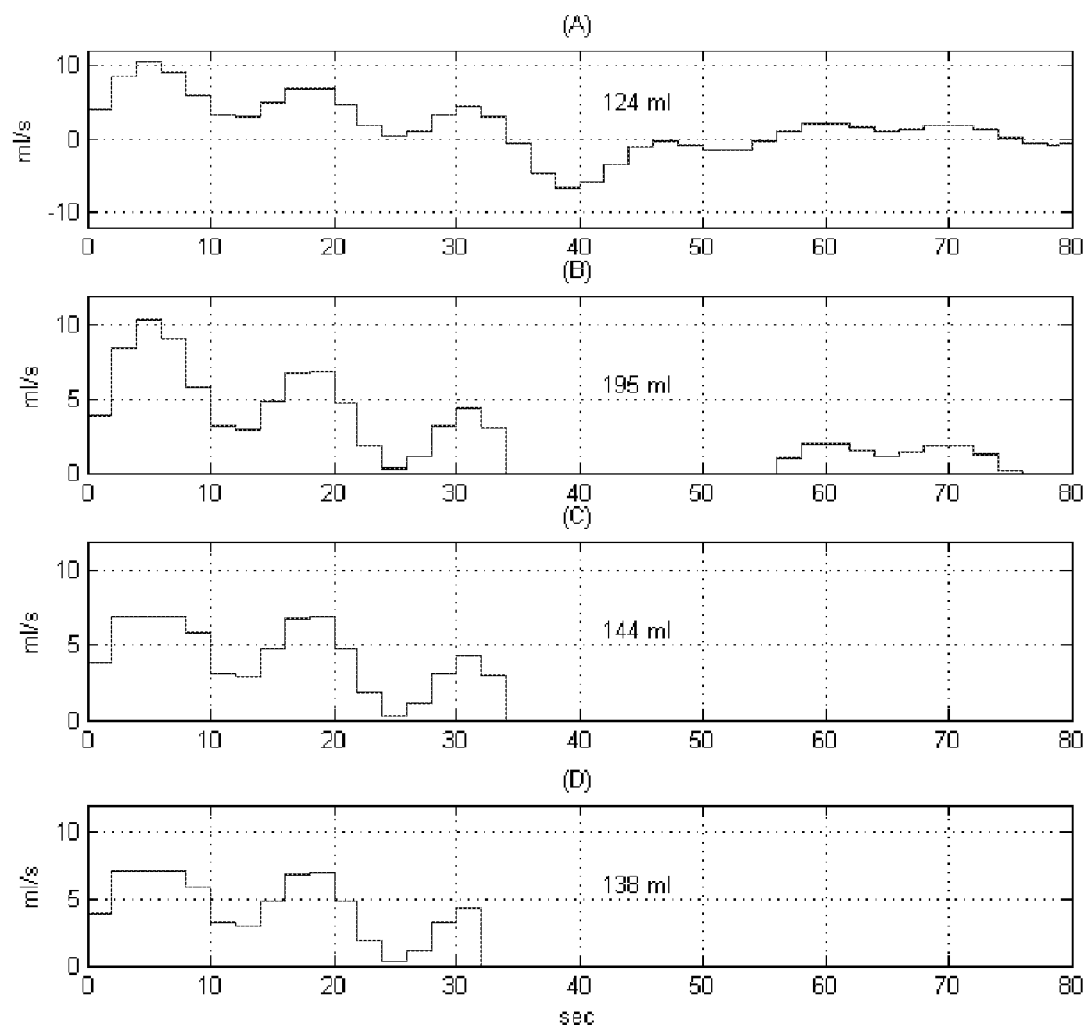
FIGS. 39A through 39D illustrate computed injection protocols using the Fourier deconvolution method described in [9], Ts=2 sec/image. The total contrast volume of the injection is listed in each subfigure. (A) Raw protocol. Because the injection flow rate is allowed to be negative, the total contrast volume is lower than B–D. (B) Non-negative protocol (C) Non-negative protocol clamped at 7 ml/s and injection commands at time >34 sec removed (D) Same protocol as C but samples post 32 seconds removed.
Figure 40:
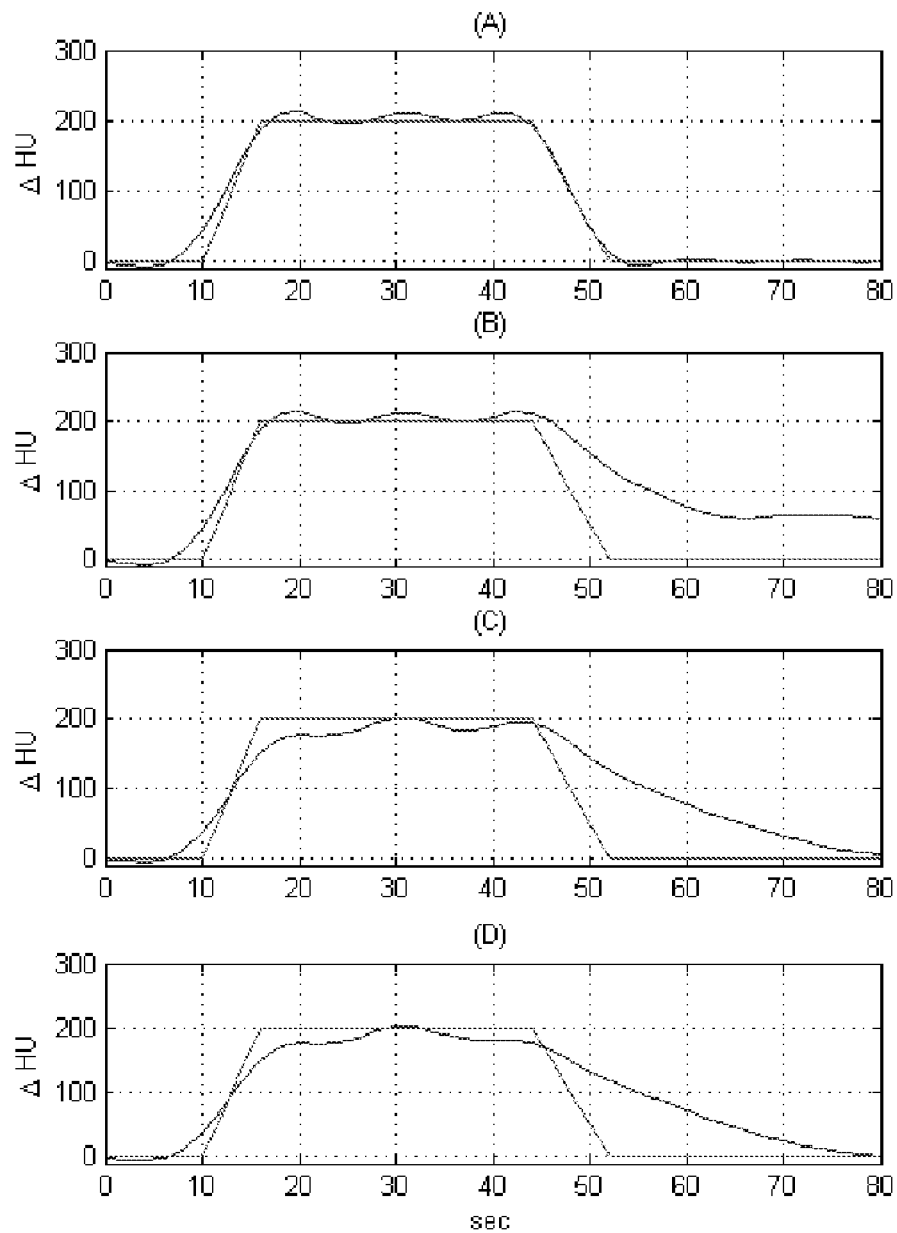
FIGS. 40A through 40D illustrate predicted (blue) and desired (green) enhancement levels generated with the injection protocols presented in (A) Ideal enhancement profile using the raw protocol (B) Enhancement generated with non-negative injection protocol (C) Enhancement when non-negative injection is clamped to 7 ml/s and injection is not allowed post 34 seconds (D) Enhancement profile as in C but with samples ignored after 32 seconds.

FIGS. 39A-D presents computed injection protocols using the Fleischmann and Hittmair technique. FIG. 39A shows the raw protocol computed by the algorithm. The injection protocol is negative in sections and exceeds flow rates commonly employed, especially when viscous (13-20 cPoise), high Iodine concentration contrast agents are administered. FIG. 39B is the same computed protocol, but with negative flow rates truncated to zero. FIGS. 39C and D present the computed protocol with the maximum flow rate set at 7 ml/s (arbitrarily). The protocols of FIGS. 39C and D truncate the input protocol at different sample points as explained below.

Figure 38:
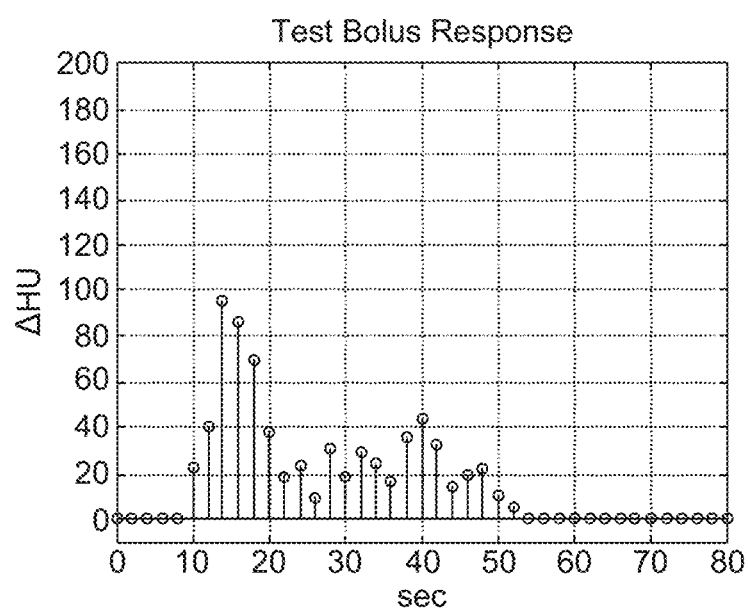
FIG. 38 illustrates sample test bolus response measured in a subject in the descending aorta.

The time to peak enhancement in the test bolus enhancement of FIG. 38 is 14 seconds and the transport delay, or contrast propagation time, for the contrast to arrive in the vessel (ascending aorta) is approximately 8-10 seconds. The contrast propagation time limits the contribution of contrast in the injection protocol for samples less than 10 seconds prior to the end of the scan. The protocol in FIG. 39C is truncated at 34 seconds whereas the protocol of FIG. 39D is truncated at 32 seconds.

A trapezoidal, numerical integration was used to compute the total volume of contrast in each injection and the volumes are annotated in FIGS. 39A-D. These contrast volumes were computed to serve as a basis of comparison to the techniques presented in this dissertation. The total contrast volume decreased as the protocols were modified, but there is clearly arbitrariness in the approach taken to generate these results. Fleischmann and Hittmair do not propose an optimization algorithm to minimize the contrast volume.

Predicted enhancement profiles using the estimated impulse response from Fourier deconvolution (using Fleischmann and Hittmair's technique) and the computed protocols of FIGS. 39A-D are shown in FIGS. 40A-D The smallest residual between predicted and desired enhancement is for protocol A and the most for protocol D.

Figure 41:
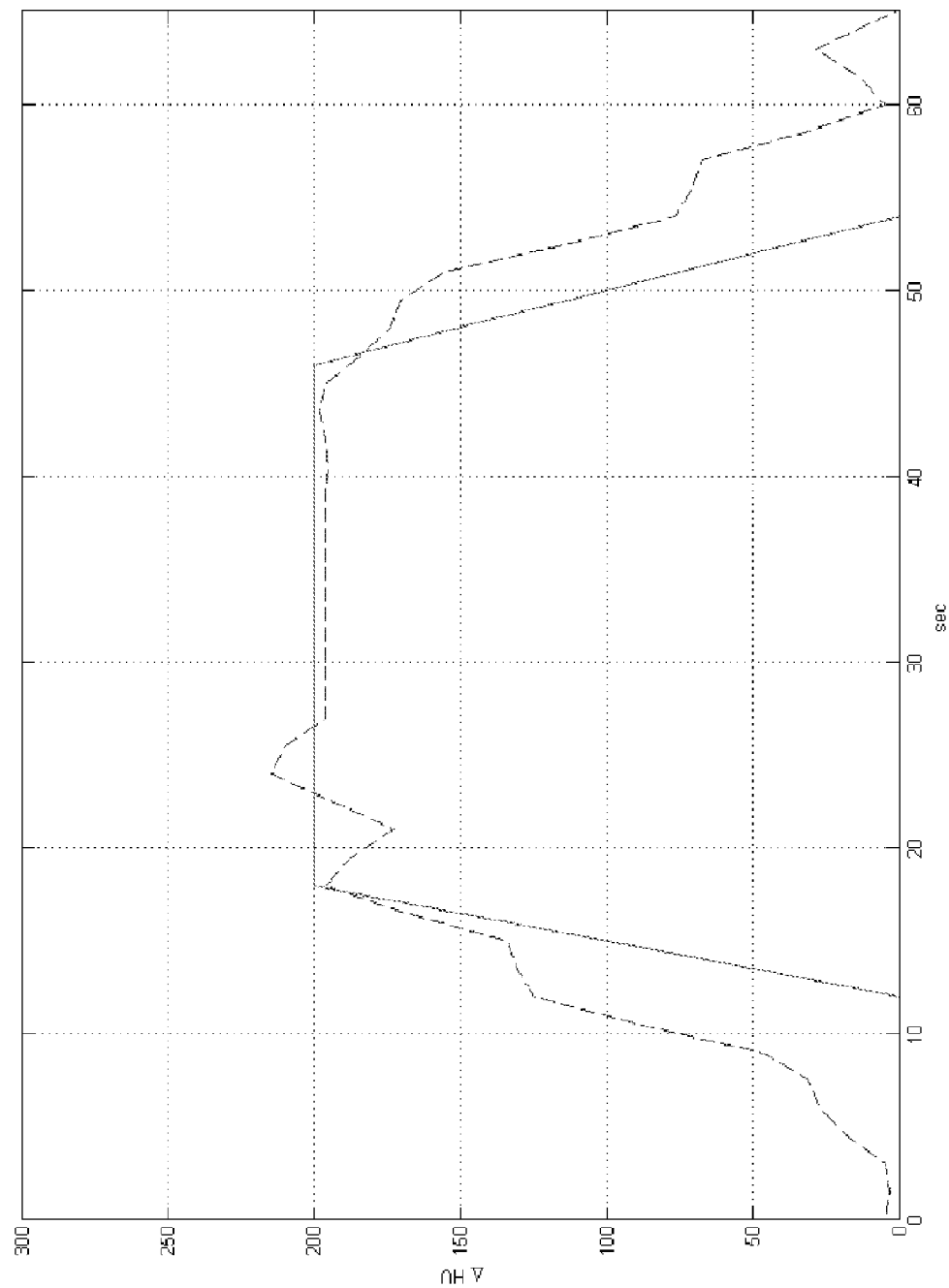
FIG. 41 illustrates comparative result between desired enhancement profile (solid line) and the predicted enhancement using the protocol generation algorithm in Table 18 (dashed line). A contrast volume of 115 ml and a flow rate of 4.1 ml/s was computed by the algorithm to generate the enhancement profile shown in the figure. The desired scan duration was 30 seconds.

A contrast protocol was also created, using the same test bolus and procedure data, with the algorithm described in Table 16. Because only one test bolus curve is presented in Fleischmann, D. and K. Hittmair, *Mathematical analysis of arterial enhancement and optimization of bolus geometry for CT angiography using the discrete fourier transform*. J Comput Assist Tomogr, 1999. 23(3): p. 474-84., the tSVD methodology was used to identify the patient model. The resulting contrast enhancement curve, superimposed on the desired 30 second scan duration, is shown in FIG. 41. The contrast volume computed by the algorithm, to achieve the desired enhancement target was 114.9 ml, at a flow rate of 4.1 ml/s. The volume is 20 ml less than that of the lowest volume prediction from the Fleischmann and Hittmair algorithm (FIG. 39D) and doesn't require modulation of the flow rate over time which could lead to undesired contrast bolus broadening in the peripheral vasculature.

The protocol generation algorithm was tested under realistic conditions using 20 simulated data sets generated with the hybrid PBPK model. Subject demographic (height, weight, sex, age) data were identical to those from the retrospective clinical data set used in studies described above. The physiologic parameter relationships defined in Tables 1 and 2 were used to set the parameters of the hybrid model for the simulation runs. For each subject, the model was executed (simulation sample period=0.01 sec/sample) with a 20 ml test bolus (with a 40 ml saline flush phase) at 5 ml/s as an input function and the corresponding test bolus TECs ($y_{RH}^{Test}(n)$), $y_{LH}^{Test}(n)$) were down-sampled. To better resemble clinical test bolus TECs, the vectors were windowed at 5 seconds (relative to the origin) and truncated at 25 seconds. Also, zero-mean AWGN with standard deviation of 1 HU was added to both TECs.

After the test-bolus enhancement curves were generated, they were used as the input and output data for the MLE algorithm developed in as described above. The parameterized patient-specific model parameters ($\hat{\theta}_{He1D}$, $\hat{\theta}_{He2D}$) were used by the protocol generation algorithm defined in Table 16. It is desirable, for example, that a protocol generation system, method or algorithm accommodate different procedure specific parameters and constraints. Therefore, the simulated data were used to generate injection protocols under a combination of procedure settings. All 20 subjects were simulated and tested with desired target enhancements ($M_{HU}$ of 250 HU, 300 HU and 350 HU which span the range of minimally accepted vessel contrast enhancements considered acceptable for cardiothoracic CTA. At each enhancement target value, experiments were conducted at scan durations of 2, 4 and 8 seconds. These ranges of scan durations are typically encountered when performing cardiothoracic CTA scanning procedures with modern MDCT scanners (64, 128, 256, 320 slice and dual-source). The maximum flow rate, $Q_{max}$, was 7 ml/s and the maximum volume, $V_{max}$, was 150 ml for all subjects. The minimum flow rate in all experiments was 3 ml/s and the minimum injection duration was set to 8 seconds. These values were chosen because it is generally accepted that CTA below 3 ml/s is not feasible and contrast bolus durations less than 8 seconds result in smaller than desired bolus volumes at the minimum flow rate of 3 ml/s (21 ml, for example).

Figure 42:
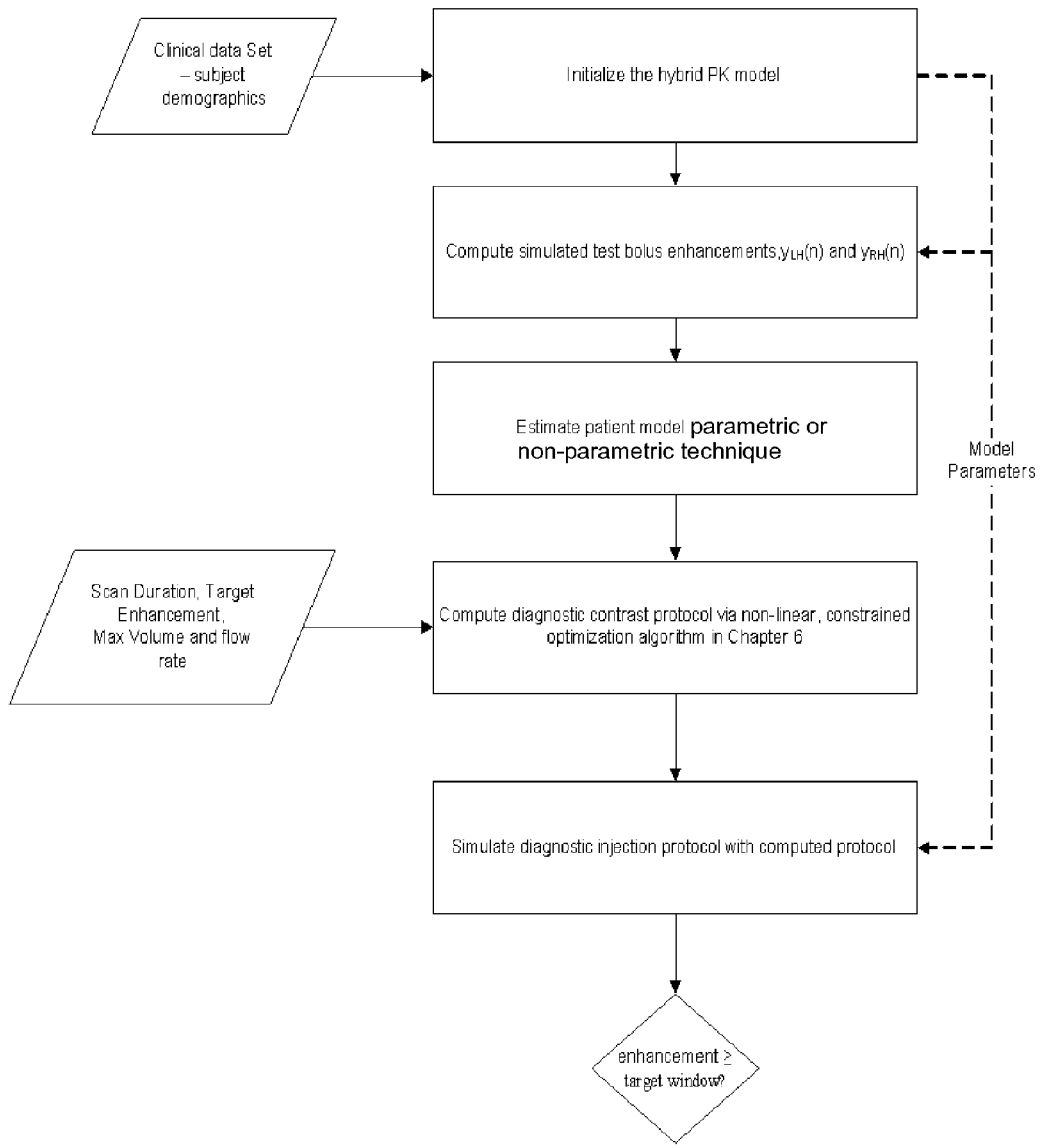
FIG. 42 illustrates an embodiment of protocol generation validation experiments.

The performance of the protocol generation algorithm was assessed by using the computed injection protocol as an input signal to the hybrid PK model. Upon simulation of the model with the calculated injection protocol, the duration of enhancement greater than the desired $M_{HU}$ was recorded. The enhancement durations were compared to the scan duration for each experimental set and success was defined as enhancement greater than the target for the specified scan duration. Because of rounding errors (mostly introduced by the downsampling of the TECs to 1 sec/sample) and other random effects, acceptability was extended to scan duration plus/minus 0.5 seconds. A flowchart of the experimental configuration is presented in FIG. 42.

Figure 43:
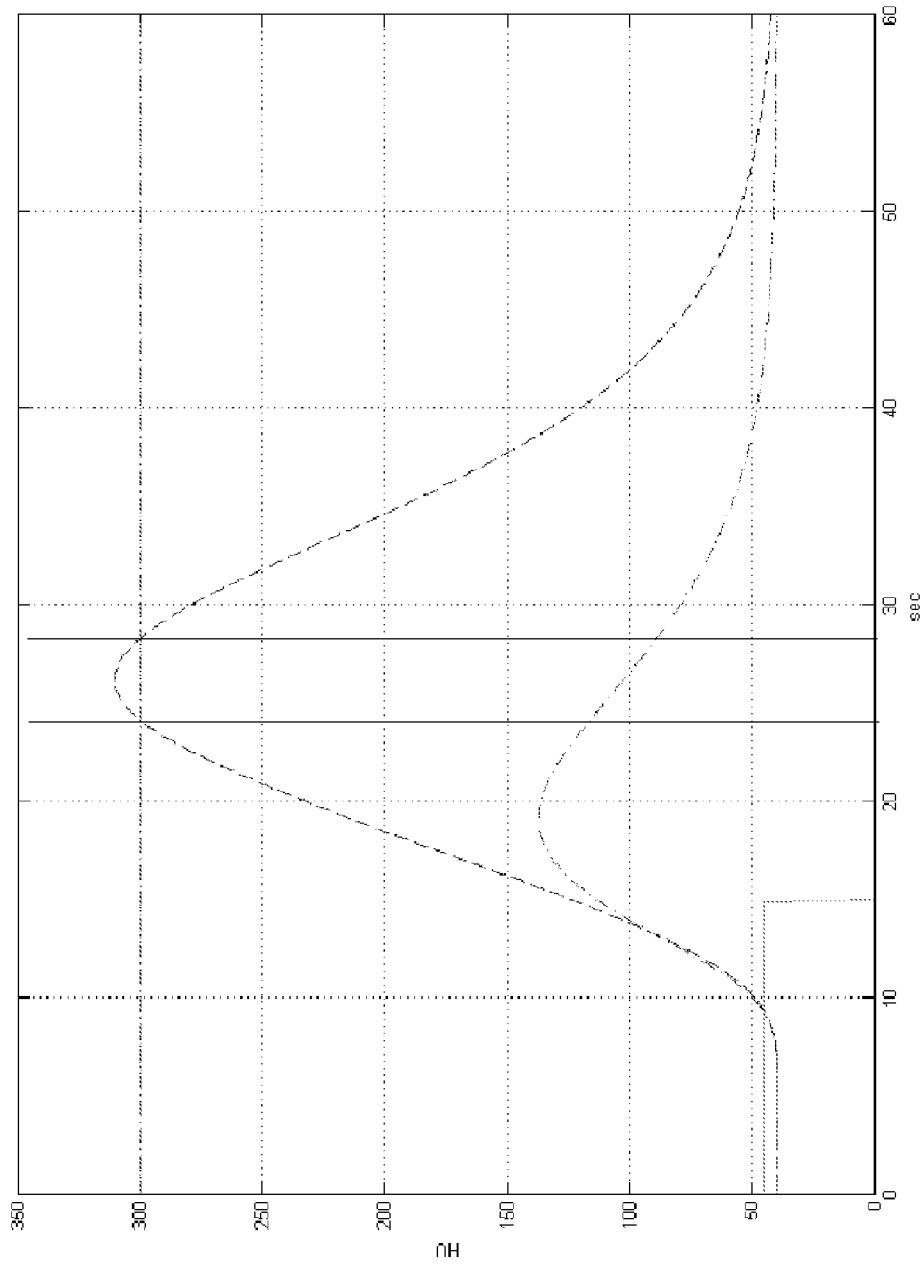
FIG. 43 illustrates hybrid model simulation result using Subject 8 data and injection protocol computed with methods presented in this chapter. Subject 8 from the clinical data set was used to parameterize the hybrid model. The dot-dashed TEC (peaking at ~130 HU) is the Left Heart test bolus enhancement curve. The dashed TEC was generated with the injection protocol (flow rate 4.52 ml/s. 67.8 ml, 15 sec), visualized by the solid rectangle at the bottom left of the figure (flow rate multiplied by 10). The dot-dashed horizontal line intersecting the top of the diagnostic TEC is the target enhancement $M_{HU}$ of 300 HU. The two solid, vertical lines represent the scan duration window, starting at $T_{sDly}$ computed by the algorithm and lasting for 4 seconds.

An example of a typical result from the experimental data set is shown in FIG. 43. In this instance (subject 8 from the clinical data set), the scan duration was 4 seconds and $M_{HU}$ was 300 HU. The algorithm computed a diagnostic injection protocol of 4.52 ml/s for 15 seconds (67.8 ml of contrast) and resulted in a hybrid model TEC exceeding the target enhancement for the scan duration.

Figure 44:
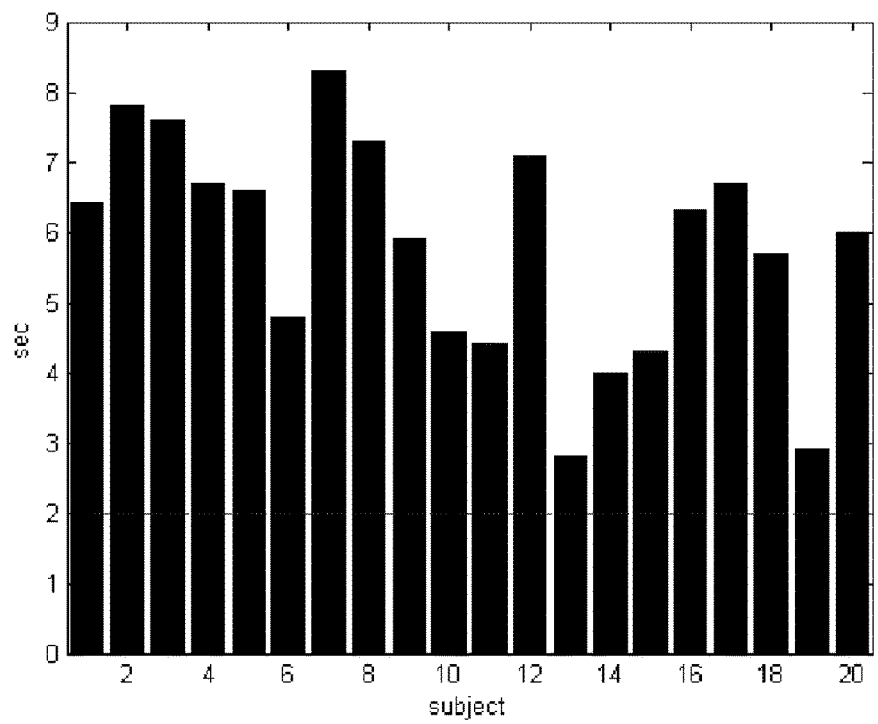
FIG. 44 illustrates enhancement values greater than the 350 HU target for the scan duration plotted for all 20 simulated subjects. The horizontal, dashed line at 2 seconds is the scan duration for all runs.
Figure 45:
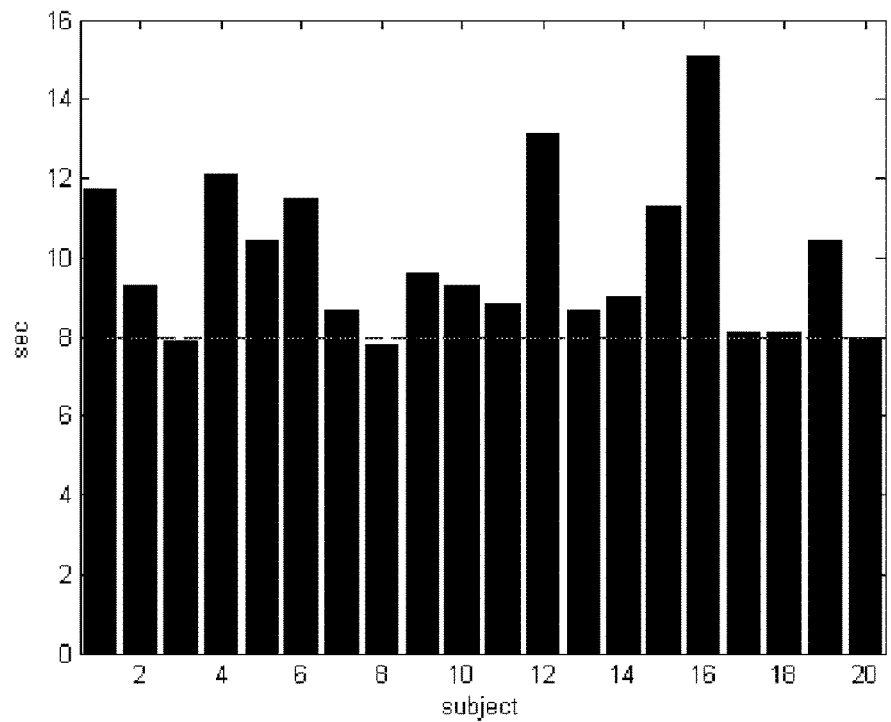
FIG. 45 illustrates enhancement values greater than the 250 HU target for the scan duration plotted for all 20 simulated subjects. The horizontal, dashed line at 8 seconds is the scan duration for all runs.

Two summary plots displaying time exceeding the target enhancement, $M_{HU}$, across the 20 simulated subjects are presented in FIG. 44 and FIG. 45. In both figures, the horizontal dashed line represents the scan duration for the particular experiment. In FIG. 44, the scan duration was 2 seconds and the target enhancement was 350 HU. For all 20 subjects, the enhancement exceeded $M_{HU}$ for the scan duration (starting at the computed scan delay, $T_{sDly}$).

FIG. 45 shows the results of all twenty subjects tested when the scan duration was 8 seconds and $M_{HU}$ was 250 HU. In this experiment, two subjects had resulting enhancement times slightly less than the target (subject 3-7.8 seconds, subject 8-7.6 seconds), but were within the tolerance stipulated. The other subjects had resulting enhancement curves greater than or equal to the scan duration and, in some instances, with excess enhancement sample time. Compared to the two second scan duration and 350 HU target results, however, it appears that the optimization resulted in more efficient (minimum flow rate and injection duration) protocols. Tabulated results for all the experiments, including summary statistics of the computed diagnostic injection protocols (flow rates, volumes) are shown in Table 17.

tioned near the peak of contrast enhancement. One can achieve greater peak enhancement by injecting with a short duration at a high flow rate.

In the results shown in FIG. 44, the target enhancement was exceeded by a few seconds in all cases. These results could indicate that for short scan durations, the cost function can, for example, be modified to result in shorter injection duration. Also, for short scan durations, the positioning of the scan duration on the enhancement curve could be reconsidered. For example, the $T_{sDly}$ could be set as the $T_{pk}$ minus one half of the scan duration. This approach will not produce ideal results, however, when scan times are 8 seconds or longer because the TEC morphology tends to become skewed (to the right) for longer injection durations.

The foregoing description and accompanying drawings set forth a number of representative embodiments. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

APPENDIX 1

Ostergaard et al. applied Fourier deconvolution and other deconvolution approaches to extracting the "residue" function, or impulse response of brain tissue between a feeding artery and a draining vein for assessment of ischemic stroke in Contrast Enhanced (CE) MRI perfusion. Ostergaard, L., et al., *High resolution measurement of cerebral blood flow using intravascular tracer bolus passages. Part I: Math-*

TABLE 17

Summary results from protocol generation experiments. Each row represents 20 simulations of the hybrid PK model at the procedure targets defined in the first two columns.

| Targets | | Injection Protocol Statistics (350 mgI/ml) | | | Summary Output Criteria | |
|---|---|---|---|---|---|---|
| | | | | | Mean t > scan Dur n > scan Dur & | |
| MHU [HU] | Scan Duration [sec] | Mean Vol [ml] | Mean Flow [ml/s] | Mean Dur [sec] | [sec] | MHU |
| 350 | 2 sec | 69.1 | 5.16 | 13.4 | 5.8 | 20 |
| 350 | 4 sec | 69.3 | 5.26 | 13.2 | 6.2 | 20 |
| 350 | 8 sec | 76.0 | 4.75 | 16.0 | 8.1 | 20 |
| 300 | 2 sec | 54.3 | 5.28 | 10.3 | 5.5 | 20 |
| 300 | 4 sec | 55.1 | 4.78 | 11.5 | 5.8 | 20 |
| 300 | 8 sec | 62.8 | 4.15 | 15.1 | 8.3 | 20 |
| 250 | 2 sec | 43.6 | 4.91 | 8.9 | 9.9 | 20 |
| 250 | 4 sec | 43.8 | 4.37 | 10.0 | 6.3 | 20 |
| 250 | 8 sec | 53.7 | 3.59 | 15.0 | 8.6 | 20 |

In all of the experimental cases, the non-linear optimizer found a feasible solution and converged to a solution. The average execution time for each subject's estimation and protocol optimization was 5.6+/−1.2 seconds (Pentium III PC, windows XPPro, 2 GB RAM).

Testing of the protocol generation algorithm using the hybrid PK model validated the technique as robust across different patient types and procedure settings. The results in Table 17 reveal trends consistent with contrast enhancement principles. For example, the injection duration and contrast volume increase as scan durations increase for each target enhancement group. Also, as the scan durations decrease, the computed flow rates increase, which is expected because with short acquisitions, the scan duration should be posi-

*ematical approach and statistical analysis.* Magn Reson Med, 1996. 36(5): p. 715-25. Whereas the MRI perfusion application is different from the current problem, it has similarities to the contrast medium/patient identification problem in that measurements are made of a physiologic blood flow system using intravascular agents. Therefore similar noise processes would be expected. Ostergaard discovered that truncated Singular Value Decomposition (tSVD) was the most robust method for solving the tissue impulse response inverse problem, even when the SNR was <10. Ostergaard, L., et al., *High resolution measurement of cerebral blood flow using intravascular tracer bolus passages. Part II: Experimental comparison and preliminary results.* Magn Reson Med, 1996. 36(5): p. 726-36. Recently, Koh et al. also demonstrated the robustness of tSVD in MR perfusion assessment using a novel technique to choose the Singular Value Decomposition's truncation index. Koh T S, W. X., Cheong L H, Lim C C T, *Assesment of Perfusion by Dynamic Contrast-Enhanced Imaging Using a Deconvolution Approach Based on Regression and Singular Value Decomposition*. IEEE Trans Med Imaging, 2004. 23(12): p. 1532-1542.

The goal of the tSVD (as is other deconvolution techniques) is to estimate h, given a noisy y measurement vector and a U matrix constructed from input samples, u.

$$y = h*u + \varepsilon = H \cdot U + \varepsilon \quad (A1)$$

and ε is assumed to be an iid random process. Before solving for h, H is decomposed into singular vectors (left U and right V) and a singular value matrix (Σ) via singular value decomposition:

$$H = U\Sigma V^T = \sum_{i=1}^{n} u_i \sigma_i v_i^T \quad (A2)$$

where Σ is a square matrix with the nonnegative singular values of H on the diagonal. A solution for h can be found by algebraic manipulation if H from equation A2 is inserted into equation A1. An obvious solution for h is:

$$h = (U\Sigma V^T)^{-1}{}_y \quad (A3)$$

Small singular values, however, can amplify the noise present in the measurement vector. To limit the effect of noise, the rank of the equations can be reduced by ignoring singular values Σ greater than a threshold value. The solution vector for h is:

$$h_k = \sum_{i=1}^{k} \frac{u_i y_i}{\sigma_i} v_i \quad (A4)$$

The rationale for proper selection of the truncation index, k, for a given problem must be considered, however. tSVD is a regularization technique—a nonparametric approach to solving ill-conditioned inverse problems in which one makes a tradeoff between data fitting and smoothness of the solution. A standard regularization technique is Tikhonov's regularization that solves the following minimization problem (assuming the standard notation of a linear system Ax=b):

$$\min\{\|Ax-b\|_2^2 + \lambda^2 \|x\|_2^2\} \quad (A5)$$

where λ, is the regularization parameter that weights the solution norm $\|x\|_2^2$ versus the residual norm $\|Ax-b\|_2^2$. Hansen demonstrated the connection between Tikhonov regularization and tSVD and how the solution of equation A5 can be expressed in terms of the SVD:

$$x_\lambda = \sum_{i=1}^{n} \left(\frac{\sigma_i^2}{\sigma_i^2 + \lambda^2}\right) \frac{u_i y}{\sigma_i} v_i \quad (A6)$$

where $\sigma_i$ are singular values, and λ, is the regularization parameter. The first term in the summation is known as the Tikhonov filter factor. Hansen, P. C., *The truncated SVD as a method for regularization*. BIT, 1987. 27: p. 534-55. If the truncation index, k, from the tSVD is known, then the regularization parameter is $\lambda = \sigma_k$ where $\sigma_k$ is the singular value at index k.

Figure 47:
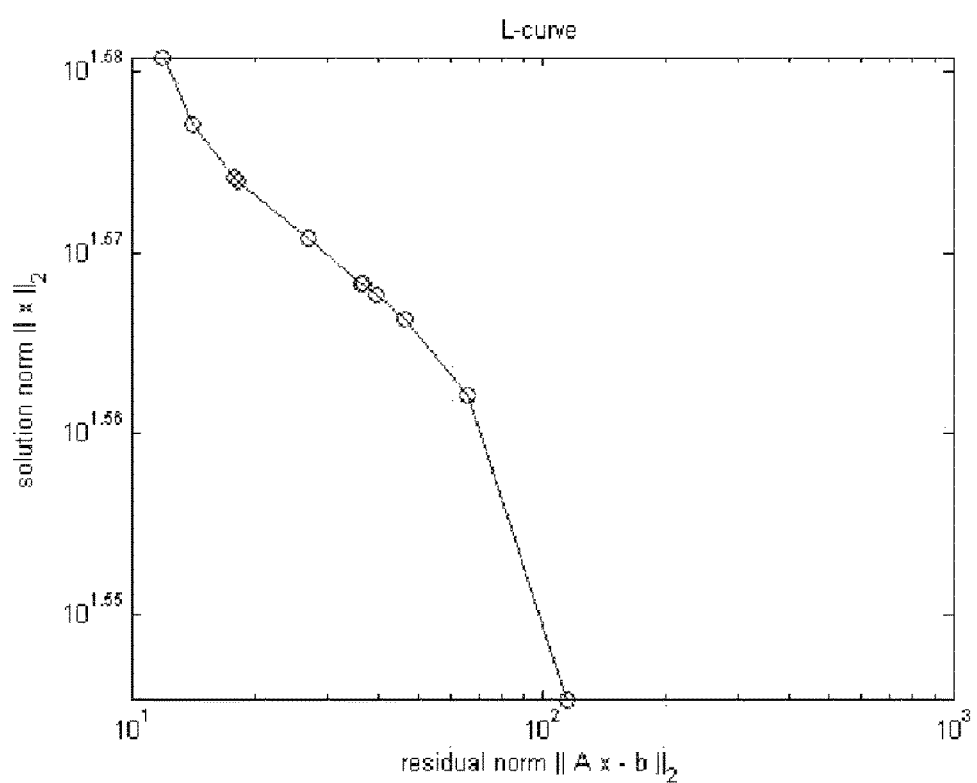
FIG. 47 illustrates an Example "L-curve" constructed with a clinical data set.

The L-curve is a log-log plot (FIG. 47 is an example) of the solution norm versus the residual norm for various values of the regularization parameter. The (index) point of maximum curvature on the L-curve is used as the estimate of optimal trade-off between solution and residual errors. A drawback to this technique, however, is that sometimes a corner point is obscured by noise.

Koh et al. present an automated technique for finding the truncation index for the tSVD (and thus the regularization parameter $\lambda = \sigma_k$) by fitting piecewise linear curves to a log plot of the SVD's Fourier coefficients ($|u_i^T y|$) versus the index of singular values. The log plot representation of the Fourier coefficients is called a Picard plot.

Figure 46:
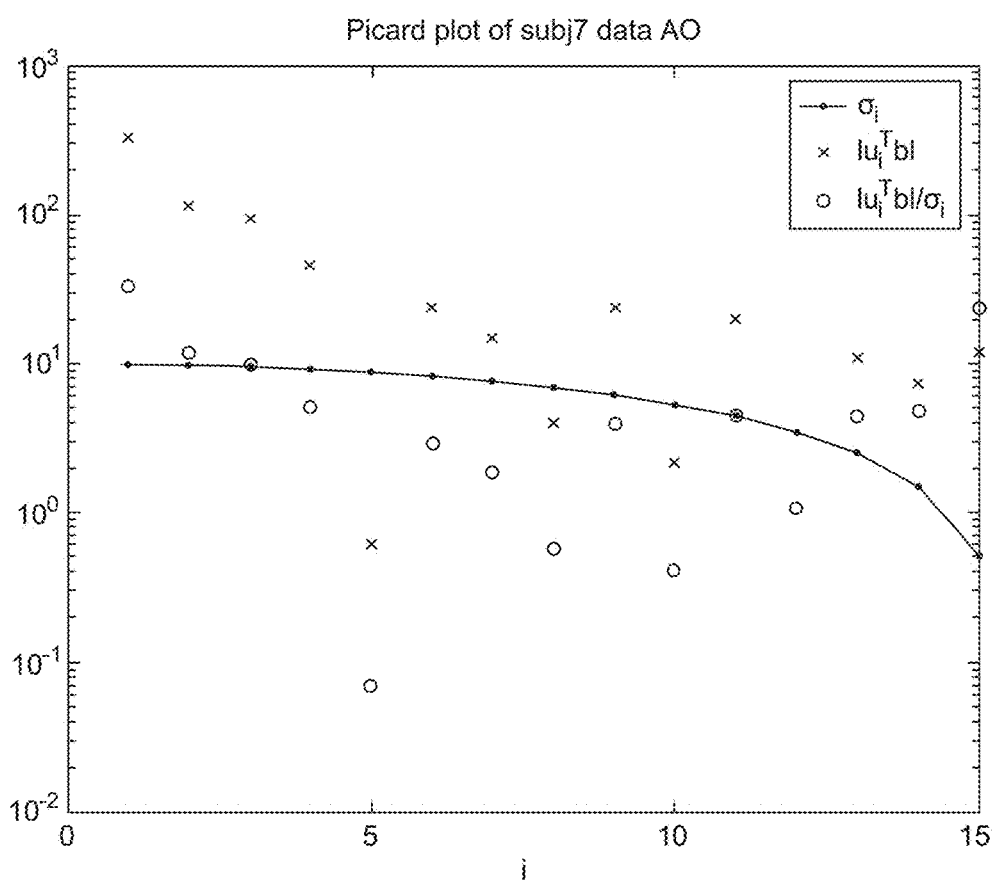
FIG. 46 illustrates an example Picard plot using clinical data. The x axis is index value and the y-axis is a log transform of the Fourier coefficients $|u_i b|$. The singular values are plotted with diamonds and connected with a solid line.

In the presence of noise, the log of the Fourier coefficients in a Picard plot tend to monotonically decrease to a point at which the slope of the line decreases and begins to level-off (see the example in FIG. 46). The index of the inflection or transition point, then, is the truncation index for the tSVD. The singular value at the index is used in the Tikhonov filter factor. Koh et al. determined the transition point by fitting two different linear models to the data in the Picard plot and using a sum of squared error criterion to determine the transition point.

APPENDIX 2

Fleischmann and Hittmair used Fourier methods to perform the deconvolution necessary to estimate the patient/drug transfer function. If $u_t(n)$ is the discrete-time test bolus(units ml/s), $y_t(n)$ is the discrete-time signal representing the response of the patient and drug as measured by the scanner (Hounsfield Units). Assuming the contrast media and vascular system behave as a linear time invariant system, the estimated system impulse response was found by deconvolution:

$$h(\hat{n}) = y_t(n) \otimes^{-1} u_t(n) \quad (B1)$$

In the Z-domain, the deconvolution operation, $\otimes^{-1}$, is a spectral division:

$$h(\hat{n}) = Z^{-1}\{H(z)\} = Z^{-1}\left\{\frac{Y_t(z)}{U_t(z)}\right\} \quad (B2)$$

where $Z^{-1}$ represents the inverse z-transform operator. Discrete-time operations were performed because the patient response signal, $y_t(n)$ was sampled every 1 or 2 seconds by the CT scanner. Contrast enhancement was measured by applying circular Regions Of Interest (ROI) over the abdominal aorta proximal to the iliac arteries.

To reduce the influence of high frequency noise (assumed to be non-physiological), Fleischmann and Hittmair filtered the output spectrum by multiplication with an exponential kernel (m is a scaling factor):

$$Y_t(k)' = Y_t(k) \cdot e^{-\frac{m}{k}} \quad (B3)$$

Because the zero or small values in the denominator of equation B2 can cause numerical instabilities, they ensured H(k) was zero when $U_t(k)$ was zero by multiplying the filtered output spectrum by a masking signum function, sgn(x) defined as:

$$\text{sgn}(x) = \begin{cases} -1 & \text{if } x < 0 \\ 0 & \text{if } x = 0 \\ 1 & \text{if } x > 0 \end{cases} \quad \text{(B4)}$$

The estimated transfer function of the patient/drug system was:

$$H(k) = \frac{Y_t(\hat{k})' \cdot T_f(k)}{U_t(k)'} \quad \text{(B5)}$$

with:

$$T_f(k) = \text{sgn}(|U_t(k)|) \quad \text{(B6)}$$

the signum masking function preventing the transfer function estimate from growing unbounded.

Their goal was to determine the input necessary to give a desired enhancement response during a diagnostic CT scan. The ideal contrast input function was computed by:

$$U_d(k) = \frac{Y_d(k)}{|H(\hat{k})|} \quad \text{(B7)}$$

An inverse, discrete Fourier Transform of equation B7 determined the input function necessary to achieve the desired enhancement level in time.

In general, the raw, computed input function is not realizable because negative flow rates were generated and the flow rates often exceeded 8 ml/s. Flow rates are limited by clinical and system constraints to 6-7 ml/s due to material strength limits of the syringe, tubing and catheters. The pressure generated in the system is a function of contrast medium viscosity, catheter gauge (or inner diameter), tubing length and diameter, and patient's vascular status. Therefore, many radiologists reduce the maximum flow rate for a patient depending on the condition of the vascular access site, the patient's health status, or confidence of the clinician administering the drug. To produce realizable injection profiles, Fleischmann and Hittmair applied a heuristic to the contrast injection protocol that prevented negative flow rates and rounded the continuously varying function so that a contrast injection system could realize the injection. No explicit algorithm describing the truncation, however, was described in [9] or [36] although some MATHEMATICA code was included in [8].

What is claimed is:

1. A method of controlling injection of a contrast medium comprising a contrast enhancing agent into a patient in an injection procedure, the method comprising:
   providing a control system operably associated with a first pressurizing drive member, the first pressurizing drive member being adapted to be operably associated with at least a first fluid container, and the first fluid container being adapted to contain the contrast medium; and
   determining at least one parameter for the injection procedure via which the control system controls the first pressurizing drive member by modeling, prior to the injection procedure, propagation of the contrast medium to be injected into the patient using a physiologically based pharmacokinetic model stored in a memory system in connection with the control system, wherein the physiologically based pharmacokinetic model has incorporated therein a non-linear saturation term in a peripheral venous compartment, wherein exogenous administration of the contrast enhancing agent is provided by the equation $u_{exog}(t) = C_{inj}(t) \cdot Q_{inj}(t)$ wherein $C_{inj}(t)$ is a concentration of the contrast enhancing agent as a function of time and $Q_{inj}(t)$ is an administration flow rate of contrast as a function of time, but wherein $Q_{inj}(t)$ is a constant equal to a predetermined limiting administration flow rate at administration flow rates equal to or greater than the limiting administration flow rate.

2. The method of claim 1, wherein the physiologically based pharmacokinetic model is adapted to estimate a time enhancement curve for a region of interest of the patient.

3. The method of claim 2, further comprising:
   using the physiologically based pharmacokinetic model to estimate the time enhancement curve for the patient: and
   determining at least one parameter of the injection procedure at least in part on the basis of the estimated time enhancement cure.

4. The method of claim 1, wherein the physiologically based pharmacokinetic model is adapted to model propagation of the contrast medium after injection of the contrast medium has ceased.

5. The method of claim 4, wherein the physiologically based pharmacokinetic model models a volumetric flow rate of blood and an effect thereof on propagation of the contrast medium.

6. The method of claim 5 wherein the physiologically based pharmacokinetic model models the effect on propagation of the contrast medium upon injection of a fluid containing no contrast enhancing agent after injection of the contrast medium, wherein the effect of volumetric flow rate of exogenous fluid on the volumetric flow rate of blood is considered in the physiologically based pharmacokinetic model.

7. The method of claim 1, wherein at least one parameter for the physiologically based pharmacokinetic model is determined at least partially on the basis of data from multiple individuals.

8. The method of claim 1, wherein at least one parameter for the physiologically based pharmacokinetic model is determined at least partially on the basis of at least one patient specific variable.

9. The method of claim 1, wherein at least one parameter for the physiologically based pharmacokinetic model is determined at least in part from at least one time enhancement curve of the patient resulting from an injection of the contrast medium.

10. The method of claim 1, wherein the physiologically based pharmacokinetic model is incorporated in a system comprising an injector system and an imaging system and is used in generating at least one parameter for the injection procedure.

11. The method of claim 1 further comprising:
    incorporating into the physiologically based pharmacokinetic model at least one configurable transport delay term through at least one compartment.

12. The method of claim 11, wherein the at least one configurable transport delay term is configurable at least in part on the basis of at least one patient specific variable.

13. A method of controlling injection of a contrast medium including a contrast enhancing agent into a patient in an in procedure, the method comprising:

providing a control system operably associated with a first pressurizing drive member, the first pressurizing drive member being adapted to be operably associated with at least a first fluid container, and the first fluid container being adapted to contain the contrast medium; and determining at least one parameter for the injection procedure via which the control system controls the first pressurizing drive member by modeling, prior to the injection procedure, propagation of the contrast medium to be injected into the patient using a compartmental physiologically based pharmacokinetic model comprising a peripheral venous compartment, wherein the compartmental physiologically based pharmacokinetic model is saved in a memory system in connection with the control system, the determining comprising:

modeling a volumetric flow rate of blood and an effect thereof on the propagation of contrast medium comprising inclusion of a parameter for a volumetric flow rate of an exogenous fluid in the physiologically based pharmacokinetic model, wherein the volumetric flow rate of blood and the volumetric flow rate of the exogenous fluid are treated independently and the effect of the volumetric flow rate of the exogenous fluid on the volumetric flow rate of blood is considered in mass balances in the peripheral venous compartment of the compartmental physiologically based pharmacokinetic model.

14. The method of claim 13, wherein the compartmental physiologically based pharmacokinetic model models an effect on propagation of the contrast medium upon injection of a fluid containing no contrast enhancing agent after injection of the contrast medium.

15. The method of claim 14, wherein the compartmental physiologically based pharmacokinetic model is adapted to estimate a time enhancement curve for a region of interest of the patient.

16. The method of claim 15, further comprising:
using the compartmental physiologically based pharmacokinetic model to estimate the time enhancement curve for the patient; and
determining at least one parameter of the injection procedure at least in part on the basis of the estimated time enhancement curve.

17. The method of claim 16, further comprising:
using the time enhancement curve during a diagnostic injection of the contrast medium to update the compartmental physiologically based pharmacokinetic model and to alter at least one parameter of the injection procedure.

18. The method of claim 14, wherein the compartmental physiologically based pharmacokinetic model comprises at least one non-linear saturation term in the peripheral venous compartment or at least one configurable transport delay term through at least one compartment.

19. The method of claim 14, wherein at least one parameter for the compartmental physiologically based pharmacokinetic model is determined at least in part on the basis of data from multiple individuals.

20. The method of claim 14, wherein at least one parameter for the compartmental physiologically based pharmacokinetic model is determined at least partially on the basis of at least one patient specific variable.

21. The method of claim 14, wherein at least one parameter for the compartmental physiologically based pharmacokinetic model is determined at least in part on the basis of at least one time enhancement curve of the patient resulting from an injection of the contrast medium.

22. A system comprising:
a first pressurizing drive member adapted to be operably associated with at least a first fluid container, the first fluid container being adapted to contain a contrast medium comprising a contrast enhancing agent;
a control system operably associated with the first pressurizing drive member;
a memory system in connection with the control system; and
a parameter generation system stored in the memory system to determine at least one parameter via which the control system controls the first pressurizing drive member during an injection procedure, the parameter generator system comprising a physiologically based pharmacokinetic model to model, prior to the injection procedure, propagation of the contrast medium to be injected into a patient, the physiologically based pharmacokinetic model comprising a non-linear saturation term in a peripheral venous compartment, wherein exogenous administration of the contrast enhancing agent is provided by the equation $u_{exog}(t)=C_{inj}(t) \cdot Q_{inj}(t)$ wherein $C_{inj}(t)$ is a concentration of the contrast enhancing agent as a function of time and $Q_{inj}(t)$ is an administration flow rate of contrast as a function of time, but wherein $Q_{inj}(t)$ is a constant equal to a predetermined limiting administration flow rate at administration flow rates equal to or greater than the limiting administration flow rate.

23. The system of claim 22, wherein at least one parameter for the physiologically based pharmacokinetic model is determined at least in part from at least one time enhancement curve of the patient.

24. The system of claim 22, further comprising:
non-parametric model to model propagation of the contrast medium injected into the patient.

25. The system of claim 24, wherein the at least one parameter is determined using an optimization method on the basis of at least one of the physiologically based pharmacokinetic model or the non-parametric model.

26. The system of claim 22, wherein the at least one parameter is determined using an optimization method on the basis of the physiologically based pharmacokinetic model.

27. The system of claim 22, wherein the physiologically based pharmacokinetic model further comprises at least one configurable transport delay term through at least one compartment.

28. The system of claim 22, wherein the physiologically based pharmacokinetic model further comprises an adaptation to model a volumetric flow rate of blood and an effect thereof on the propagation of the contrast medium after injection of the contrast medium ceases, wherein the effect of volumetric flow rate of exogenous fluid on the volumetric flow rate of blood is considered in the physiologically based pharmacokinetic model.

* * * * *

UNITED STATES PATENT AND TRADEMARK OFFICE
CERTIFICATE OF CORRECTION

PATENT NO. : 9,959,389 B2
APPLICATION NO. : 13/806121
DATED : May 1, 2018
INVENTOR(S) : Kalafut It is certified that error appears in the above-identified patent and that said Letters Patent is hereby corrected as shown below:

In the Specification

In Column 7, Line 44, delete "110 lb female while patient 8" and insert -- 110 lbs female while subject 8 --, therefor.
In Column 9, Line 63, delete "Table 18" and insert -- Table 16 --, therefor.
In Column 13, Line 17, delete "FIG. 2B)" and insert -- FIG. 1B) --, therefor.
In Column 13, Lines 42-43, delete "memory system 520 a display" and insert -- memory system 530, a display --, therefor.
In Column 17, Line 34, delete "$K_{LUNG\_BT}$" and insert -- $k_{LUNG\_BT}$ --, therefor.
In Column 18, Line 18, in Equation (14), delete "$x_{CP}[x_{RH}x_{LUNG}x_{LH}]$" and insert -- $x_{CP} = [x_{RH}\ x_{LUNG}\ x_{LH}]$ --, therefor.
In Column 20, Lines 56-58, delete "$\frac{\left(\frac{V_{PER}}{2}\right)}{(Q_{vein} + Q_{Inj})}$" and insert -- $\frac{\left(\frac{V_{PER}}{2}\right)}{(Q_{vein} + Q_{inj})}$ --, therefor.
In Column 22, Line 52, delete "Glomelular" and insert -- Glomerular --, therefor.
In Column 24, Line 5, delete "Table 3" and insert -- Table 2A --, therefor.
In Column 24, Line 13, delete "TABLE 2" and insert -- TABLE 2A --, therefor.
In Column 24, Line 14, delete "data Mean data" and insert -- mean data --, therefor.
In Column 24, Line 20, delete "+/ 10.2" and insert -- +/- 10.2 --, therefor.
In Column 26, Line 28, delete "ml/and" and insert -- ml/s and --, therefor.
In Column 29, Line 34, delete "yRH(n)" and insert -- yLH(n) --, therefor.
In Column 29, Line 46, delete "yRH(n)" and insert -- yLH(n) --, therefor.
In Column 29, Line 56, delete "HE1" and insert -- He1 --, therefor.
In Column 30, Line 17, in Equation (31), delete "$D_{H1} = [0]$" and insert -- $D_{He1} = [0]$ --, therefor.
In Column 33, Line 9, delete "42 and" and insert -- 41 and --, therefor.
In Column 35, Line 20, delete "$\theta_{He1D}^{true}$" and insert -- $\theta_{HeiD}^{true}$ --, therefor.
In Column 37, Line 47, delete "yLH." and insert -- $y_{LH.}$ --, therefor.
In Column 38, Line 47, delete "Table 9" and insert -- Table 11 --, therefor.
In Column 39, Line 1, delete "TABLE 9" and insert -- TABLE 11 --, therefor.

Signed and Sealed this
Twenty-fifth Day of June, 2019

Andrei Iancu
*Director of the United States Patent and Trademark Office*

CERTIFICATE OF CORRECTION (continued)
U.S. Pat. No. 9,959,389 B2

In Column 42, Line 36, delete "TABLE 10" and insert -- TABLE 14 --, therefor.
In Column 44, Line 17, delete "TABLE 11" and insert -- TABLE 15 --, therefor.
In Column 51, Line 61, delete "9.".
In Column 53, Line 4, delete "(maxlter)" and insert -- (maxIter) --, therefor.
In Column 54, Line 27, delete "TECs ($y_{RH}^{Test}(n)$), $y_{LH}^{Test}(n)$)" and insert -- $TECs(y_{RH}^{Test}(n), y_{LH}^{Test}(n))$ --, therefor.

In the Claims

In Column 60, Line 19, in Claim 3, delete "patient:" and insert -- patient; --, therefor.
In Column 60, Line 23, in Claim 3, delete "cure." and insert -- curve. --, therefor.
In Column 60, Line 67, in Claim 13, delete "an in" and insert -- an injection --, therefor.
In Column 62, Line 40, in Claim 24, delete "non-parametric" and insert -- a non-parametric --, therefor.